(12) United States Patent
Masters

(10) Patent No.: US 7,749,445 B2
(45) Date of Patent: *Jul. 6, 2010

(54) METHOD AND APPARATUS FOR ANALYZING BIOPROCESS FLUIDS

(75) Inventor: Brett P. Masters, Belmont, CA (US)

(73) Assignee: BioScale, Inc., Cambridge, MA (US)

( * ) Notice: Subject to any disclaimer, the term of this patent is extended or adjusted under 35 U.S.C. 154(b) by 483 days.

This patent is subject to a terminal disclaimer.

(21) Appl. No.: 11/641,280

(22) Filed: Dec. 19, 2006

(65) Prior Publication Data

US 2007/0224700 A1 Sep. 27, 2007

Related U.S. Application Data

(63) Continuation-in-part of application No. 11/416,789, filed on May 2, 2006, now Pat. No. 7,648,844, which is a continuation-in-part of application No. 11/183,484, (Continued)

(60) Provisional application No. 60/751,492, filed on Dec. 19, 2005, provisional application No. 60/676,759, filed on May 2, 2005, provisional application No. 60/690,592, filed on Jun. 15, 2005.

(51) Int. Cl.
*G01N 27/00* (2006.01)
*G01N 27/12* (2006.01)
*G01N 33/53* (2006.01)
*G01N 33/532* (2006.01)
*G01N 33/543* (2006.01)
*G01N 33/553* (2006.01)

(52) U.S. Cl. ............ 422/82.01; 422/68.1; 422/81; 422/81.13; 422/100; 422/104; 435/7.1; 435/7.94; 435/287.2; 435/287.3; 436/523; 436/525; 436/526; 436/168

(58) Field of Classification Search .............. None
See application file for complete search history.

(56) References Cited

U.S. PATENT DOCUMENTS 4,098,876 A 7/1978 Piasio et al.
(Continued)

FOREIGN PATENT DOCUMENTS

EP 1752663 2/2007
(Continued)

OTHER PUBLICATIONS

U.S. Appl. No. 11/183,484, filed Jul. 18, 2005, Miller et al.
(Continued)

*Primary Examiner*—Unsu Jung
(74) *Attorney, Agent, or Firm*—Proskauer Rose LLP

(57) ABSTRACT

Methods and apparatus for analyzing bioprocess fluids are provided. A plurality of particles coated with a plurality of capture agents having an affinity for one or more biological markers is combined with bioprocess fluid to form a plurality of analyte-particle complexes. The system also includes a transport arrangement for transporting the sample to a sensor surface, and optionally a magnetic field inducing structure constructed and arranged to establish a magnetic field at and adjacent to the sensor surface. The resonant sensor produces a signal corresponding to an amount of analyte-particle complexes that are bound to the sensor surface.

8 Claims, 19 Drawing Sheets

Related U.S. Application Data filed on Jul. 18, 2005, now Pat. No. 7,300,631, application No. 11/641,280, which is a continuation-in-part of application No. 11/417,000, filed on May 2, 2006, now Pat. No. 7,615,381, which is a continuation-in-part of application No. 11/183,484, application No. 11/641,280, which is a continuation-in-part of application No. 11/416,624, filed on May 2, 2006, now Pat. No. 7,611,908, which is a continuation-in-part of application No. 11/183,484, application No. 11/641,280, which is a continuation-in-part of application No. 11/417,005, filed on May 2, 2006, now Pat. No. 7,598,094, which is a continuation-in-part of application No. 11/183,484, application No. 11/641,280, which is a continuation-in-part of application No. 11/416,998, filed on May 2, 2006, now Pat. No. 7,629,137, which is a continuation-in-part of application No. 11/183,484, application No. 11/641,280, which is a continuation-in-part of application No. 11/416,997, filed on May 2, 2006, now Pat. No. 7,632,638, which is a continuation-in-part of application No. 11/183,484.

(56) References Cited

U.S. PATENT DOCUMENTS

| | | | | |
|---|---|---|---|---|
| 4,551,435 | A | 11/1985 | Liberti et al. | 436/541 |
| 4,596,697 | A | 6/1986 | Ballato | 422/98 |
| 4,752,855 | A | 6/1988 | Fedter | 361/286 |
| 4,795,698 | A | 1/1989 | Owen et al. | 435/4 |
| 4,896,098 | A | 1/1990 | Haritonidis et al. | 324/663 |
| 4,920,450 | A | 4/1990 | Masiulis | 361/282 |
| 4,925,788 | A | 5/1990 | Liberti | 435/7 |
| 4,997,278 | A | 3/1991 | Finlan et al. | 356/128 |
| 5,023,053 | A | 6/1991 | Finlan | 422/82.05 |
| 5,025,346 | A | 6/1991 | Tang et al. | 361/283.1 |
| 5,035,863 | A | 7/1991 | Finlan et al. | 422/82.05 |
| 5,047,213 | A | 9/1991 | Finlan et al. | 422/82.11 |
| 5,055,265 | A | 10/1991 | Finlan | 422/82.05 |
| 5,064,619 | A | 11/1991 | Finlan | 422/82.05 |
| 5,079,600 | A | 1/1992 | Schnur et al. | 257/750 |
| 5,104,790 | A | 4/1992 | Flesher et al. | |
| 5,108,933 | A | 4/1992 | Liberti et al. | 436/501 |
| 5,129,262 | A | 7/1992 | White et al. | 73/599 |
| 5,164,589 | A | 11/1992 | Sjödin | 250/227.24 |
| 5,186,827 | A | 2/1993 | Liberti et al. | 210/222 |
| 5,189,914 | A | 3/1993 | White et al. | 73/599 |
| 5,199,298 | A | 4/1993 | Ng et al. | 73/54.01 |
| 5,200,084 | A | 4/1993 | Liberti et al. | 210/695 |
| 5,242,828 | A | 9/1993 | Bergström et al. | 435/291 |
| 5,252,743 | A * | 10/1993 | Barrett et al. | 548/303.7 |
| 5,304,465 | A | 4/1994 | Garland et al. | 435/4 |
| 5,306,644 | A | 4/1994 | Meyerholtz et al. | 436/149 |
| 5,313,264 | A | 5/1994 | Ivarsson et al. | 356/73 |
| 5,376,252 | A | 12/1994 | Ekström et al. | 204/299 |
| 5,411,709 | A | 5/1995 | Furuki et al. | 422/91 |
| 5,436,161 | A | 7/1995 | Bergström et al. | 435/291 |
| 5,442,448 | A | 8/1995 | Knoll | 356/445 |
| 5,443,890 | A | 8/1995 | Öhman | 428/167 |
| 5,445,971 | A * | 8/1995 | Rohr | 436/526 |
| 5,451,683 | A | 9/1995 | Barrett et al. | 548/302.7 |
| 5,454,904 | A | 10/1995 | Ghezzo et al. | 216/13 |
| 5,455,178 | A | 10/1995 | Fattinger | 436/164 |
| 5,458,852 | A | 10/1995 | Buechler | 422/58 |
| 5,479,260 | A | 12/1995 | Fattinger | 356/361 |
| 5,482,867 | A | 1/1996 | Barrett et al. | 436/518 |
| 5,490,034 | A | 2/1996 | Zavracky et al. | 361/283.4 |
| 5,492,840 | A | 2/1996 | Malmqvist et al. | 436/518 |
| 5,512,131 | A | 4/1996 | Kumar et al. | 438/738 |
| 5,554,541 | A | 9/1996 | Malmqvist et al. | 436/518 |
| 5,593,130 | A | 1/1997 | Hansson et al. | 251/61.1 |
| 5,620,850 | A | 4/1997 | Bamdad et al. | 530/300 |
| 5,641,640 | A | 6/1997 | Hanning | 435/7.92 |
| 5,656,428 | A | 8/1997 | McAllister et al. | 435/6 |
| 5,656,504 | A | 8/1997 | Johansson et al. | 436/518 |
| 5,660,985 | A | 8/1997 | Pieken et al. | 435/6 |
| 5,663,790 | A | 9/1997 | Ekström et al. | 356/128 |
| 5,668,303 | A | 9/1997 | Giesler et al. | 73/24.06 |
| 5,705,402 | A | 1/1998 | Leland et al. | 436/526 |
| 5,716,854 | A | 2/1998 | Löfas et al. | 436/518 |
| 5,719,324 | A | 2/1998 | Thundat et al. | 73/24.01 |
| 5,744,367 | A | 4/1998 | Talley et al. | 436/172 |
| 5,753,518 | A | 5/1998 | Karlsson | 436/517 |
| 5,763,191 | A | 6/1998 | Knoll et al. | 435/7.1 |
| 5,776,748 | A | 7/1998 | Singhvi et al. | 435/180 |
| 5,795,725 | A | 8/1998 | Buechler et al. | 435/7.1 |
| 5,827,669 | A * | 10/1998 | Nakayama et al. | 435/7.5 |
| 5,836,203 | A | 11/1998 | Martin et al. | 73/579 |
| 5,851,840 | A | 12/1998 | Sluka et al. | 436/525 |
| 5,885,527 | A | 3/1999 | Buechler | 422/58 |
| 5,900,160 | A | 5/1999 | Whitesides et al. | 216/41 |
| 5,912,181 | A | 6/1999 | Petcavich | 436/151 |
| 5,922,594 | A | 7/1999 | Löfas | 435/291 |
| 5,922,615 | A | 7/1999 | Nowakowski et al. | 436/518 |
| 5,932,296 | A | 8/1999 | Sluka et al. | 427/491 |
| 5,947,124 | A | 9/1999 | Buechler et al. | 128/898 |
| 5,955,729 | A | 9/1999 | Nelson et al. | 250/282 |
| 5,965,456 | A | 10/1999 | Malmqvist et al. | 436/514 |
| 5,972,612 | A | 10/1999 | Malmqvist et al. | 435/6 |
| 6,006,589 | A | 12/1999 | Rodahl et al. | 73/54.41 |
| 6,008,893 | A | 12/1999 | Roos et al. | 356/246 |
| 6,019,944 | A | 2/2000 | Buechler | 422/58 |
| 6,033,852 | A | 3/2000 | Andle et al. | 435/6 |
| 6,046,585 | A | 4/2000 | Simmonds | 324/239 |
| 6,106,779 | A | 8/2000 | Buechler et al. | 422/55 |
| 6,113,855 | A | 9/2000 | Buechler | 422/58 |
| 6,123,819 | A | 9/2000 | Peeters | 204/403 |
| 6,127,183 | A | 10/2000 | Ivarsson et al. | 436/34 |
| 6,133,043 | A | 10/2000 | Talley et al. | 436/172 |
| 6,143,513 | A | 11/2000 | Löfas | 435/24 |
| 6,143,574 | A | 11/2000 | Karlsson et al. | 436/517 |
| 6,143,576 | A | 11/2000 | Buechler | 436/518 |
| 6,156,270 | A | 12/2000 | Buechler | 422/58 |
| 6,194,223 | B1 | 2/2001 | Herrmann et al. | 436/518 |
| 6,197,515 | B1 | 3/2001 | Bamdad et al. | 435/6 |
| 6,200,814 | B1 | 3/2001 | Malmqvist et al. | 436/52 |
| 6,207,381 | B1 | 3/2001 | Larsson et al. | 435/6 |
| 6,208,814 | B1 | 3/2001 | Malmqvist et al. | 436/52 |
| 6,221,674 | B1 | 4/2001 | Sluka et al. | 436/166 |
| 6,222,619 | B1 | 4/2001 | Herron et al. | 356/39 |
| 6,271,040 | B1 | 8/2001 | Buechler | 436/170 |
| 6,275,031 | B1 | 8/2001 | Simmonds | 324/239 |
| 6,275,137 | B1 | 8/2001 | Doppalapudi et al. | 338/2 |
| 6,287,758 | B1 | 9/2001 | Okun et al. | 435/4 |
| 6,289,286 | B1 | 9/2001 | Anderson et al. | 702/19 |
| 6,295,861 | B1 | 10/2001 | Tom et al. | 73/24.06 |
| 6,297,060 | B1 | 10/2001 | Nowakowski et al. | 436/518 |
| 6,302,919 | B1 | 10/2001 | Chambers et al. | 210/781 |
| 6,306,614 | B1 | 10/2001 | Romaschin et al. | 435/7.2 |
| 6,322,979 | B1 | 11/2001 | Bamdad et al. | 435/6 |
| 6,326,563 | B1 | 12/2001 | Takeuchi et al. | 177/210 FP |
| 6,329,209 | B1 | 12/2001 | Wagner et al. | 436/518 |
| 6,348,318 | B1 | 2/2002 | Valkirs | 435/7.1 |
| 6,365,418 | B1 | 4/2002 | Wagner et al. | 436/518 |
| 6,368,838 | B1 | 4/2002 | Singhvi et al. | 435/177 |
| 6,368,877 | B1 | 4/2002 | Zhang et al. | 436/527 |
| 6,391,265 | B1 | 5/2002 | Buechler et al. | 422/101 |
| 6,406,921 | B1 | 6/2002 | Wagner et al. | 436/518 |
| 6,437,563 | B1 | 8/2002 | Simmonds et al. | 324/239 |
| 6,454,924 | B2 | 9/2002 | Jedrzejewski et al. | 204/601 |
| 6,455,980 | B1 | 9/2002 | Bernstein | 310/324 |
| 6,457,361 | B1 | 10/2002 | Takeuchi et al. | 73/580 |
| 6,472,148 | B1 | 10/2002 | Bamdad et al. | 435/6 |

| | | | |
|---|---|---|---|
| 6,475,808 B1 | 11/2002 | Wagner et al. | 436/518 |
| 6,483,303 B2 | 11/2002 | Simmonds et al. | 324/239 |
| 6,485,982 B1 | 11/2002 | Charlton | 436/514 |
| 6,493,097 B1 | 12/2002 | Ivarsson | 356/630 |
| 6,503,760 B2 | 1/2003 | Malmqvist et al. | 436/518 |
| 6,506,620 B1 | 1/2003 | Scharf et al. | 438/52 |
| 6,509,059 B2 | 1/2003 | Yang et al. | 427/230 |
| 6,511,915 B2 | 1/2003 | Mlcak | 438/695 |
| 6,518,168 B1 | 2/2003 | Clem et al. | 438/623 |
| 6,518,747 B2 | 2/2003 | Sager et al. | 324/204 |
| 6,544,674 B2 | 4/2003 | Tuller et al. | 428/698 |
| 6,576,478 B1 | 6/2003 | Wagner et al. | 436/518 |
| 6,582,969 B1 | 6/2003 | Wagner et al. | 436/518 |
| 6,589,727 B1 | 7/2003 | Klenerman et al. | 435/4 |
| 6,589,798 B1 | 7/2003 | Löfas | 436/518 |
| 6,596,545 B1 | 7/2003 | Wagner et al. | 436/518 |
| 6,597,176 B2 | 7/2003 | Simmonds et al. | 324/326 |
| 6,607,922 B2 | 8/2003 | LaBorde | 436/514 |
| 6,627,404 B1 | 9/2003 | Buechler et al. | 435/7.1 |
| 6,627,959 B1 | 9/2003 | Tuller et al. | 257/367 |
| 6,627,965 B1 | 9/2003 | Tuller et al. | 257/415 |
| 6,630,358 B1 | 10/2003 | Wagner et al. | 436/518 |
| 6,647,764 B1 | 11/2003 | Paul et al. | 73/54.41 |
| 6,669,907 B1 | 12/2003 | Buechler | 422/58 |
| 6,688,158 B2 | 2/2004 | Cunningham et al. | 73/24.06 |
| 6,698,454 B2 | 3/2004 | Sjölander et al. | 137/885 |
| 6,716,620 B2 | 4/2004 | Bashir et al. | 435/287.2 |
| 6,720,710 B1 | 4/2004 | Wenzel et al. | 310/328 |
| 6,767,510 B1 | 7/2004 | Buechler | 422/58 |
| 6,775,003 B2 | 8/2004 | Ivarsson | 356/454 |
| 6,790,775 B2 | 9/2004 | Fartash | 438/667 |
| 6,795,273 B2 | 9/2004 | Minor et al. | 360/126 |
| 6,825,715 B2 | 11/2004 | Andle | 329/370 |
| 6,848,295 B2 | 2/2005 | Auner et al. | 73/24.06 |
| 6,848,299 B2 | 2/2005 | Paul et al. | 73/64.53 |
| 6,901,278 B1 | 5/2005 | Notelovitz | 600/407 |
| 6,936,424 B1 | 8/2005 | Watkins et al. | 435/7.1 |
| 7,118,922 B1 | 10/2006 | Bhansali et al. | 436/518 |
| 7,410,811 B2 | 8/2008 | Lin et al. | 436/526 |
| 2002/0012929 A1 | 1/2002 | Malmqvist et al. | 435/6 |
| 2002/0028519 A1* | 3/2002 | Yguerabide et al. | 436/518 |
| 2002/0042074 A1 | 4/2002 | Bamdad et al. | 435/6 |
| 2002/0048534 A1 | 4/2002 | Storek et al. | 422/99 |
| 2002/0048821 A1 | 4/2002 | Storek et al. | 436/174 |
| 2002/0070841 A1 | 6/2002 | Doppalapudi et al. | 338/5 |
| 2002/0086436 A1 | 7/2002 | Buechler | 436/164 |
| 2002/0094572 A1 | 7/2002 | Singhvi et al. | 435/395 |
| 2002/0115198 A1 | 8/2002 | Nerenberg et al. | 435/287.2 |
| 2002/0128593 A1 | 9/2002 | Sjolander et al. | 604/22 |
| 2002/0164819 A1 | 11/2002 | Storek et al. | 436/174 |
| 2002/0182717 A1 | 12/2002 | Karlsson | 435/287.2 |
| 2003/0010745 A1 | 1/2003 | Field | 216/2 |
| 2003/0012693 A1 | 1/2003 | Otillar et al. | 422/58 |
| 2003/0022388 A1 | 1/2003 | Roos et al. | 436/164 |
| 2003/0035758 A1 | 2/2003 | Buechler et al. | 422/101 |
| 2003/0100762 A1 | 5/2003 | Kaler et al. | 544/296 |
| 2003/0119220 A1 | 6/2003 | Mlcak et al. | 438/52 |
| 2003/0154031 A1 | 8/2003 | Potyrailo et al. | |
| 2003/0194710 A1 | 10/2003 | Yang | 435/6 |
| 2004/0002167 A1 | 1/2004 | Andersson et al. | 436/518 |
| 2004/0016297 A1 | 1/2004 | Paul et al. | 73/580 |
| 2004/0020275 A1 | 2/2004 | Paul et al. | 73/64.53 |
| 2004/0023413 A1 | 2/2004 | Opalsky | 436/518 |
| 2004/0038195 A1 | 2/2004 | Nerenberg et al. | 435/4 |
| 2004/0043423 A1 | 3/2004 | Bellew et al. | 435/7.1 |
| 2004/0043615 A1 | 3/2004 | Yamamoto et al. | 438/689 |
| 2004/0058456 A1 | 3/2004 | Safsten et al. | 436/518 |
| 2004/0101990 A1 | 5/2004 | Dunn | |
| 2004/0132005 A1 | 7/2004 | Hsu et al. | 435/4 |
| 2004/0161860 A1 | 8/2004 | Richalet-Secordel et al. | 436/518 |
| 2004/0166549 A1 | 8/2004 | Karlsson et al. | 435/7.92 |
| 2004/0166577 A1 | 8/2004 | Storek et al. | 435/287.2 |
| 2004/0217807 A1 | 11/2004 | Andle | 329/352 |
| 2004/0241724 A1 | 12/2004 | Karlsson et al. | 435/6 |
| 2004/0248213 A1 | 12/2004 | Karlsson et al. | 435/7.2 |
| 2005/0012431 A1 | 1/2005 | Andle | 310/331 D |
| 2005/0014179 A1 | 1/2005 | Karlsson et al. | 435/6 |
| 2005/0019933 A1 | 1/2005 | Andersson et al. | 436/52 |
| 2005/0040907 A1 | 2/2005 | Nebrigic | 332/118 |
| 2005/0057302 A1 | 3/2005 | Andle | 329/370 |
| 2005/0064619 A1 | 3/2005 | Chavan et al. | 438/52 |
| 2005/0074904 A1 | 4/2005 | Chin et al. | 436/526 |
| 2005/0148147 A1 | 7/2005 | Keating et al. | 438/299 |
| 2006/0019330 A1 | 1/2006 | Lakshmi et al. | 435/34 |
| 2006/0286685 A1 | 12/2006 | Miller et al. | |

FOREIGN PATENT DOCUMENTS

| | | |
|---|---|---|
| WO | 2004/053105 A2 | 6/2004 |
| WO | WO 2004/053105 | 6/2004 |
| WO | WO 2005/111426 | 11/2005 |
| WO | 2006/119308 A | 11/2006 |

OTHER PUBLICATIONS

U.S. Appl. No. 11/709,068, filed Feb. 21, 2007, Miller et al.
U.S. Appl. No. 11/416,789, filed May 2, 2006, Srivastava et al.
U.S. Appl. No. 11/417,000, filed May 2, 2006, Masters et al.
U.S. Appl. No. 11/416,624, filed May 2, 2006, Miller et al.
U.S. Appl. No. 11/417,005, filed May 2, 2006, Masters et al.
U.S. Appl. No. 11/416,998, filed May 2, 2006, Sauer-Budge et al.
U.S. Appl. No. 11/416,997, filed May 2, 2006, Sauer-Budge et al.
R. C. Jones, "A New Calculus for the Treatment of Optical Systems," Reprinted from J. Opt. Soc. Am., vol. 31, Jul. 1941, pp. 488-493.
R. M. White, "Direct Piezoelectric Coupling to Surface Elastic Waves," Applied Physics Letters, vol. 7 (Dec. 15, 1965), pp. 314-316.
K. Toda, "Lamb-wave delay lines with interdigital electrodes," J. Appl. Phys., vol. 44 (Jan. 1973), pp. 56-62.
M. Lewis, "Surface acoustic wave devices and applications: 6. Oscillators—the next most successful surface acoustic wave device?," Ultrasonics, May 1974, pp. 115-123.
J. F. Dias et al., "Frequency/Stress Sensitivity of S.A.W. Resonators," Electronics Letters, vol. 12, No. 22, Oct. 1976, pp. 580-582.
P. Das, "A Pressure Sensing Acoustic Surface Wave Resonator," 1976 Ultrasonics Symposium Proceedings, IEEE, 1976, pp. 306-308.
T. Reeder et al., "Surface-Acoustic-Wave Pressure and Temperature Sensors," Proceedings of the IEEE, vol. 64 (May 1976), pp. 754-756.
G. I. Bell, "Models for the Specific Adhesion of Cells to Cells," Science, New Series, vol. 200, Issue 4342, May 12, 1978, pp. 618-627.
S. W. Wenzel, "Applications of Ultrasonic Lamb Waves," dissertation submitted in partial satisfaction of the requirements for the degree of Doctor of Philosophy in Engineering/Electrical Engineering and Computer Sciences, University of California at Davis (1982).
N. D. Sinha et al., "Polymer support oligonucleotide synthesis XVIII$_{1,2}$: use of β-cyanoethyl-N,N-dialkylamino-/N-morpholino phosphoramidite of deoxynucleosides for the synthesis of DNA fragments simplifying deprotection and isolation of the final product," Nucleic Acids Research, vol. 12 (1984), pp. 4539-4557.
R. M. Langdon, "Resonator sensors—a review," Journal of Physics E: Scientific Instruments, vol. 18, No. 2, 1985, pp. 103-115.
T. Gast, "Sensors with oscillating elements," J. Phys. E: Sci. Instrum., vol. 18, 1985, pp. 783-789.
R. M. White, "Thermoelastic Coupling to Lamb Waves," IEEE Ultrasonics Symposium (1986), pp. 411-415.
D. Hauden, "Miniaturized Bulk and Surface Acoustic Wave Quartz Oscillators Used as Sensors," IEEE Transactions of Ultrasonics, Ferroelectrics, and Frequency Control, vol. UFFC-34, No. 2, Mar. 1987, pp. 253-258.
A. J. Ricco et al., "Acoustic wave viscosity sensor," Applied Physics Letters, vol. 50 (May 25, 1987), pp. 1474-1476.
R. M. White et al., "Plate-Mode Ultrasonic Oscillator Sensors," IEEE Transactions on Ultrasonics, Ferroelectrics, and Frequency Control, vol. 34 (Mar. 1987), pp. 162-171.
Y. Kurihara et al., "The Influence of Moisture on Surface Properties and Insulation Characteristics of AlN Substrates," IEEE Transactions of Components, Hybrids, and Manufacturing Technology, vol. 12, No. 3, Sep. 1989, pp. 330-334.

S. W. Wenzel et al., "Analytic comparison of the sensitivities of bulk-wave, surface-wave, and flexural plate-wave ultrasonic gravimetric sensors," Appl. Phys. Lett., vol. 54, No. 20, May 15, 1989, pp. 1976-1978.

W. D. Huse et al., "Generation of a Large Combinatorial Library of the Immunoglobulin Repertoire in Phase Lamda," Science, vol. 246, (Dec. 8, 1989), pp. 1275-1281.

G. F. Joyce, "Amplification, mutation and selection of catalytic RNA," Gene, vol. 82 (1989), pp. 83-87.

F. Josse et al., "Analysis of Piezoelectric Bulk-Acoustic-Wave Resonators as Detectors in Viscous Conductive Liquids," IEEE Transactions on Ultrasonics, Ferroelectrics and Frequency Control, vol. 37, No. 5, Sep. 1990, pp. 359-368.

S. J. Martin et al., "Surface acoustic wave response to changes in viscoelastic film properties," Applied Physics Letters, vol. 57, No. 18, Oct. 29, 1990, pp. 1867-1869.

J. Neumeister et al., "A SAW Delay-line Oscillator as a High-resolution Temperature Sensor," Sensors and Actuators, (Mar. 1990), pp. 670-672.

T. Nomura et al., "Measurement of Acoustic Properties of Liquids Using SH-Type Surface Acoustic Waves," Ultrasonics Symposium (1990), p. 307-310, Tokyo, Japan.

W. C. Tang, "Electrostatic Comb Drive for Resonant Sensor and Actuator Applications," Ph.D. Thesis, Electrical Engineering and Computer Sciences, University of California Berkeley, Berkeley, CA, Nov. 1990.

G. M. Whitesides et al., "Wet Chemical Approaches to the Characterization of Organic Surfaces: Self-Assembled Monolayers, Wetting, and the Physical-Organic Chemistry of the Solid-Liquid Interface," Langmuir, vol. 6 (1990), pp. 87-96.

V. K. Chaudhary et al., "A rapid method of cloning functional variable-region antibody genes in Escherichia coli as single-chain immunotoxins," Proc. Natl. Acad. Sci., vol. 87 (Feb. 1990), pp. 1066-1070.

A. D. Ellington et al., "In Vitro selection of RNA molecules that bind specific ligands," Nature, vol. 346 (Aug. 30, 1990), pp. 818-822.

R. L. Mullinax et al., "Identification of human antibody fragment clones specific for tetanus toxoid in a bacteriophaseλ immunoexpression library," Proc. Natl. Acad. Sci., vol. 87 (Oct. 1990), pp. 8095-8099.

A. Plückthun, "Antibodies from Escherichia coli," Nature, vol. 347, (Oct. 4, 1990), pp. 497-498.

C. Tuerk et al., "Systematic Evolution of Ligands by Exponential Enrichment: RNA Ligands to Bacteriophasge T4 DNA Polymerase," Science, vol. 249 (Aug. 1990) pp. 505-510.

C. R. Wood et al., "High Level Synthesis of Immunoglobulins in Chinese hamster Ovary Cells," The Journal of Immunology, vol. 145 (Nov. 1, 1990), pp. 3011-3016.

R. L. Baer et al., "Phase Noise Measurements of Flexural Plate Wave Ultrasonic Sensors," 1991 IEEE Ultrasonics Symposium, 1991, pp. 321-326.

J. W. Grate et al., "Flexural Plate Wave Devices for Chemical Analysis," Analytical Chemistry, vol. 63, 1991, pp. 1552-1561.

D. Johannsmann et al., "Visco-elastic properties of thin films probed with a quartz crystal resonator," Makromol. Chem., Macromol. Symp., vol. 46, 1991, pp. 247-251.

K. Martin et al., "Characterization of a Quartz Crystal Microbalance with Simultaneous Mass and Liquid Loading," Analytical Chemical., vol. 63, 1991, pp. 2272-2281.

S. Sjölander et al., "Integrated Fluid Handling System for Biomolecular Interaction Analysis," Anal. chem., vol. 63 (1991), pp. 2338-2345.

J. Berg et al., "Bispecific antibodies that mediate killing of cells infected with human immunodeficiency virus of any strain," Proc. Natl. Acad. Sci., vol. 88 (Jun. 1991), pp. 4723-4727.

P. E. Nielsen et al., "Sequence-Selective Recognition of a DNA by Strand Displacement with a Thymine-Substituted Polyamide," Science, vol. 254 (Dec. 6, 1991), pp. 1497-1500.

B. J. Costello et al., "A Flexural-Plate-Wave Microbial Sensor," IEEE, 0-7803-0456-X/92, pp. 69-72.

Gianchandani et al., "A Bulk Silicon Dissolved Wafer Process for Microelectromechanical Devices," Journal of Microelectromechanical Systems, vol. 1, No. 2, Jun. 1992, pp. 77-85.

J. W. Grate et al., "Frequency-Independent and Frequency-Dependent Polymer Transitions Observed on Flexural Plate Wave Ultrasonic Sensors," Analytical Chemistry, vol. 64, 1992, pp. 413-423.

J. F. Ramalho Ortigao et al., "Antisense Effect of Oligodeoxynucleotides with Inverted Terminal Internucleotidic Linkages: A Minimal Modification Protecting against Nucleolytic Degradation," Antisense Research and Development, vol. 2 (1992), pp. 129-146.

A. Kumar et al., "Features of gold having micrometer to centimeter dimensions can be formed through a combination of stamping with an elastomeric stamp and an alkanethiol 'ink' followed by chemical etching," App. Phys. Letter, vol. 63, No. 14, Oct. 4, 1993, pp. 2002-2004.

T. W. Schneider et al., "Electrochemical Quartz Crystal Microbalance Studies of Adsorption and Desorption of Self-Assembled Monolayers of Alkyl Thiols on Gold," J. Am. Chem. Soc., vol. 115, 1993, pp. 12391-12397.

Giesler et al., "Electrostatic excitation and capacitive detection of flexural plate-waves," Sensors and Actuators A, vol. 36, 1993, pp. 113-119.

R. W. Glaser, "Antigen-Antibody Binding and Mass Transport by Convection and Diffusion to a Surface: A Two-Dimensional Computer Model of Binding and Dissociation Kinetics," Analytical Biochemistry, vol. 213, 1993, pp. 152-161.

J. W. Grate et al., "Acoustic Wave Microsensors—Part I" Analytical Chemistry, vol. 65, No. 21, Nov. 1, 1993, pp. 940A-948A.

J. W. Grate et al., "Acoustic Wave Microsensors—Part II" Analytical Chemistry, vol. 65, No. 22, Nov. 15, 1993, pp. 987A-996A.

J. W. Grate et al., "Smart Sensor System for Trace Organophosphorus and Organosulfur Vapor Detection Employing a Temperature-Controlled Array of Surface Acoustic Wave Sensors, Automated Sample Preconcentration, and Pattern Recognition," Analytical Chemistry, vol. 65, No. 14, Jul. 15, 1993, pp. 1868-1881.

W. C. Greene, "AIDS and the Immune System," Scientific American, Sep. 1993, pp. 99-105.

S. Loughin et al., "Electronic structure of aluminum nitride: Theory and experiment," Applied Physics Letters, vol. 63, No. 9, Aug. 30, 1993, pp. 1182-1184.

F. F. Froehlich et al, "Minimum detectable displacement in near-field scanning optical microscopy," Appl. Phys. Let., vol. 65, Oct. 31, 1994, pp. 2254-2256.

T. Giesler et al., "Electrostatically excited and capacitively detected flexural plate waves on thin silicon nitride membranes with chemical sensor applications," Sensors and Actuators B, vol. 18-19, 1994, pp. 103-106.

A. Kumar et al., "Pattering Self-Assembled Monolayers: Applications in Material Science," Langmuir, vol. 10, 1994, pp. 1498-1511.

H. Ron et al., "Alkanethiol Monolayers on Preoxidized Gold. Encapsulation of Gold Oxide under an Organic Monolayer," Langmuir, vol. 10, 1994, pp. 4566-4573.

S. Martin et al., "Dynamics and Response of Polymer-Coated Surface Acoustic Wave Devices: Effect of Biscoelastic Properties and Film Resonance," Analytical Chemistry, vol. 66 (1994), pp. 2201-2219.

P. Wagner et al., "Covalent anchoring of proteins onto gold-directed NHS-terminated self-assembled monolayers in aqueous buffers: SFM images of clathrin cages and triskelia," FEBS Letters, vol. 356 (1994), pp. 267-271.

S. J. Klug et al., "All you wanted to know about SELEX," Molecular Biology Reports, vol. 20 (1994), pp. 97-107.

R. A. McGill et al., "Choosing polymer coatings for chemical sensors," Chemtech (Sep. 1994), p. 27-37.

D. Courboin et al., "Surface roughness of ion implanted <100> silicon studied by atomic force microscopy," Surface Science, vol. 342, 1995, pp. L1111-L1115.

S. Löfas, "Dextran modified self-assembled monolayer surfaces for use in biointeraction analysis with surface plasmon resonance," Pure & Appl. Chem., vol. 67, No. 5, 1995, pp. 829-834.

J. W. Grate et al., "Dewetting Effects on Polymer-Coated Surface Acoustic Wave Vapor Sensors," Analytical Chemistry, vol. 67, No. 21, Nov. 1, 1995, pp. 4015-4019.

M. Rodahl et al., "Quartz crystal microbalance setup for frequency and Q-factor measurements in gaseous and liquid environments," Rev. Sci. Instrum, vol. 66 (Jul. 1995) pp. 3924-3930.

C. P. Quinn et al., "Copolymers for improving biocompatibility of biosensors," Biomaterials, vol. 16 (1995), pp. 389-396.

M. Mrksich et al., "Surface Plasmon Resonance Permits in Situ Measurement of Protein Adsorption on Self-Assembled Monolayers of Alkanethiolates on Gold," Langmuir, vol. 11 (1995), pp. 4383-4385.

E. H. Yang et al, "Fabrication and dynamic testing of electrostatic actuators with p+ silicon diaphragms," Sensors and Actuators A, vol. 50 (1995), pp. 151-156.

E. H. Yang et al, "A technique for quantitative determination of the profile of the residual stress along the depth of $p_+$ silicon films," Appl. Phys. Lett., vol. 67 (Aug. 14, 1995), pp. 912-914.

M. Iyer et al., "Accelerated Hybridization of Oligonucleotides to Duplex DNA," The Journal of Biological Chemistry, vol. 270 (Jun. 16, 1995), pp. 14712-14717.

M. Bohlen, "A Halitosis Sensor for the quantitative assessment of oral malodor in humans," Integrated Micro Systems (18-819), Carnegie Mellon University, Fall, 1996, pp. 1-13.

K. R. Williams, et al., "Etch Rates for Micromachining Processing," Journal of Microelectromechnical Systems, vol. 5, No. 4, Dec. 1996, pp. 256-269.

G. M. Kuziemko et al., "Cholera Toxin Binding Affinity and Specificity for Gangliosides Determined by Surface Plasmon Resonance," Biochemistry, vol. 35, 1996, pp. 6375-6384.

S. R. Manalis et al., "Interdigital cantilevers for atomic force microscopy," Applied Physics Letters, vol. 69, No. 25, Dec. 16, 1996, pp. 3944-3946.

M. Mrksich et al., "Using Self-Assembled Monolayers to Understand the Interactions of Man-Made Surfaces with Proteins and Cells," Annu. Rev. Biophys. Biomol. Struct., vol. 25, 1996, pp. 55-78.

K. Nakanishi et al., "A Novel Method of Immobilizing Antibodies on a Quartz Crystal Microbalance Using Plasma-Polymerized Films for Immunosensors," Analytical Chemistry, vol. 68, No. 10, May 15, 1996, pp. 1695-1700.

I. Shalish et al., "Gold metallization for aluminum nitride," Thin Solid Films, vol. 28 (1996), pp. 166-169.

S. Shi-Hui et al., "Bulk acoustic wave sensor for investigation hemorheoloical characteristics of plasma and its coagulation," J. Biochem. Biophys. Methods, vol. 31 (1996), pp. 135-143.

A. Ullman, "Formation and Structure of Self-Assembled Monolayers," Chem. Rev., vol. 96 (1996), pp. 1533-1554.

B. A. Warneke, "Triaxial Monolithic Piezoresistive Accelerometers in Foundry CMOS," Masters Thesis, Electrical Engineering, University of California, Los Angeles, CA (1996).

G. Sigal et al., "A Self-Assembled Monolayer for the Binding and Study of Histidine-Tagged Proteins by Surface Plasmon Resonance," Anal. Chem., vol. 68 (1996), pp. 490-497.

Biosite® Inc. Web Site—Products, products tab, at "http://www.biosite.com/products/default.aspx" (last visited May 24, 2005), p. 1.

Y. Xia et al., "Non-Photolithographic Methods for Fabrication of Elastomeric Stamps for Use in Microcontact Printing," Langmuir, vol. 12 (1996), pp. 4033-4038.

E. T. Zellers et al., "Effects of Temperature and Humidity on the Performance of Polymer-Coated Surface Acoustic Wave Vapor Sensor Arrays," Anal. Chem., vol. 68 (1996), pp. 2409-2418.

P. M. Richalet-Sécordel et al., "Concentration Measurement of Unpurified Proteins Using Biosensor Technology under Conditions of Partial Mass Transport Limitation," Analytical Biochemistry, vol. 249, 1997, pp. 165-173.

A. F. Collings et al., "Biosensors: recent advances," Rep. Prog. Phys., vol. 60, 1997, pp. 1397-1445.

B. A. Čavić et al., "Acoustic waves and the real-time study of biochemical macromolecules at the liquid/solid interface," Faraday Discuss., vol. 107, 1997, pp. 159-176.

L. Christensen, "Theoretical Analysis of Protein Concentration Determination Using Biosensor Technology under Conditions of Partial Mass Transport Limitation," Analytical Biochemistry, vol. 249, 1997, pp. 153-164.

Y. Lvov et al., "Alternate Assembly of Ordered Multilayers of $SiO_2$ and Other Nanoparticles and Polyions," Langmuir, vol. 13, 1997, pp. 6195-6203.

P. Cherukat et al., "A Computational Study of the Inertial Lift on a Sphere in a Linear Shear Flow Field," Department of Chemical Engineering, Clarkson University, Potsdam, NY, Oct. 8, 1997.

N. Patel et al., "Immobilization of Protein Molecules onto Homogeneous and Mixed Carboxylate-Terminated Self-Assembled Monolayers," Langmuir, vol. 13, 1997, pp. 6485-6490.

R. R. Seigel et al., "On-Line Detection of Nonspecific Protein Adsorption at Artificial Surfaces," Analytical Chemistry, vol. 69, No. 16, Aug. 15, 1997, pp. 3321-3328.

M. B. Medina et al., "Real-time analysis of antibody binding interactions with immobilized *E. coli* 0157:H7 cells using the BIAcore," Biotechnology Techniques, vol. 11, No. 3, Mar. 1997, pp. 173-176.

M. Minor et al., "Dynamic Aspects of Electrophoresis and Electroosmosis: A New Fast Method for Measuring Particle Mobilities," Journal of Colloid and Interface Science, vol. 189, (1997), pp. 370-375.

M. Takayasu et al., "Continuous Magnetic Separation of Blood components from Whole Blood," 16th International Conference on Magnet Technology, Florida, USA, 1999.

M. Rodahl et al., "Simultaneous frequency and dissipation factor QCM measurements of biomolecular adsorption and cell adhesion," Faraday Discuss, vol. 107 (1997), pp. 229-246.

S. Sánchez et al., "Spontaneous direct bonding of thick silicon nitride," J. Micromech. Microeng. vol. 7 (1997) pp. 111-113.

X. Wang, "Dielectrophoretic Manipulation of Particles," IEEE Transactions on Industry Applications, vol. 33 (May/Jun. 1997), pp. 660-669.

X. Wang et al., "General expressions for dielectrophoretic force and electrorotational torque derived using the Maxwell stress tensor method," Journal of Electrostatics, vol. 39 (1997), pp. 277-295.

R. M. White, "Introductory Lecture—Acoustic interactions from Faraday's crispations to MEMS," Faraday Discuss, vol. 107 (1997), pp. 1-13.

D. S. Ballantine, Jr. et al., "Acoustic Wave Sensors—*Theory, Design, and Physico-Chemical Applications*," Academic Press, New York, 1997.

H. Yu et al., "Development of a Magnetic Microplate Chemifluorimmunoassay for Rapid Detection of Bacteria and Toxin in Blood," Analytical Biochemistry, vol. 261, 1998, pp. 1-7.

R. C. Anderson et al., "Genetic Analysis Systems: Improvements and Methods," Solid-State Sensor and Actuator Workshop, Hilton Head Island, South Carolina, Jun. 8-11, 1998, pp. 7-10.

D. G. Myszka et al., "Extending the Range of Rate Constants Available from BIACORE: Interpreting Mass Transport-Influenced Binding Data," Biophysical Journal, vol. 75, Aug. 1998, pp. 583-594.

C. Bisson et al., "A Microanalytical Device for the Assessment of Coagulation Parameters in Whole Blood," Solid-State Sensor and Actuator Workshop, Hilton Head Island, South Carolina, Jun. 8-11, 1998, pp. 1-6.

A. S. Blawas et al., "Protein patterning," Biomaterials, vol. 19, 1998, pp. 595-609.

J. D. Brewster, "Automated filtration capture immunoelectrochemical assay of bacteria," Proceedings of SPIE Reprint, Reprinted from Pathogen Detection and Remediation for Safe Eating, Nov. 5, 1998, Boston, MA.

L. D. Burke et al., "The Electrochemistry of Gold: II The Electrocatalytic Behaviour of the Metal in Aqueous Media," Gold Bulletin, vol. 31, No. 2, 1998, pp. 39-50.

J. M. Bustillo et al., "Surface Micromachining for Microelectromechanical Systems," Proceedings of the IEEE, vol. 86, No. 8, Aug. 1998, pp. 1552-1574.

G. M. Cruise et al., "Characterization of permeability and network structure of interfacially photopolymerized poly(ethylene glycol) diacrylate hydrogels," Biomaterials, vol. 19, 1998, pp. 1287-1294.

Y. M. Lvov et al., "High-speed multilayer film assembly by alternate adsorption of silica nanoparticles and linear polycation," Chem. Commun., 1998, pp. 1229-1230.

J. L. Dohner, "The Contribution of Radiation and Viscous Loss in a Fluid Loaded Flexural Plate Wave Sensor," Journal of Sound and Vibration, vol. 217, No. 1, 1998, pp. 113-126.

D. L. Elbert et al., "Self-assembly and steric stabilization at heterogeneous, biological surfaces using adsorbing block copolymers," Chemistry & Biology, vol. 5, Mar. 13, 1998, pp. 177-183.

J. C. Pyun et al., "Development of a biosensor for E. coli based on a flexural plate wave (FPW) transducer," Biosensors & Bioelectronics, vol. 13, 1998, pp. 839-845.

C. Fredriksson et al., "The Piezoelectric Quartz Crystal Mass and Dissipation Sensor: A Means of Studying Cell Adhesion," Langmuir, vol. 14, 1998, pp. 248-251.

J. Fritz et al., "Force-mediated kinetics of single P-selectin/ligand complexes observed by atomic force microscopy," Proc. Natl. Acad. Sci. USA, vol. 95, Oct. 1998, pp. 12283-12288.

J. W. Mellors, "Viral-Load Tests Provide Valuable Answers," Scientific American, vol. 279, Jul. 1998, p. 90.

F. Höök et al., "Energy Dissipation Kinetics for Protein and Antibody-Antigen Adsorption under Shear Oscillation on a Quartz Crystal Microbalance," Langmuir, vol. 14, 1998, pp. 729-734.

J. M. Van Emon et al., "Bioseparation and bioanalytical techniques in environmental monitoring," Journal of Chromatography B, vol. 715, 1998, pp. 211-228.

I. Ladabaum et al., "Surface Micromachined Capacitive Ultrasonic Transducers," IEEE Transactions on Ultrasonics, Ferroelectrics, and Frequency Control, vol. 45, No. 3, May 1998, pp. 678-690.

H. Ron et al., "Self-Assembled Monolayers on Oxidized Metals. 2. Gold Surface Oxidative Pretreatment, Monolayer Properties, and Depression Formation," Langmuir, vol. 14, 1998, pp. 1116-1121.

G. G. Yaralioglu et al., "Analysis and design of an interdigital cantilever as a displacement sensor," Journal of Applied Physics, vol. 83, No. 12, Jun. 15, 1998, pp. 7405-7415.

N. Yazdi et al., "Micromachined Inertial Sensors," Proceedings of the IEEE, vol. 86, No. 8, Aug. 1998, pp. 1640-1659.

P. Creter et al, "A Systems Approach to Specifying a High Reliability, High Quality Thick Film Passive Component for Hybrid, Multi-Ship Module and Surface Mount Applications," reprint from IMPAS, International Symposium of Microelectronics, (Nov. 4, 1998), San Diego, CA.

C. Nguyen, "Micromachining technologies for miniaturized communication devices," Proceedings of SPIE: Micromachining and Microfabrication, Sep. 20-22, 1998, Santa Clara, CA, pp. 24-38.

H. Chou et al., "Disposable Microdevices for DNA Analysis and Cell Sorting," Proc. Solid-State Sensor and Actuator Workshop, Hilton Head, SC (Jun. 8-11, 1998), pp. 11-14.

S. J. Martin et al., "Flexural plate wave resonator excited with Lorentz forces," Journal of Applied Physics, vol. 83, No. 9, (May 1, 1998), p. 4589-4601.

S. Storri et al., "Surface modifications for the development of piezoimmunosensors," Biosensors & Bioelectronics, vol. 13, No. 3-4, 1998, pp. 347-357.

A. W. Wang et al., "A Silicon-based Immunoassay for Detection of Breast Cancer Antigens," Sensors and Actuators B, vol. 49 (1998), pp. 13-21.

Y. Watanabe et al., "Changes in optical transmittance and surface morphology of AlN thin films exposed to atmosphere," Journal of Materials Research, vol. 13 (Oct. 1998), p. 2956-2961.

G. Widmer et al., "A Study of Cryptosporidium parvum Genotypes and Population Structure," Mem. Inst. Oswaldo Cruz, vol. 93 (Sep./Oct. 1998), pp. 685-686.

L. Xiao et al., "Species and Strain-specific Typing of C ryptosporidium Parasites in Clinical and Environmental Samples," Mem. Inst. Oswaldo Cruz, vol. 93 (Sep./Oct. 1998), pp. 687-692.

E. T. Zellers et al., "Establishing a Limit of Recognition for a Vapor Sensor Array," Anal. Chem., vol. 70 (1998), pp. 4191-4201.

C. Zhou et al., "Acoustic standing-wave enhancement of a fiber-optic Salmonella biosensor," Biosensors & Bioelectronics, vol. 13 (1998), pp. 495-500.

M. J. Feldstein et al., "Array Biosensor: Optical and Fluidics Systems," Journal of Biomedical Microdevices, vol. 1, No. 2, 1999, pp. 139-153.

K. Andersson et al., "Identification and Optimization of Regeneration Conditions for Affinity-Based Biosensor Assays. A Multivariate Cocktail Approach," Analytical Chemistry, vol. 71, No. 13, Jul. 1, 1999, pp. 2475-2481.

T. E. Fisher et al., "The study of protein mechanics with the atomic force microscope," TIBS, vol. 24, Oct. 1999, pp. 379-384.

R. J. Shul et al., "Group-III Nitride Etch Selectivity in $BCl_3/Cl_2$ ICP Plasmas," MRS Internet J. Nitride Semicond. Res. 4S1, G8.1, 1999.

R. A. Vijayendran et al., "A Computational Reaction-Diffusion Model for the Analysis of Transport-Limited Kinetics," Analytical Chemistry, vol. 71, No. 23, Dec. 1, 1999, pp. 5405-5412.

R. A. Scott et al., "Highly crosslinked, PEG-containing copolymers for sustained solute delivery," Biomaterials, vol. 20, 1999, pp. 1371-1380.

H. Weetall, "Chemical sensors and biosensors, update, what, where, when and how," Biosensors & Bioelectronics, vol. 14, 1999, pp. 237-242.

Cho et al., "Inductively Coupled Plasma Etching of III-Nitrides in $Cl_2/Xe$, $Cl_2/Ar$ and $Cl_2/He$," MRS Internet J. Nitride Semicond. Res. 4S1, G6.56, 1999.

S. E. Cowan et al., "Ultrasonic Flexural-Plate-Wave Sensor for Detecting the Concentration of Settling E. coli W3110 Cells," Analytical Chemistry, vol. 71, No. 16, Aug. 15, 1999, pp. 3622-3625.

R. Ekins et al, "Microarrays: their origins and applications," Tibtech, vol. 17, Jun. 1999, pp. 217-218.

C. Yan et al., "Formation of Alkanethiolate Self-Assembled Monolayers on Oxidized Gold Surfaces," Langmuir, vol. 15, 1999, pp. 2414-2419.

A. Halperin, "Polymer Brushes that Resist Adsorption of Model Proteins: Design Parameters," Langmuir, vol. 15, 1999, pp. 2525-2533.

B. Heymann et al, "Elastic properties of poly(ethylene-glycol) studied by molecular dynamics stretching simulations," Chemical Physics Letters, vol. 307, 1999, pp. 425-432.

R. Hözel, "Non-invasive determination of bacterial single cell properties by electrorotation," Biochimica et Biophysica Acta, vol. 1450, 1999, pp. 53-60.

N. A. Peppas et al., "Poly(ethylene glycol)-containing hydrogels in drug delivery," Journal of Controlled Release, vol. 62, 1999, pp. 81-87.

G. J. Kluth et al., "Direct observation of sulfur dimmers in alkanethiol self-assembled monolayers on Au(111)," Physical Review B, Rapid Communications, vol. 59, No. 16, Apr. 15, 1999, pp. R10 449-R10 452.

R. Lucklum et al., "Role of Mass Accumulation and Viscoelastic Film Properties for the Response of Acoustic-Wave-Based Chemical Sensors," Analytical Chemistry, vol. 71, No. 13, Jul. 1, 1999, pp. 2488-2496.

S. W. Metzger et al., "Development and characterization of surface chemistries for microfabricated biosensors," J. Vac. Sci. Technol. A, vol. 17, No. 5, Sep./Oct. 1999, pp. 2623-2628.

D. Ivnitski et al., "Biosensors for detection of pathogenic bacteria," Biosensors & Bioelectronics, vol. 14, 1999, pp. 599-624.

F. Oesterhelt et al., "Single molecule force spectroscopy by AFM indicates helical structure of poly(ethylene-glycol) in water," New Journal of Physics, vol. 1, 1999, pp. 6.1-6.11.

D. M. Olive et al., "Principles and Applications of Methods for DNA-Based Typing of Microbial Organisms," Journal of Clinical Microbiology, vol. 37, (Jun. 1999), pp. 1661-1669.

S. Kim et al., "The Fabrication of Thin-Film Bulk Acoustic Wave Resonators Employing a ZNO/Si Composite Diaphragm Structure Using Porous Silicon Layer Etching," IEEE Electron Device Letters, vol. 20 (Mar. 1999), p. 113-115.

B. D. Spangler et al., "Capture agents for a quartz crystal microbalance-continuous flow biosensor: functionalized self-assembled monolayers on gold," Analytica Chimica Acta, vol. 399 (1999), pp. 51-62.

T. Strunz et al., "Dynamic force spectroscopy of single DNA molecules," Proc. Natl. Acad. Sci., vol. 96 (Sep. 1999), pp. 11277-11282.

M. V. Voinova et al., "Viscoelastic Acoustic Response of Layered Polymer Films at Fluid-Solid Interfaces: Continuum Mechanics Approach," Physica Scripta, vol. 59 (1999), pp. 391-396.

J. Yang et al., "Cell Separation on Microfabricated Electrodes Using Dielectrophoretic/Gravitational Field-Flow Fractionation," Anal. Chem., vol. 71 (1999), pp. 911-918.

G. L. Kenausis et al., "Poly(L-lysine)-g-Poly(ethylene glycol) Layers on Metal Oxide Surfaces: Attachment Mechanism and Effects of Polymer Architecture on Resistance to Protein Adsorption," J. Phys. Chem. B, vol. 104, 2000, pp. 3298-3309.

G. Bitko et al., "Improving the MEMS Pressure Sensor," Sensors Magazine, Jul. 2000.

C. A. Rowe-Taitt et al., "Simultaneous detection of six biohazardous agents using a planar waveguide array biosensor," Biosensors & Bioelectronics, vol. 15, 2000, pp. 579-589.

C. A. Rowe-Taitt et al., "Array biosensor for detection of biohazards," Biosensors & Bioelectronics, vol. 14, 2000, pp. 785-794.

R. Maboudian et al., "Self-assembled monolayers as anti-stiction coatings for MEMS: characteristics and recent developments," Sensors and Actuators, vol. 82, 2000, pp. 219-223.

R. L. Edelstein et al., "The BARC biosensor applied to the detection of biological warfare agents," Biosensors & Bioelectronics, vol. 14, 2000, pp. 805-813.

H. Brenner et al., "Molecular wall effects: Are conditions at a boundary 'boundary conditions'?," Physical Review E, vol. 61, No. 6, Jun. 2000, pp. 6879-6897.

H. Brenner et al., "Erratum: Molecular wall effects: Are conditions at a boundary 'boundary conditions?'" Physical Review E, vol. 62, No. 5, Nov. 2000, p. 7547.

B. A. Cavic et al., "Adsorptions of Plasma Proteins and Their Elutabilities from a Polysiloxane Surface Studied by an On-Line Acoustic Wave Sensor," Analytical Chemistry, vol. 72, No. 7, Apr. 1, 2000, pp. 1523-1531.

T. Viitala et al., "Protein Immobilization to a Partially Cross-Linked Organic Monolayer," Langmuir, vol. 16, 2000, pp. 4953-4961.

Z. J. Davis et al., "Fabrication and characterization of nanoresonating devices for mass detection," J. Vac. Sci. Technol. B, vol. 18, No. 2, Mar./Apr. 2000, pp. 612-616.

R. D. Deegan et al., "Contact line deposits in an evaporating drop," Physical Review E, vol. 62, No. 1, Jul. 2000, pp. 756-765.

N. Einerson, "Poly(ethylene glycol) and its Role in Surface Modification of Biomaterials," BME/Pharmacy 601, Apr. 2000.

A. E. Herr et al., "Electroosmotic Capillary Flow with Nonuniform Zeta Potential," Analytical Chemistry, vol. 72, No. 5, Mar. 1, 2000, pp. 1053-1057.

Panholzer et al., "FeRAMs—Stars of ISIF 2000," Ferroelectricity Newsletter, Vol. 8, No. 3, Summer 2000, published by the Naval Postgraduate School, Space Systems Academic Group, Monterey, CA, pp. 1-36.

A. Janshoff et al., "Piezoelectric Mass-Sensing Devices as Biosensors—An Alternative to Optical Biosensors?," Angew. Chem. Int. Ed., vol. 39, 2000, pp. 4004-4032.

F. Kienberger et al., "Static and Dynamical Properties of Single Poly(Ethylene Glycol) Molecules Investigated by Force Spectroscopy," Single Molecules, vol. 1, 2000, pp. 123-128.

J. T. Woodward et al., "Effect of an Oxidized Gold Substrate on Alkanethiol Self-Assembly," Langmuir, vol. 16, 2000, pp. 5347-5353.

J. S. Rossier et al., "Characterization of Protein Adsorption and Immunosorption Kinetics in Photoablated Polymer Microchannels," Langmuir, vol. 16, 2000, pp. 8489-8494.

E. B. Cooper et al., "High-resolution micromachined interferometric accelerometer," Applied Physics Letters, vol. 76, No. 22, May 29, 2000, pp. 3316-3318.

N. Nguyen et al., "Acoustic Streaming in Micromachined Flexural Plate Wave Devices: Numerical Simulation and Experimental Verification," IEEE Transactions on Ultrasonics, Ferroelectrics, and Frequency Control, vol. 47, No. 6, Nov. 2000, pp. 1463-1471.

J. Choi et al., "A new magnetic bead-based, filterless bio-separator with planar electromagnet surfaces for integrated bio-detection systems," Sensors and Actuators B, vol. 68, 2000, pp. 34-39.

S. T. Pathirana et al, "Rapid and sensitive biosensor for *Salmonella*," Biosensors and Bioelectronics, vol. 15 (2000), pp. 135-141.

Boston MicroSystems—Fluid Sensors, fluid sensors tab, at "http://www.bostonmicrosytems.com/fluidsensors.shtml" (last visited May 25, 2005), pp. 1-3.

K. Rogers, "Principles of Affinity-Based Biosensors," Molecular Biotechnology, vol. 14 (2000), pp. 109-129.

S. Quake et al., "From Micro-to Nanofabrication with Soft Materials," Science, vol. 290 (Nov. 24, 2000), pp. 1536-1540.

F. N. Dulsev et al., "'Hearing' Bond Breakage. Measurement of Bond Rupture Forces Using a Quartz Crystal Microbalance," Langmuir, vol. 16 (2000), pp. 5036-5040.

T. Sulchek et al., "High-speed atomic force microscopy in liquid," Review of Scientific Instruments, vol. 71 (May 2000), pp. 2097-2099.

U. Seifert, "Rupture of Multiple Parallel Molecular bonds under Dynamic Loading," Physical Review Letters, vol. 84 (Mar. 20, 2000) pp. 2750-2753.

T. P. Vinkinge et al., "Comparison of surface plasmon resonance and quartz crystal microbalance in the study of whole blood and plasma coagulation," Biosensors & Bioelectronics, vol. 15 (2000), pp. 605-613.

M. S. Weinberg et al., "Modeling Flexural Plate Wave Devices," Journal of Microelectromechanical Systems, vol. 9 (Sep. 2000), pp. 370-379.

N. D. Winblade, "Blocking Adhesion to Cell and Tissue Surfaces via Steric Stabilization with Graft Copolymers containing Poly(Ethylene Glycol) and Phenylboronic Acid," thesis in partial fulfillment of the requirements for the degree of Doctor of Philosophy, C.I.T., Pasadena, CA (defended Oct. 23, 2000).

J. W. Grate et al., "The Fractional Free Volume of the Sorbed Vapor in Modeling the Viscoelastic Contribution to Polymer-Coated Surface Acoustic Wave Vapor Sensor Reponses," Anal. Chem., vol. 72 (2000), pp. 2861-2868.

K. F. Jensen, "Microreaction engineering—is small better?," Chemical Engineering Science, vol. 56, 2001, pp. 293-303.

N. D. Masters et al., "Side-by-Side Comparison of Passive MEMS Strain Test Structures under Residual Compression," Mechanical Properties of Structural Films, Sep. 15, 2001, pp. 1-33.

M. Abrantes et al., "Adaptation of a Surface Plasmon Resonance Biosensor with Microfluidics for Use with Small Sample Volumes and Long Contact Times," Analytical Chemistry, vol. 73, No. 13, Jul. 1, 2001, pp. 2828-2835.

M. Johnson, "High Sensitivity Magnetic Sensors for Biotechnology," DARPA Workshop on Bio-Magnetic Interfacing Concepts, Arlington, VA, Dec. 12, 2001.

L. Whitman et al., "A Micromagnetic Gene Chip: Magnetic Labeling and GMR Detection of DNA," BioMagnetICs Workshop, Dec. 12, 2001.

D. P. Chandler et al., "Automated immunomagnetic separation and microarray detection of *E. Coli* 0157:H7 from poultry carcass rinse," International Journal of Food Microbiology, vol. 70, 2001, pp. 143-154.

J. Choi et al., "Development and Characterization of Microfluidic Devices and Systems for Magnetic Bead-Based Biochemical Detection," Biomedical Microdevices, vol. 3, No. 3, 2001, pp. 191-200.

A. N. Cleland et al., "Single-crystal aluminum nitride nanomechanical resonators," Applied Physics Letters, vol. 79, No. 13, Sept. 24, 2001, pp. 2070-2072.

C. L. Baird et al., "Current and emerging commercial optical biosensors," Journal of Molecular Recognition, vol. 14, 2001, pp. 261-268.

M. A. Cooper et al., "Direct and sensitive detection of a human virus by rupture event scanning," Nature Biotechnology, vol. 19, Sep. 2001, pp. 833-837.

B. Cunningham et al., "Design, fabrication and vapor characterization of a microfabricated flexural plate resonator sensor and application to integrated sensor arrays," Sensors and Actuators B, vol. 73, 2001, pp. 112-123.

D. Figueredo et al., "Film Bulk Acoustic Resonator Technology & Wireless Applications," Berkeley Wireless Research Center Retreat, Jan. 8, 2001, pp. 1-25.

J. M. Dodson et al., "Fluidics Cube for Biosensor Miniaturization," Analytical Chemistry, vol. 73, No. 15, Aug. 1, 2001, pp. 3776-3780.

E. Evans, "Probing the Relation Between Force-Lifetime-And Chemistry In Single Molecular Bonds," Annu. Rev. Biophys. Biomol. Struct., vol. 30, 2001, pp. 105-128.

A. H. Forster et al., "A laminated, flex structure for electronic transport and hybridization of DNA," Biosensors & Bioelectronics, vol. 16, 2001, pp. 187-194.

Y. S. Fung et al., "Self-Assembled Monolayers as the Coating in a Quartz Piezoelectric Crystal Immunosensor To Detect *Salmonella* in Aqueous Solution," Analytical Chemistry, vol. 73, No. 21, Nov. 1, 2001, pp. 5302-5309.

D. S. Wilson, et al. "Functional protein microarrays," Current Opinion in Chemical Biology, vol. 6, 2001, pp. 81-85.

P. Galambos et al., "Precision Alignment Packaging for Microsystems with Multiple Fluid Connections," Proceeding of 2001 ASME: International Mechanical Engineering Conference and Exposition, Nov. 11-16, 2001, New York, NY, pp. 1-8.

G. P. Hatch et al., "Magnetic design considerations for devices and particles used for biological high-gradient magnetic separation (HGMS) systems," Journal of Magnetism and Magnetic Materials, vol. 225, 2001 pp. 262-276.

F. Höök et al., "Variations in Coupled Water, Viscoelastic Properties, and Film Thickness of a Mefp-1 Protein Film during Adsorption and Cross-Linking: A Quartz Crystal Microbalance with Dissipation Monitoring, Ellipsometry, and Surface Plasmon Resonance Study," Analytical Chemistry, vol. 73, No. 24, Dec. 15, 2001, pp. 5796-5804.

E. J. Houser et al., "Rational materials design of sorbent coatings for explosives: applications with chemical sensors," Talanta, vol. 54, 2001, pp. 469-485.

N. Huang et al., "Poly(L-lysine)-g-poly(ethylene glycol) Layers on Metal Oxide Surfaces: Surface-Analytical Characterization and Resistance to Serum and Fibrinogen Adsorption," Langmuir, vol. 17, 2001, pp. 489-498.

S. Sakiyama-Elbert et al., "Functional Biomaterials: Design of Novel Biomaterials," Annu. Rev. Mater. Res., vol. 31, 2001, pp. 183-201.

P. B. Luppa et al., "Immunosensors-principles and applications to clinical chemistry," Clinica Chimica Acta, vol. 314, 2001, pp. 1-26.

M. Ishihara et al., "Synthesis and Surface Acoustic Wave Property of Aluminum Nitride Thin Films Fabricated on Silicon and Diamond Substrates Using the Sputtering Methods," Jpn. J. Appl. Phys., vol. 40, 2001, pp. 5065-5068.

M. K. Jain et al., "Measurement of Temperature and Liquid Viscosity Using Wireless Magneto-Acoustic/Magneto-Optical Sensors," IEEE Transactions on Magnetics, vol. 37, No. 4, Jul. 2001 pp. 2767-2769.

Z. Liu et al., "Low-Temperature Air-Fireable Glass-Free Metallic Thick-Film Electrical Conductor Materials," Journal of Electronic Materials, vol. 30, No. 11, 2001, p. 1458.

K. Kao et al., "Synthesis of C-Axis-Oriented Aluminum Nitride Films by Reactive RF Magnetron Sputtering for Surface Acoustic Wave," Jpn. J. Appl. Phys., vol. 40, 2001, pp. 4969-4973.

K. E. Sapsford et al., "Kinetics of Antigen Binding to Arrays of Antibodies in Different Sized Spots," Analytical Chemistry, vol. 73, No. 22, Nov. 15, 2001, pp. 5518-5524.

V. Kaajakari et al., "A Frequency Addressable Ultrasonic Microfluidic Actuator Array," Transducers '01, Eurosensors XV, The 11th International Conference on Solid-State Sensors and Actuators, Munich, Germany, Jun. 10-14, 2001.

S. Perez-Amodio et al., "Effects on the Ionic Environment, Charge, and Particle Surface Chemistry for Enhancing a Latex Homogeneous Immunoassay of C-Reactive Protein," Analytical Chemistry, vol. 73, No. 14, Jul. 15, 2001, pp. 3417-3425.

V. Linder et al., "Surface Biopassivation of Replicated Poly(dimethylsiloxane) Microfluidic Channels and Applications to Heterogeneous Immunoreaction with On-Chip Fluorescence Detection," Analytical Chemistry, vol. 73, No. 17, Sep. 1, 2001, pp. 4181-4189.

Y. Liu et al., "Microfabricated Polycarbonate CE Devices for DNA Analysis," Analytical Chemistry, vol. 73, No. 17, Sep. 1, 2001, pp. 4196-4201.

K. Martin et al., "Measurement of the Speed of Sound in Ethanol/Water Mixtures," Ultrasound in Medicine & Biology., vol. 27, No. 2, 2001, pp. 289-291.

T. J. Moir, "Discrete-time Variance Tracking with Application to Speech Processing," Res. Lett. Inf. Math. Sci., vol. 2, 2001, pp. 71-80.

H. Tsai et al., "A Strategy for Multi-Protein-Immobilization Using N-succinimidyl 4-Benzoylbenzoic Acid as the Photolabile Ligand," Analytical Sciences (Supplement), vol. 17, 2001, pp. i269-i272.

C. J. Percival et al., "Molecular-Imprinted, Polymer-Coated Quartz Crystal Microbalances for the Detection of Terpenes," Anal. Chem, vol. 73, (2001), pp. 4225-4228.

F. Höök et al., Characterization of PNA and DNA Immobilization and Subsequent Hybridization with DNA Using Acoustic-Shear-Wave Attenuation Measurements, Langmuir, vol. 17 (2001), pp. 8305-8312.

J. Halámek et al., "Investigation of highly sensitive piezoelectric immunosensors for 2,4-dichlorophenoxyacetic acid," Biosensors & Bioelectronics, vol. 16 (2001), pp. 253-260.

A. J. Madonna et al., "Detection of bacterial from biological mixtures using immunomagnetic separation combined with matrix-assisted laser desorption/ionization time-of-flight mass spectrometry," Rapid Communications in Mass Spectrometry, vol. 15 (2001), pp. 1068-1074.

F. N. Dultsev et al., "Direct and Quantitative Detection of Bacteriophase by "Hearing" Surface Detachment Using a Quartz Crystal Microbalance," Analytical Chemistry, vol. 73 (2001), pp. 3935-3939.

E. O. Saphire et al., "Listening for viral infection," Nature Biotechnology, vol. 19 (Sep. 2001), p. 283-284.

J. Freudenberg et al., "A Saw immunosensor for operation in liquid using a $SiO_2$ protective layer," Sensors and Actuators B, vol. 76 (2001), pp. 147-151.

J. D. Snyder et al., "Fabrication of Multiple Microscale Features on Polymer Surfaces for Applications in Tissue Engineering," Biomedical Microdevices, vol. 3 (2001), pp. 293-300.

S. Solé, "New materials for electrochemical sensing III. Beads," Trends in Analytical Chemistry, vol. 20 (2001), pp. 102-110.

B. D. Spangler et al., "Comparison of the Speeta® surface plasmon resonance sensor and a quartz crystal microbalance for detection of *Escherichia coli* heat-labile enterotoxin," Analytica Chimica Acta, vol. 444 (2001), pp. 149-161.

S. A. McAuley et al., "Silicon micromachining using a high-density plasma source," J. Phys. D: Appl. Phys., vol. 34 (2001), pp. 2769-2774.

G. Eiceman et al., "Preface," Talanta, vol. 54 (2001), pp. 425-426.

K. M. Lakin, "Thin Film Resonators and High Frequency Filters," TFR Technologies, Inc., (Jun. 1, 2001), pp. 1-18.

M. Tsai et al., "Preconditioning gold Substrates Influences Organothiol Self-assembled Monolayer (SAM) Formation," Journal of Colloid and Interface Science, vol. 238 (2001), pp. 259-266.

J. Voldman, "A microfabricated dielectrophoretic trapping array for cell-based biological assays," Ph.D. Thesis, Department of Electrical Engineering and Computer Science, M.I.T., Cambridge, MA, Jun. 2001.

B. Zhu et al., "Chain-length dependence of the protein and cell resistance of oligo(ethylene glycol)-terminated self-assembled monolayers on gold," Department of Chemical Engineering, University of Illinois at Urbana-Champaign, Urbana, IL/Department of Veterinary Biosciences, University of Illinois at urbana-Champaign, Urbana, IL (accepted Mar. 10, 2001), John Wiley & Sons, Inc., 2001, pp. 406-416.

L. A. Ruiz-Taylor, "Monolayers of derivatized poly($_L$-lysine)-grafted poly(ethylene glycol) on metal oxides as a class of biomolecular interfaces," PNAS, vol. 98 (Jan. 30, 2001), pp. 852-857.

K. Hutchinson et al., "Explosives-related chemical concentrations in surface soils over buried land mines," Proceedings of the SPIE: Detection and Remediation Technologies for Mines and Minelike Targets VII, vol. 4742, 2002, pp. 544-549.

P. Irwin et al., "Immuno-Magnetic Bead Mass Transport and Capture Efficiency at Low Target Cell Densities in Phosphate-Buffered Saline," Journal of Rapid Methods and Automation in Microbiology, vol. 10, 2002, pp. 129-147.

Janossy et al., "Affordable $CD4^+$-T-Cell Counting by Flow Cytometry: CD45 Gating for Volumetric Analysis," Clinical and Diagnostic Laboratory Immunology, vol. 9, No. 5, Sep. 2002, pp. 1085-1094.

S. P. Lal et al., "Antibody arrays: an embryonic but rapidly growing technology," Drug Discovery Today, vol. 7, No. 18 (Suppl.), 2002, pp. S143-S149.

C. Dames et al., "Optically Sensed In-Plane AFM Tip with On-Board Actuator," Final Report for 6.777 Design and Fabrication of Microelectromechanical Devices, May 17, 2002, pp. 1-72.

J. P. Black et al., "Microsphere Capture and Perfusion in Microchannels Using Flexural Plate Wave Structures," 2002 IEEE Ultrasonics Symposium, 2002, pp. 475-479.

M. O. Scully et al., "Fast Cars: Engineering a Laser Spectroscopic Technique for Rapid Identification of Bacterial Spores," Institute for Quantum Studies, Dept. of Physics, Texas A&M University, College Station, TX, May 2, 2002.

N. K. Chaki et al., "Self-assembled monolayers as a tunable platform for biosensor applications," Biosensors & Bioelectronics, vol. 17, 2002, pp. 1-12.

C. L. DiGiorgio et al., "Cryptosporidium and Giardia Recovers in Natural Waters by Using Environmental Protection Agency Method 1623," Applied and Environmental Microbiology, vol. 68, No. 12, Dec. 2002, pp. 5952-5955.

P. S. Doyle et al., "Self-Assembled Magnetic Matrices for DNA Separation Chips," Science, vol. 295, Mar. 22, 2002, p. 2237.

J. W. McClaine et al., "Characterizing the Adhesion of Motile and Nonmotile *Escherichia coli* to a Glass Surface Using a Parallel-Plate Flow Chamber," Biotechnology and Bioengineering, vol. 78, No. 2, Apr. 20, 2002, pp. 179-189.

O. Hofmann et al., "Three-Dimensional Microfluidic Confinement for Efficient Sample Delivery to Biosensor Surfaces. Application to Immunoassays on Planar Optical Waveguides," Analytical Chemistry, vol. 74, No. 20, Oct. 15, 2002, pp. 5243-5250.

T. Nishihara et al., "High Performance and Miniature Thin Film Bulk Acoustic Wave filters for 5 GHz," 2002 IEEE Ultrasonics Symposium, 2002.

S. Tokumitsu et al., "Grafting of Alkanethiol-Terminated Poly(ethylene glycol) on Gold," Langmuir, vol. 18, 2002, pp. 8862-8870.

E. F. Hasselbrink, Jr., et al., "High-Pressure Microfluidic Control in Lab-on-a-Chip Devices Using Mobile Polymer Monoliths," Analytical Chemistry, vol. 74, No. 19, Oct. 1, 2002, pp. 4913-4918.

F. S. Ligler et al., "Integrating Waveguide Biosensor," Analytical Chemistry, vol. 74, No. 3, Feb. 1, 2002, pp. 713-719.

C. R. Tamanaha et al., "Hybrid macro-micro fluidics system for a chip-based biosensor," Journal of Micromechanics and Microengineering, vol. 12, 2002, pp. N7-N17.

C. A. Savran et al., "Fabrication and Characterization of a Micromechanical Sensor for Differential Detection of Nanoscale Motions," Journal of Microelectromechanical Systems, vol. 11, No. 6, Dec. 2002, pp. 703-708.

T. Moir et al., "A Kepstrum approach to Filtering, Smoothing and Prediction," Res. Lett. Inf. Math. Sci., vol. 3, (2002), pp. 135-147, Auckland, New Zealand.

"MEMS mean business," www.optomem.eu.com, (Winter 2002), pp. 23, 25.

M. A. Cooper, "Optical Biosensors in Drug Discovery," Nature Reviews, vol. 1, Jul. 2002, p. 515-528.

S. M. Briglin et al., "Exploitation of spatiotemporal information and geometric optimization of signal/noise performance using arrays of carbon black-polymer composite vapor detectors," Sensors and Actuators B, vol. 82, 2002, pp. 54-74.

P. J. Rodacy et al., "The Training and Deployment of Honeybees to Detect Explosives and other Agents of Harm," Detection and Remediation Technologies for Mines and Minelike Targets VII, Proceedings of SPIE, vol. 4742, pp. 474-481, 2002.

F. Engelmark, "AIN and High-k Thin Films for IC and Electroacoustic Applications," Comprehensive Summaries of Uppsala Dissertations from the Faculty of Science and Technology, vol. 757, ACTA Universitatis Upsaliensis, Uppsala, 2002.

M. V. Voinova et al., "'Missing mass' effect in biosensor's QCM applications," Biosensors & Bioelectronics, vol. 17 (2002), pp. 835-841.

A. G. Rand et al., "Optical Biosensors for Food Pathogen Detection," FoodTechnology, vol. 56 (Mar. 2002) pp. 32-39.

R. Hall, "Biosensor technologies for detecting microbiological foodborne hazards," Microbes and Infection, vol. 4 (2002), pp. 425-432.

Y. Loo et al., "Soft, conformable electrical contacts for organic semiconductors: High-resolution plastic circuits by lamination," PNAS, vol. 99 (Aug. 6, 2002), pp. 10252-10256.

J. Rossier et al., "Polymer microfluidic chips for electrochemical and biochemical analyses," Electrophoresis, vol. 23 (2002), pp. 858-867.

Matocha et al., "Positive flatband voltage shift in MOS capacitors on n-type GaN," IEEE Electron Device Letters, vol. 23, No. 2, Feb. 2002, p. 79-81.

R. Knobel et al., "Piezoelectric Displacement Sensing with a Single Transistor," Department of Physics and iQUEST, University of California at Santa Barbara, Santa Barbara, CA (May 24, 2002).

S. Sharma et al., "Controlling Nonspecific Protein Interactions in Silicon Biomicrosystems with Nanostructured Poly(ethylene glycol) Films," Langmuir, vol. 18 (2002), pp. 8728-8731.

A. D. Stroock et al., "Chaotic Mixer for Microchannels," Science, vol. 295 (Jan. 25, 2002), pp. 647-651.

F. Mandy et al., "T-Cell Subset Counting and the Fight Against AIDS: Reflections Over a 20-Year Struggle," Cytometry (Clinical Cytometry), vol. 50 (2002), pp. 39-45.

D. Trebotich et al., "Complex Fluid Dynamics in BioMEMS Devices: Modeling of Microfabricated Microneedles," Modeling and Simulation of Microsystems, (2002), pp. 10-13.

D. Zhuang et al., "Wet Chemical Etching of AIN Single Crystals," MRS Internet Journal Nitride Semiconductor Research, vol. 7 (2002), pp. 1-6.

M. Dimitrov et al., "Hydrogels based on the chemically crosslinked polyacrylic acid: Biopharmaceutical characterization," Acta Pharm., vol. 53, 2003 pp. 25-31.

D. Zhang et al, "Synthesis and Single Molecule Force Spectroscopy of Graft Copolymers of Poly (2-hydroxyethyl methacrylate-g-ethylene glycol)," Department of Materials Science and Engineering, Massachusetts Institute of Technology, Cambridge, MA, Jul. 2003, pp. 1-47.

G.W. Ritter, "Using Adhesives Effectively in Medical Devices," available at "http://www.devicelink.com/grabber.php3?URL=http://www.devicelink.com/mddi/archive/..." downloaded Aug. 13, 2003, 7 pages.

L. Ceriotti, "Microfluidic systems for point-of-care testing," Sensors, Actuators and Microsystems Laboratory Institute of Microtechnology, University of Neuchâtel, Neuchâtel, Switzerland, May 21, 2003.

M. Cooper, "Biosensing using rupture event scanning (REVS)™," Measurement Science and Technology, vol. 14, 2003, pp. 1888-1893.

J. Yinon, "Detection of Explosives by Electronic Noses," Analytical Chemistry, Mar. 1, 2003, pp. 99-105.

S. D. Richardson, "Water Analysis: Emerging Contaminants and Current Issues," Analytical Chemistry, vol. 75, No. 12, Jun. 15, 2003, pp. 2831-2857.

R. Grace, "Commercialization Issues of MEMS/MST/Micromachines An Updated Industry Report Card On The Barriers To Commercialization," http://www.rgrace.com/Papers/commercial.html, downloaded Jan. 16, 2003.

J. W. Grate, "A Sorptive Behavior of Monolayer-Protected Gold Nanoparticle Films Containing Alkanethiols and Alkanedithiols," Analytical Chemistry, vol. 75, No. 23, Dec. 1, 2003, p. 6759.

J. Z. Hilt et al., "Ultrasensitive Biomems Sensors Based on Microcantilevers Patterned with Environmentally Responsive Hydrogels," Biomedical Microdevices, vol. 5, No. 3, 2003, pp. 177-184.

D. Sparks et al., "Measurement of density and chemical concentration using a microfluidic chip," Lab Chip, vol. 3, 2003, pp. 19-21.

K. Williams, et al., "Etch Rates for Micromachining Processing—Part II," Journal of Microelectromechanical Systems, vol. 12, No. 6, Dec. 2003, pp. 761-778.

J. Lahann et al., "Reactive Polymer Coatings: A First Step toward Surface Engineering of Microfluidic Devices," Analytical Chemistry, vol. 75, No. 9, May 1, 2003, pp. 2117-2122.

J. Voldman et al., "Design and analysis of extruded quadrupolar dielectrophoretic traps," Journal of Electrostatics, vol. 57, 2003 pp. 69-90.

G. Kim et al., "Impedance characterization of a piezoelectric immunosensor Part I: Antibody coating and buffer solution," Biosensors and Bioelectronics, vol. 18, 2003, pp. 83-89.

G. Kim et al., "Impedance characterization of a piezoelectric immunosensor Part II: *Salmonella* typhimurium detection using magnetic enhancement," Biosensors and Bioelectronics, vol. 18, 2003, pp. 91-99.

G. Lettieri et al., "A novel microfluidic concept for bioanalysis using freely moving beads trapped in recirculating flows," Lab Chip, vol. 3, 2003, pp. 34-39.

T. P. Burg et al., "Suspended microchannel resonators for biomolecular detection," Applied Physics Letters, vol. 83, No. 13, Sep. 29, 2003, pp. 2698-2700.

A. Piqué et al., "Laser processing of polymer thin films for chemical sensor applications," Surface and Coatings Technology, vol. 163-164, 2003, pp. 293-299.

E. V. Olsen et al., "Specific and selective biosensor for *Salmonella* and its detection in the environment," Journal of Microbiological Methods, vol. 53, 2003, pp. 273-285.

M. Kanai et al., "PDMS Microfluidic Devices with PTFE Passivated Channels," 7th International Conference on Miniaturized Chemical and Biochemical Analysis Systems (Oct. 5-9, 2003), p. 429-432.

L. Puckett et al., "Monitoring blood coagulation with magnetoeleastic sensors," Biosensors and Bioelectronics, vol. 18 (2003), pp. 675-681.

C. A. Savran et al., "Microfabricated mechanical biosensor with inherently differential readout," Applied Physics Letters, vol. 83 (2003), pp. 1659-1661.

B. Chadwick et al., "Selecting the Right Material for Medical Seals," Medical Device & Diagnostic Industry Magazine, http:/www.devicelink.com/grabber.php3?URL=htt;://www.devicelink.com/mddi/archive/... (last visited Aug. 13, 2003).

W. C. Tang, "Micro-Biomechanics," University of California Irvine, Department of Biomedical Engineering/Department of Electrical Engineering & Computer Science, (Sep. 2003).

H. Su et al., "Kinetics of interfacial nucleic acid hybridization studied by acoustic network analysis," Biosensors & Bioelectronics, vol. 10, 1995, p. 329-340.

J. N. Lee et al., "Solvent Compatibility of Poly(dimethylsiloxane)-Based Microfluidic Devices," Anal. Chem., vol. 75 (2003), pp. 6544-6554.

X. J. Zhang et al., "Integrated Optical Diffractive Micrograting-Based Injection Force Sensor," IEEE, The 12th International conference on Solid State Sensors, Actuators and Microsystems, Boston, MA (Jun. 8-12, 2003), pp. 1051-1054.

P. Irwin et al., "Blocking nonspecific adsorption of native food-borne microorganisms by immunomagnetic beads with 1-carrageenan," Carbohydrate Research, vol. 339, 2004, pp. 613-621.

I. L. Medintz et al., "General Strategy for Biosensor Design and Construction Employing Multifunctional Surface-Tethered Components," Analytical Chemistry, vol. 76, No. 19, Oct. 1, 2004, pp. 5620-5629.

C. H. Ahn et al., "Disposable Smart Lab on a Chip for Point-of-Care Clinical Diagnostics," Proceedings of the IEEE, vol. 92, No. 1, Jan. 2004, pp. 154-173.

R. H. Liu et al., "Self-Contained, Fully Integrated Biochip for Sample Preparation, Polymerase Chain Reaction Amplification, and DNA Microarray Detection," Analytical Chemistry, vol. 76, No. 7, Apr. 1, 2004, pp. 1824-1831.

M. Andersson et al., "Quartz crystal microbalance-with dissipation monitoring (QCM-D) for real time measurements of blood coagulation density and immune complement activation on artificial surfaces," Biosensors & Bioelectronics, vol. 21, 2004, pp. 79-86.

D. Carter et al., "Fabrication and Measurement of an IC-Compatible GHZ-Range Piezoelectric Longitudinal Bar Resonator," Solid-State Sensor, Actuator and Microsystems Workshop, Hilton Head Island, South Carolina, Jun. 6-10, 2004, pp. 254-257.

V. Craig, "Bubble coalescence and specific-ion effects," Current Opinion in Colloid and Interface Science, vol. 9, 2004, pp. 178-184.

Z. Liu et al., "Comparative Study of Electrically Conductive Thick Films with and without Glass," Journal of Electronic Materials, vol. 33, Nov. 3, 2004, p. 194-202.

S. Tu et al., "Time-Resolved Fluorescence Detection of Shiga-Like Toxins Produced by *Escherichia Coli* 0157 and Non-0157 in Ground Beef," Journal of Rapid Methods and Automation in Microbiology, vol. 12, 2004, pp. 247-258.

D. Kim et al., "High-Throughput Cell Manipulation Using Ultrasound Fields," Proceedings of the 26th Annual International Conference of the IEEE EMBS, San Francisco, CA, Sep. 1-5, 2004, pp. 2571-2574.

J. H. Lee et al., "Effect of mass and stress on resonant frequency shift of functionalized $Pb(Zr_{0.52}Ti_{0.48})O_3$ thin film microcantilver for the detection of C-reactive protein," Applied Physics Letters, vol. 84, No. 16, Apr. 19, 2004, pp. 3187-3189.

W. Kunz et al., "The present state of affairs with Hofmeister effects," Current Opinion in Colloid and Interface Science, vol. 9, 2004, pp. 1-18.

V. I. Furdui et al., "Immunomagnetic T cell capture from blood for PCR analysis using microfluidic systems," Lab Chip, vol. 4, 2004, pp. 614-618.

G. Chapman et al, "Bi/In Thermal Resist for Both Si Anisotropic Wet Etching and $Si/SiO_2$ Plasma Etching," SPIE Micro04, Photonics West, Micromachining and Microfabrication Process Technology IX, vol. 5342, 2004.

T. Cha et al., "Immobilization of oriented protein molecules on poly-(ethylene glycol)-coated Si(111)," Proteomics, vol. 4, 2004, pp. 1965-1976.

V. Milanovic, "Multilevel Beam SOI-MEMS Fabrication and Applications," Journal of Microelectromechanical Systems, vol. 13, (Feb. 2004) pp. 19-30.

J. Sobek et al., "Substrate Architecture and Functionality," Microarray Technology, (Sep. 2004), p. 32-44.

S. K. Sia et al., "An Integrated Approach to a Portable and Low-Cost Immunoassay for Resource-Poor Settings," Angew. Chem. Int. Ed. vol. 43 (2004), pp. 498-502.

V. Linder et al., "Reagent-Loaded Cartridges for Valveless and Automated Fluid Delivery in Microfluidic Devices," Analytical Chemistry, vol. 77, No. 1, Jan. 1, 2005, pp. 64-71.

H. Lee et al., "Silicon Bulk Micromachined High Q Film Bulk Acoustic Resonator Devices with Mo/A1N/Mo Structures," Integrated Ferroelectrics, vol. 69, 2005, pp. 323-332.

Microsensors Links, "Magnetically-Excited Flexural Plate Wave Device," website www.sandia.gov/mstc/technologies/microsensors/flexural.html., downloaded May 2, 2005.

QCM-D Technology, http://www.q-sense.com/main.qcmd_html (last visited May 23, 2005) pp. 1-2.

"Microsensors—Thickness Shear Mode Resonators," http://www.sandia.gov/mstc/technologies/microsensors/thicknessshearmode.html (last visited May 23, 2005), pp. 1-3.

"Tone Burst Generators in Research," http://www.ndt-ed.org/EducationResources/CommunityCollege/Ultrasonics/EquipmentTrans/toneburst.htm (last visited May 3, 2005), pp. 1-2.

Y. Yu et al., "High Quality Silicon-Based AIN Thin Films for MEMS Application," Integrated Ferroelectrics, vol. 69 (2005), pp. 367-374.

J. D. Larson et al., "Measurement of Effective $k_t^2, Q, R_p, R_s$ vs. Temperature for Mo/AIN FBAR Resonators," IEEE Ultrasonics Symposium, vol. 1, 2002, pp. 939-944.

R. C. Anderson et al., "Microfluidic Biochemical Analysis System," International Conference on Solid State Sensors and Actuators, Transducers '97, vol. 1, Chicago, Jun. 16-19, 1997, pp. 477-480.

D. Armani et al., "Re-Configurable Fluid Circuits by PDMS Elastomer Micromachining," Proc. of the IEEE Micro Electro Mechanical Systems, Orlando, FL, Jan. 1999, pp. 222-227.

J. Bearinger et al., "PPS-PEG Block Copolymers Render Hydrophobic Surfaces Protein and Cell Resistant," presented at BIOSURF IV, Sep. 20-21, 2001, Lausanne, CH.

C. Cole et al., "A Novel Force Discrimination Assay Using Magnetic Beads," Nova Research, Inc., Alexandria, VA. (last viewed Mar. 12, 2003).

K. S. Breuer, "Design, Fabrication and Performance of MEMS Actuators for Flow Control," in Flow Control and MEMs, Von Karman Institute Lecture Series, Rhode Saint Genese, Belgium, 2002.

J. D. Brewster, "Filtration capture and immunoelectrochemical detection for rapid assay of *Escherichia coli* 0157:H7," Journal of Immunological Methods, vol. 211, No. 1, Feb. 1, 1998, pp. 1-8.

R. Ekins, "Ambient Analyte Assay," Ch. 3, The Immunoassay Handbook, Ed. D. Wild, Elsevier, Boston, 2005, pp. 46-60.

H. Cao et al., "An improved tapered tubular optical waveguide probe for magnetic focusing immunosensors," Proc. of SPIE, vol. 4074, Applications of Optical Fiber Sensors, Aug. 2000, pp. 135-143.

R. A. Conant et al., "Robustness and Reliability of Micromachined Scanning Mirrors," 497 Cory Hall, University of California Berkeley, Berkeley, CA (MOEMS '99).

K. V. Sharp et al., "Liquid Flows in Microchannels," Ch. 6, The MEMS Handbook, CRC Press, New York, 2002, pp. 6-1-6-38.

L. Feller et al., "Control of Protein Adsorption Using Poly(propylene sulfide)-block-poly(ethylene glycol) Adlayers: New Potential Candidate for the Modification of Biosensor Chip Surfaces," Laboratory for Surface Science and Technology, ETH Zurich, Switzerland (2004).

A. G. Gehring et al., "Enzyme-linked immunomagnetic electrochemical detection of *Salmonella typhimurim*," Journal of Immunological Methods, vol. 195, No. 1, Sep. 9, 1996, pp. 15-25.

J. A. Harley et al., "Design of Resonant Beam Transducers: An Axial Force Probe for Atomic Force Microscopy," Proc. ASME Int. Mech. Eng. Congress and Expo, vol. 66, 1998, pp. 247-252.

F. Jiang et al., "Flexible Shear Stress Sensor Skin for Aerodynamics Applications," 13th Annual International Conference on Micro Electro Mechanical Systems (MEMS), Jan. 23-27, 2000, pp. 364-369.

C. Mastrangelo, "Adhesion-Related Failure Mechanisms in Micromechanical Devices," Tribology Letters, vol. 3, No. 3, Sep. 1997, pp. 1-13.

J. Molho et al., "Fluid Transport Mechanisms in Microfluidic Devices," Proc. ASME Micro-Electro-Mechanical-Systems (MEMS), 1998.

P. M. St. John et al., "Metrology and Simulation of Chemical Transport in Microchannels," Solid-State Sensors and Actuators Workshop, Hilton Head, SC, 1998.

A. Padmanabhan et al, "A Silicon Micromachined Floating-Element Shear-Stress Sensor with Optical Position Sensing by Photodiodes," Digest of Technical Papers, Transducers'95, Stockholm, 1995, pp. 436-439.

B. P. Pandian et al., "Biochemical Binding in Microsphere-Based Assays," Proceedings of MSM Conference, 2002, pp. 92-95.

C. J. Bruckner-Lea, "Renewable Surface Biosensors," presented at International Symposium on Ultramicrochemical Process, Taejon, KR, 2002.

S. Pasche et al., "Effects of ionic strength and surface charge on protein adsorption at PEGylated surface," J. Phys. Chem. B, vol. 109, 2005, pp. 17545-17552.

M. A. Rixman et al., "Nanoscale Intermolecular Interactions Between Human Serum Albumin and Alkanethiol Self-Assembled Monolayers," Langmuir, vol. 19, 2003, pp. 6202-6218.

K. S. Ryu et al., "Precision Patterning of PDMS Thin Films: A New Fabrication Method and Its Applications," International Symposium on Micro Total Analysis System (uTAS), Nara, Japan, 2002.

C. A. Savran et al., "Micromechanical Detection of Proteins Using Aptamer-Based Receptor Molecules," Analytical Chemistry, vol. 76, 2004, pp. 3194-3198.

A. W. Wang et al., "A Silicon-based Immunoassay for Detection of Breast Cancer Antigens," International Conference on Solid State Sensors and Actuators, Transducers '97, vol. 1, Chicago, IL, Jun. 16-19, 1997, pp. 191-194.

"Zeta Potential: A Complete Course in 5 Minutes," Zeta-Meter Inc. Published as early as Jul. 3, 2004, see http://web.archive.org/web/20040703234205/http://www.zeta-meter.com/5min.pdf.

C. Han et al., "Micromachined Piezoelectric Ultrasonic Transducers Based on Parylene Diaphragm in Silicon Substrate," 2000 IEEE Ultrasonics Symposium, vol. 1, Oct. 22-25, 2000, pp. 919-923.

S. S. Wong, "Chemistry of Protein connugation and Cross-Linking," CRC Press, New York, 1991.

S. S. Iqbal et al., "A review of molecular recognition technologies for detection of biological threat agents," Biosensors & Bioelectronics, vol. 15, 2000, pp. 549-578.

M. J. O'Brien et al., "SPR biosensors: simultaneously removing thermal and bulk-composition effects," Biosensors & Bioelectronics, vol. 14, 1999, pp. 145-154.

H. Su et al., "Kinetics of interfacial nucleic acid hybridization studied by acoustic network analysis," Biosensors & Bioelectronics, vol. 10, 1995, pp. 329-340.

C. P. Quinn et al., "Photo-crosslinked copolymers of 2-hydroxyethyl methacrylate, poly(ethylene glycol) tetra-acrylate and ethylene dimethacrylate for improving biocompatibility of biosensors," Biomaterials, vol. 16, 1995, pp. 389-396.

E. L. Adler, "Electromechanical Coupling to Lamb and Shear-Horizontal Modes in Piezoelectric Plates," IEEE Transactions on Ultrasonics, Ferroelectrics, and Frequency Control, vol. 36, No. 2, Mar. 1989, pp. 223-230.

J. G. Wetmur, "DNA Probes: Applications of the Principles of Nucleic Acid Hybridization," Critical Reviews in Biochemistry and Molecular Biology, vol. 26, 1991, pp. 227-259.

H. M. Moody et al., "Regiospecific inhibition of DNA duplication by antisense phosphate-methylated oligodeoxynucleotides," Nucleic Acids Research, vol. 17, No. 12, 1989, pp. 4769-4782.

A. Padmanabhan et al., "A Wafer-Bonded Floating-Element Shear Stress Microsensor with Optical Position Sensing by Photodiodes," Journal of Microelectromechanical Systems, vol. 5, No. 4, 1996, pp. 307-315.

Applied Biosytems—Products and Services, at "http://www.appliedbiosystems.com/catalog/" (last visited May 24, 2005), pp. 1-2.

Applied Biosystems Catalog, at "http://www.appliedbiosystems.com/catalog/myab/Storecatalog/products/ CatalogDrillDown.jsp?hierarchyID=101&categorylst1st=..." (last visited May 24, 2005), pp. 1-2.

Applied Biosystems Catalog, at "http://www.appliedbiosystems.com/catalog/myab/Storecatalog/products/ CatalogDrillDown.jsp?hierarchyID=101&categorylst1st=..." (last visited May 24, 2005), p. 1.

Biosite® Inc. Web Site—Products, overview tab, at "http://www.biosite.com/overview/technology.aspx" (last visited May 25, 2005), pp. 1-3.

Biosite® Inc. Web Site—Platforms, platforms tab, at "http://www.biosite.com/overview/platforms.aspx" (last visited May 25, 2005), p. 1.

Biosite® Inc. Web Site—Triage Qualitative—Parasite Panel, products subtab, at http://www.biosite.com/products/paraTechInfo.aspx (last visited May 25, 2005), pp. 1-2.

Boston MicroSystems—Products, products tab, at "http://www.bostonmicrosytems.com/products.shtml" (last visited May 25, 2005), p. 1.

Boston MicroSystems—Microresonator Arrays, microresonator tab, at "http://www.bostonmicrosytems.com/microresonators.shtml" (last visited May 25, 2005), pp. 1-2.

Boston MicroSystems—Chemical Sensors, Chemical Sensors tab, at "http://www.bostonmicrosytems.com/prodcs.shtml" (last visited May 25, 2005), pp. 1-2.

CNN—Breast Cancer Drug "a little less scary," at http://cnn.worldnews.printthis.clickability.com/pt/cpt?action=cpt&title=CNN.com+−+Breast+cancer+dr, last visited on Apr. 18, 2006.

Roddam, A. et al., "Free Estradiol and Breast Cancer Risk in Postmenopausal Women: Comparison of Measured and Calculated Values," Cancer Epidemiology, Biomarkers & Prevention, vol. 12, Dec. 2003, pp. 1457-1461.

"Measurement of Estradiol in Postmenopausal Women Identifies Those at High Risk of Breast Cancer Who May Benefit Most from Raloxifene," at http://professional.cancerconsultants.com/news.aspx?id=29227, last visited on Apr. 24, 2006.

"Estrogens" at http://www.webmd.com/hw/womens_conditions/hw6200.asp, last visited at Feb. 16, 2006.

K. Thygesen, et al., "Myocardial Infarction Redefined—A Consensus Document of The Joint European Society of Cardiology/American College of Cardiology Committee for the Redefinition of Myocardial Infarction," Journal of the American College of Cardiology, vol. 36, No. 3, Sep. 2000, pp. 959-969.

S. Goodacre, et al., "Which Diagnostic Tests are Most Useful in a Chest Pain Unit Protocol?" BioMed Central, BMC Emergency Medicine, Aug. 25, 2005, pp. 1-7.

K.R. Herren, et al., "Is it possible to exclude a diagnosis of myocardial damage within six hours of admission to an emergency department?" BMJ, vol. 323, Aug. 18, 2001, pp. 1-4.

L. Babuin, et al., "Troponin: The biomarker of choice for the detection of cardiac injury," CMAJ, Nov. 8, 2005, pp. 1191-1202.

A. Worster, et al., "Capability of ischemia-modified albumin to predict serious cardiac outcomes in the short term among patients with potential acute coronary syndrome," CMAJ, Jun. 21, 2005, pp. 1685-1690.

R.H. Baevsky et al.,"Beckman Access versus the Bayer ACS: 180 and the Abbott AxSYM cardiac Troponin-I real-time immunoassays: an observational prospective study," BMC Emergency Medicine, Jul. 13, 2004, available online: http://wwvv.biomedcentral.com/1471-227X/4/2.

X. Su, et al., "Design and Application of Piezoelectric Quartz Crystal-based Immunoassay," Analytical Sciences, vol. 16, Feb. 2000, pp. 107-114.

Pepper, J., "Detection of Proteins and Intact Microorganisms Using Microfabricated Flexural Plate Silicon Resonator Arrays," *Sensors and Actuators B*, vol. 96, 2003, pp. 565-575.

International Search Report for International Application No. PCT/US2006/016874, date of mailing Apr. 12, 2006.

International Search Report for International Application No. PCT/US2006/048327, date of mailing May 11, 2007.

Grate et al., "Acoustic Wave Sensors," Sensors Update, 1996, pp. 37-83.

N. Barié, et al., "Covalent bound sensing layers on surface acoustic wave (SAW) biosensors." Biosensors & Bioelectronics (2001), vol. 16, pp. 979-987.

J. Li, et al., "Piezoelectric immunosensor based on magnetic nanoparticles with simple immobilization procedures." Analytica Chimica Acta (2003), vol. 481, No. 2, pp. 191-198.

* cited by examiner

METHOD AND APPARATUS FOR ANALYZING BIOPROCESS FLUIDS

RELATED APPLICATIONS

This application claims priority as a continuation-in-part to each of U.S. application Ser. Nos. 11/416,789; 11/417,000; 11/416,624; 11/417,005; 11/416,998; 11/416,997 which were filed May 2, 2006 and which claim the benefit of U.S. Application No. 60/676,759, filed May 2, 2005 and also claim priority as a continuation-in-part to U.S. application Ser. No. 11/183,484, filed Jul. 18, 2005, now U.S. Pat. No. 7,300,631, which claims the benefit of U.S. Application No. 60/690,592, filed Jun. 15, 2005, the teachings of which are incorporated herein in their entireties. This application also claims the benefit of U.S. Application No. 60/751,492, filed Dec. 19, 2005, the teachings of which are incorporated herein in its entirety.

TECHNICAL FIELD

The present invention relates to methods for detecting one or more biological markers in bioprocess fluid samples.

BACKGROUND OF THE INVENTION

Biological therapeutics such as proteins are produced in various animal and host cell models. Typically, the product molecule of interest is isolated from the host, host cell, or conditioned medium used to grow the host cell and is purified to remove host proteins and other contaminants before being administered to humans. Sensitive measurement of such host proteins and contaminants is desirable at various points during purification of the product molecule. Currently, techniques for detecting or measuring the host cell proteins and contaminants during purification of product molecules typically involve Enzyme Linked Immunosorbant Assay using antibodies that recognized the host cell protein or contaminant. Such assays typically take at least 5 hours to complete and are typically performed off line, that is samples are removed from the production line and taken to a separate laboratory where the assay is performed. The assays often have a detection limit of about 400 pg/ml.

Significant challenges for a system that detects analytes (e.g., biological agents or biological markers) in liquid media include concentration of the analyte in the media, and transport of the analyte to a sensor surface. For biological applications such as analysis of bioprocess fluids for host cell proteins or contaminants, concentration issues generally arise since the concentrations of such analytes tend to be low. Additionally, biological analytes (e.g., cells, cell fragments and macromolecules such as proteins and nucleic acids) tend to be relatively large; hence, transport issues arise because these larger analytes diffuse in fluid solution very slowly. In addition to cells, cell fragments, and molecules such as proteins and nucleic acids, the detection of small molecule analytes can be a useful marker for diagnosing disease, monitoring drug pharmacokinetics in a patient, screening small molecule libraries for potential drug targets and analyzing bioprocess fluids.

There is a need for improved assays that can quickly detect low concentrations of analyte. In addition, there is a need for improved measurement of analytes including small molecule analytes. Furthermore, a need exists for highly sensitive methods and apparatus for analyzing bioprocess fluids and methods and apparatus that can be used in real time at the production line, or even in line with production in order to streamline the purification process. The ability to analyze bioprocess fluids at line or in line at various stages of the purification process is expected to allow more rapid troubleshooting of production problems, thereby minimizing production downtime.

A key metric for competitive detection is the amount of analyte accumulated on a sensor per unit time. For good performance, the rate of accumulation (and the resulting signal transient) needs to be fast relative to the sensor drift rate. Another key performance metric for an analyte detection system is the degree to which the system can preferentially collect the analyte of interest on the sensor surface. Since many biological samples contain extraneous background components (e.g., other proteins, cells, nucleic acids, dirt), it is necessary to prevent these background components from interfering with the desired measurement. So, a transport method that selectively draws the analyte to the sensor and allows interfering background components to pass by has definite advantages. Such a method used in concert with selective binding of the analyte (e.g., antibody, complimentary DNA strands, etc.) to the sensor surface can deliver high sensitivity measurements for samples with large amounts of extraneous background components relative to the amount of analyte.

Various methods for improving transport of analyte to a sensor surface have been proposed, including filtration, novel flow geometries, acoustic fields, electrical fields (time varying and static) and magnetic fields.

Acoustic excitation has been used to draw cells to field nodes, but it is difficult to use this technique alone to transport material to a surface.

Electrical fields (electrophoresis and dielectrophoresis) have been used to enhance transport but are not universally applicable to all analytes and sample types. They are generally more effective for larger analytes (e.g., cells). Furthermore, the electrical properties of microbes can vary within a given species and strain, making it hard to predict system performance under all intended operating conditions. Sometimes it is necessary to tailor the ionic strength of the sample to improve the performance of the transport. This requirement can conflict with the optimum binding or wash conditions in an assay. Also, electrical fields can dissipate energy and heat conductive fluids (e.g., 0.1 M phosphate buffer solution), which is undesirable since heating can damage the biological analytes.

Immunomagnetic separation (IMS) methods are known in the art for isolating analyte from a sample.

SUMMARY OF THE INVENTION

In one embodiment, methods for analyzing a bioprocess fluid are provided. In some embodiments, the method comprises introducing a bioprocess fluid and a plurality of particles coated with a plurality of capture agents capable of binding one or more biological markers into a fluid chamber. At least one surface of the fluid chamber comprises an acoustic device having a plurality of capture agents capable of binding the one or more biological markers bound thereto. Signal output by said acoustic device is monitored, thereby detecting one or more biological markers in the bioprocess fluid.

In some embodiments, the analysis includes assessing the purity of a bioprocess fluid. For example, in some embodiments, the method involves detecting a level of one or more biological markers in the bioprocess fluid. The method comprises introducing the bioprocess fluid and a plurality of particles coated with a plurality of capture agents capable of binding the biological marker into a fluid chamber. At least one surface of the fluid chamber comprises an acoustic device having a plurality of capture agent capable of binding the one or more biological markers bound thereto. Signal output by said acoustic device is monitored to detect the level of one or more biological markers in the sample, thereby assessing purity of a bioprocess fluid.

In some embodiments the method involves detecting a level of one or more biological markers in the bioprocess fluid. The bioprocess fluid is combined with a plurality of magnetic particles that comprise a plurality of capture agents having an affinity for one or more biological markers to produce at least some magnetic particles bound to at least some of the one or more biological markers. The combined fluid is directed into a fluid chamber, wherein at least one surface of the fluid chamber comprises an acoustic device having a plurality of capture agents capable of binding the one or more biological markers bound thereto. A magnetic flux is created in proximity to the flexural plate wave device to magnetically attract at least some of the plurality of bound magnetic particles to the at least one surface of the flexural plate wave device, and signal output by said acoustic device is monitored, to detect the level of one or more biological markers in the sample, thereby assessing purity of a bioprocess fluid.

Apparatus for assessing purity of a bioprocess fluid is also provided. In some embodiments, the apparatus comprises a fluid chamber having at least one opening for fluid to enter; a flexural plate wave device defining at least a portion of at least one interior surface of the fluid chamber. In some embodiments, the at least one interior surface is capable of being coated with a plurality of capture agents that are capable of binding one or more biological markers. In other embodiments, the surface is coated with a plurality of capture agents that are capable of binding one more biological markers. The apparatus includes an monitoring device to monitor at least one signal output by the flexural plate wave device. In some embodiments, the apparatus includes a plurality of magnetic particles capable of being coated with a plurality of capture agents capable of binding one or more biological markers. In other embodiments, the plurality of magnetic particles are coated with a plurality of capture agents that are capable of binding one or more biological markers. The apparatus can also include a source of magnetic flux to selectively attract magnetic particles to the flexural plate wave device.

In one embodiment the biological marker binds to a magnetic particle (e.g., a magnetic bead) to form an analyte-particle complex. The analyte-particle complex is transported and localized onto the surface of a sensing device by applying a gradient magnetic field. The magnetic field induces a polarization in the magnetic material of the particle that is aligned with the local magnetic field lines. The particle experiences a net force in the direction of the gradient, causing the particle to migrate toward regions of higher field strength. The magnetic field distribution is tailored to draw analyte-particle complexes from a sample flow and distribute them across the surface of the sensing device. The extraneous, background components of the sample (e.g., cells, proteins) generally have a much lower magnetic susceptibility as compared to the magnetic particles, and so the magnetic field does not significantly influence them. Hence, only a very small fraction of this background material interacts with the sensor surface.

In one embodiment, the sensing device is a flexural plate wave (FPW) device, which functions particularly well with the magnetic particles for two reasons. First, the presence of the magnetic particles on the surface of the sensing device results in an amplified FPW signal response. The larger combined size and density of the analyte-particle complex yields a larger FPW signal response than the analyte alone. Second, the surface of the sensor in the FPW device consists of a thin membrane that is typically only a few micrometers thick, which allows larger magnetic fields and field gradients to be created at the sensor surface because the field source can be positioned closer to the sample flow. This results in higher fractional capture of the analyte from the sample. With this higher capture rate and efficiency, it is possible to process larger sample volumes in shorter times than would be otherwise possible.

In another aspect, a cartridge for a resonant device system includes a first fluid chamber having at least one opening for fluid to enter, and a flexural plate wave device defining at least one interior surface of the fluid chamber. The apparatus further includes a first source of magnetic flux to selectively attract magnetic particles to the at least one interior surface of the first fluid chamber.

In another aspect, a method for detection of a biological marker (also referred to herein as an analyte) includes combining a fluid containing an analyte (also referred to herein as bioprocess fluid) with a plurality of magnetic particles that comprise a capture agent having an affinity for the analyte to produce at least some magnetic particles bound to at least some analyte. The method further includes directing the combined fluid into a first fluid chamber, wherein at least one surface of a flexural plate wave device is in fluid communication with the fluid in the first fluid chamber. The method also includes creating a first magnetic flux in proximity to the flexural plate wave device to magnetically attract at least some of the bound magnetic particles to the at least one surface of the flexural plate wave device.

In another aspect, a method for detection of an analyte includes coating at least a portion of a surface of a flexural plate wave device located in a fluid chamber with a first capture agent, and directing a fluid containing an analyte into the fluid chamber to bind some of the analyte to the capture agent located on the flexural plate wave device. The method further includes directing a fluid containing a plurality of magnetic particles that comprise a second capture agent into the fluid chamber, and creating a magnetic flux in proximity to the flexural plate wave device to attract at least some of the magnetic particles towards the surface of the flexural plate wave device.

The methods and apparatus provided herein can be used at any stage during the processing and/or purification of the product molecule of interest. Typically, processing and/or purification of product molecules involves the stages of feed preparation, capture of the product molecule, intermediate purification and polishing. A sample of the bioprocess fluid can be tested using the method and or apparatus provided herein before, during, or after any one of the stages. The bioprocess fluid can be tested for the presence of one or more biological markers. The bioprocess fluid can also be tested for the presence and/or amount of the product molecule itself. In addition, the flow through liquid of any relevant purification step can be tested for the presence and/or amount of product molecule. In this manner, the purity of the bioprocess fluid and the yield of the product molecule of interest can be monitored.

For example, in many bioprocessing applications, the initial sample or feed stream often has properties that interfere with or reduce the efficacy of downstream purification or processing methods. The sample or feed stream may have, for example, biological markers such as nucleic acids, endotoxins, cell debris, and/or particulates. Techniques such as filtration can be used to remove the biological markers while retaining the product molecule of interest in the bioprocessing fluid. Depending on the size and concentration of the biological marker and product molecule of interest, microfiltration, ultra filtration, or diafiltration or combinations thereof can be used. The resulting bioprocess fluid can be analyzed for the presence and/or amount of the biological markers as well as for the presence and/or amount of the product molecule.

After conditioning the initial sample, the product molecule is recovered and/or stabilized from the relatively crude feedstock. The recovery process typically involves some form of binding process, where the product molecule is reversibly bound to a solid support, while the rest of the feedstock is washed away. Reversible binding of the product molecule can be achieved, for example, using one or more antibodies that specifically bind the product molecule, ion exchange chromatography (IEC), or hydrophobic interactions. Typically biological markers that have very different pI, hydrophobicity, size, and/or antigenic properties from the product molecule are removed. Further, any biological markers that can damage the product molecule, such as proteases are also removed, while recovering a maximal amount of the product molecule. The resulting bioprocess fluid can be analyzed for the presence and/or level of the biological markers as well as the presence and/or level of the product molecule. In addition, the flow through liquid from the capture stage can be tested for the presence and/or level of product molecule that was not captured, thereby allowing the operator to optimize the efficiency of the capture process at line or in line with the process.

After the capture stage, intermediate purification can be performed. After intermediate purification, steps can be taken to remove any remaining trace contaminants or biological markers that have been difficult to remove due to the similarities with the product molecule can be removed from the bioprocess fluid. Techniques such as IEC, hydrophobic interaction chromatography, and/or gel filtration are often used for intermediate purification and polishing with more selective washing or elution buffers in order to remove biological markers that are more similar in size, charge, and/or hydrophobicity to the product molecule of interest. Like the capture stage, the flow through liquid and resulting bioprocess fluid can be analyzed for the presence and/or amount of product molecule as well as the presence and/or amount of biological markers.

As a result of the methods and apparatus described herein, it is now possible to analyze a bioprocess fluid for the presence and/or amount of product molecule as well as the presence and/or amount of biological markers such as contaminants on the same platform. For example, one surface of the apparatus can be coated with a capture agent that binds the product molecule and another surface coated with a capture agent that binds one or more biological markers. The sample can be introduced to the first and second surfaces and the presence and/or amount of product molecule can be measured by monitoring the frequency shift of the first surface. The sample can be introduced to the second surface in conjuction with particles (also referred to herein as beads), that have been coated with capture agent as described supra. The presence and/or amount of the biological marker can be measuered using the second surface.

Where the product molecule is present at concentrations of 1 mg/ml or more, the sample of bioprocess fluid can be diluted as necessary before introducing the sample to the functionalized surface. In some embodiments, the bioprocess fluid is diluted by a factor of about 10. In other embodiments, the bioprocess fluid is diluted by a factor of about 100.

In some embodiments, the functionalized surface can be calibrated using known concentrations of analytes. In some embodiments, the functionalized surface can be reused. After use, analyte and/or analyte bound to particles can be removed by washing the surface with a suitable washing solution. In some embodiments, the washing solution can be phosphoric acid. The washing solution can be, for example, 0.1 M phosphoric acid. The washing solution can be flowed over the surface for a suitable period of time to remove the analyte and/or analyte/particle complexes. In some embodiments, the washing solution is flowed over the surface for 1 minute. In this manner, the functionalized surfaces can be reused multiple times. In some embodiments, the surfaces can be reused 10 or more times. A calibrated functionalized surface need not be recalibrated after each use or after stripping away the analyte or analyte/particle complexes.

As a result of the present invention, lower levels of analyte can be detected compared to conventional assays. The methods and apparatus provided herein allow for analysis of the bioprocess fluid in less time and can be performed at the production line.

Surprisingly, the use of fewer particles per sample allows for more sensitive detection of analyte. This was found where the size of the analyte is on the order of the size of the particle, and where the analyte is a small molecule. Furthermore, devices fabricated and methods performed according to the principles of the present invention are particularly useful for capturing low concentrations of particles because the sensor surface is thin (for example, in one embodiment, on the order of several microns). In one embodiment, the thin surface is used in conjunction with a magnetic field gradient and magnetic particles. Because the sensor surface is thin, a large magnetic field gradient can be induced one the side of the sensor surface. The large magnetic field gradient enhances the attraction of the magnetic particles to the sensor surface by focusing the field close to the surface of the sensor, while allowing other material contained in the sample to flow by. In this way, lower numbers of particles can be used, thereby improving the detection limit of the system, because the magnetic field gradient serves to concentrate the particles near the sensing surface where they can interact with the bound analyte or capture agent, depending on the assay format. The magnetic field gradient is removed to allow any non-specifically bound particles to be washed away. Thus, the present invention improves the accuracy and the sensitivity of analyte detection.

BRIEF DESCRIPTION OF DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

The present invention is drawn to methods of detecting one or more biological markers (also referred to herein as an analyte) in a sample, such as a bioprocess fluid, using an acoustic device. In general terms, an analyte is detected based on the ability of particles coated with a capture agent (also referred to herein as a first capture agent) to alter the resonating frequency of an acoustic device in the presence of the analyte. The capture agent is capable of binding to the analyte. A plurality of particles coated with a capture agent is exposed to the sensing surface of the acoustic device in the presence of the sample, and optionally in the presence of a competitor molecule. Depending on the type of analyte to be detected, the sensing surface is coated with a capture agent (also referred to herein as a second capture agent) capable of binding the analyte (e.g., a sandwich binding format), or the sensing surface is coated with a competitor molecule (e.g., a small molecule format). The sensing surface is part of a fluid chamber or channel as described herein. In addition, the coated particles and/or sample can be exposed to the sensing surface in a static mode, for example, the coated particles and/or sample can be introduced into the chamber and incubated with the period for a given period of time. In another embodiment, the coated particles can be exposed to a sensing surface in a non-static mode, for example, by flowing the coated particles through the fluid chamber or channel.

Generally, in the sandwich assay formats of the present invention, the amount of particles capable of binding to the sensing surface of the acoustic device is proportional to the amount of analyte present in the sample. Higher levels of analyte in the sample results in more of the capture agent on the particles being occupied by analyte from the sample. Analyte coated particles are then able to bind to the capture agent coated sensing surface. In a preferred embodiment, the particles are magnetic, and a magnetic flux is applied in proximity to the acoustic device to attract at least one of the plurality of magnetic particles toward the sensing surface.

Figure 17:
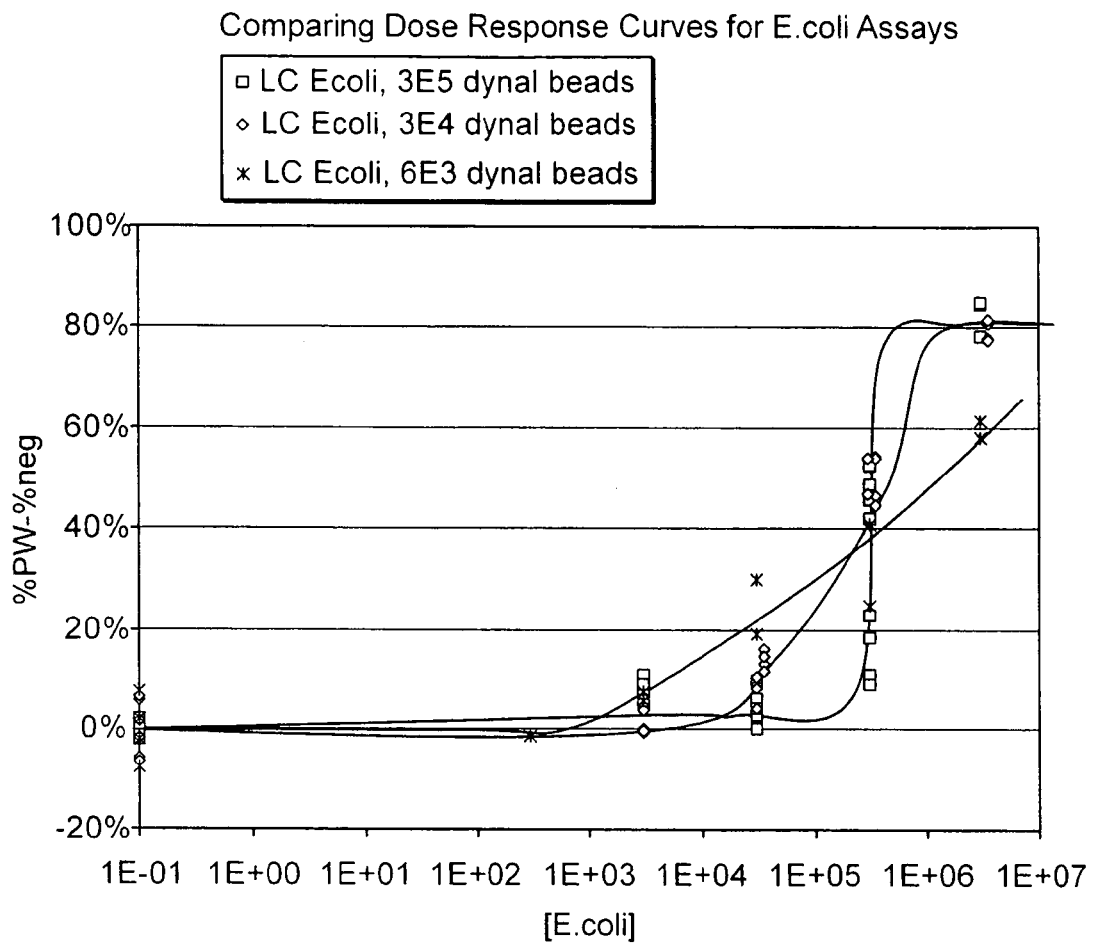
FIG. 17 shows the change in signal from multiple FPW sensors as a function of particle concentration.

As described herein, it was surprisingly found that using a lower concentration of particles allowed for the detection of lower concentrations of analytes. The finding was unexpected because conventional wisdom in assays involving capture by particles calls for the use of a high quantity of particles in order to maximize capture efficiency. However, as shown in FIG. 17, it was found that detection limits were greatly affected by particle concentration and that use of lower particle concentrations allowed for the detection of analytes at lower concentration. Briefly, various concentrations of live $E.$ $coli$ were incubated with $3\times10^5$, $3\times10^4$, or $6\times10^3$ dynal beads and analyzed by the method of the present invention.

Lower particle concentration also lowers capture efficiency. However, on balance, the large improvement in detection limit outweighed the smaller effect on capture efficiency. While not wishing to be bound by theory, in the case of an analyte of a size on the order of the particle, the binding of one analyte per particle is thought to be enough to allow the analyte-bound particle to bind the capture agent coated surface, in part because the bound analyte typically contains multiple sites that can be bound by the capture agent. Use of a large number or high concentration of particles results in many particles that have no analyte bound, which then increases the background signal, by increasing the amount of particles binding the surface non-specifically. Furthermore, if the concentration of particles is high, the non-specifically bound particles may block or prevent particles that have bound analyte from binding to the surface. The particles can be used in a concentration from about $1\times10^2$ to about $1\times10^7$. In another embodiment, the particles are at a concentration of about $5\times10^3$ to about $5\times10^5$.

Figure 7B:
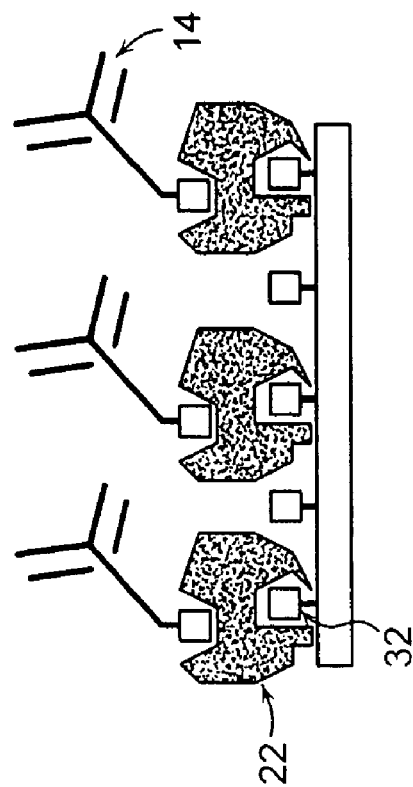
FIG. 7 is a schematic of two formats for attaching a capture agent to the sensing surface of the acoustic device.
Figure 7A:
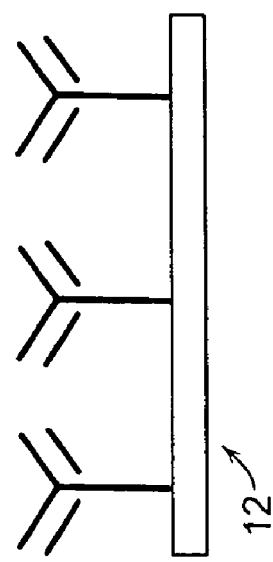

FIG. 7 shows two embodiments where the sensing surface 12 of the acoustic device is coated with a capture agent. In FIG. 7A, the capture agent 14 is bound directly to the sensing surface 12. In FIG. 7B, the capture agent 14 is labeled with a first member of a binding pair 32. The surface is coated with the first member of a binding pair 32 and the second member of the binding pair 22.

Figure 8A:
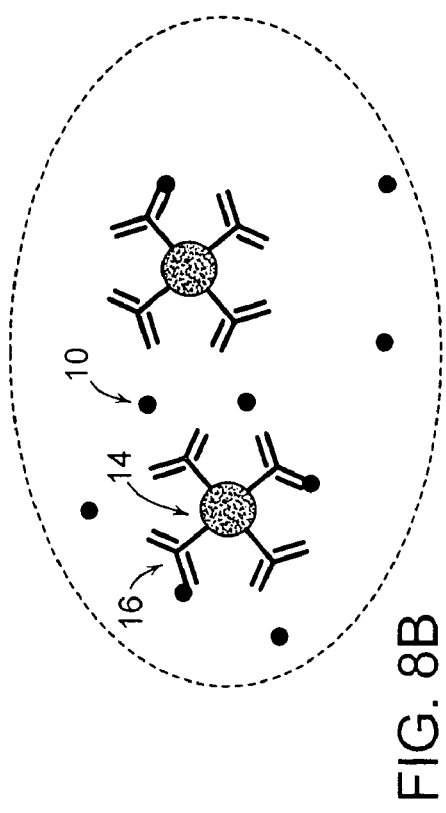
FIG. 8 is a schematic of one embodiment of the present invention, where competitor molecule (e.g., analyte) is bound to the sensing surface.
Figure 8B:
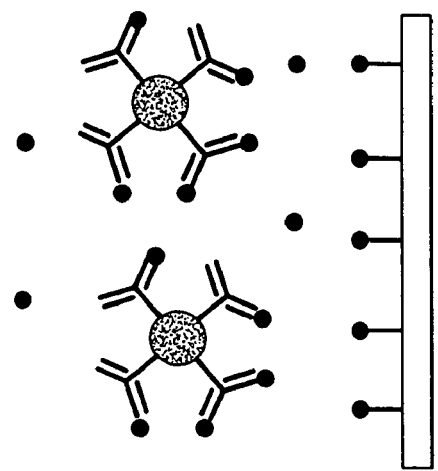
Figure 8C:
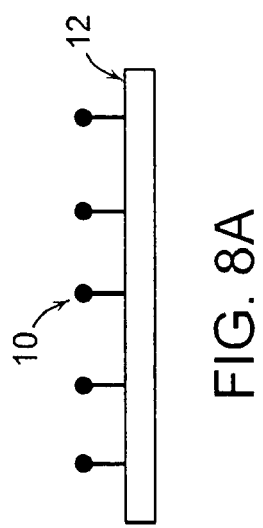
Figure 8D:
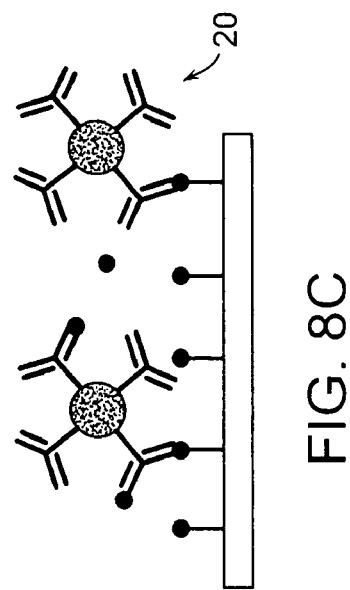
Figure 9B:
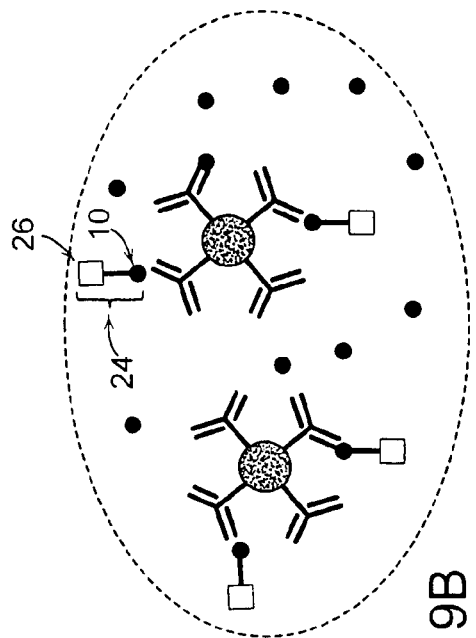
FIG. 9 is a schematic of one embodiment of the present invention, where the competitor molecule is the analyte of interest linked to a tag and the sensing surface of the acoustic device is coated with a capture agent that is capable of binding to the tag.
Figure 9D:
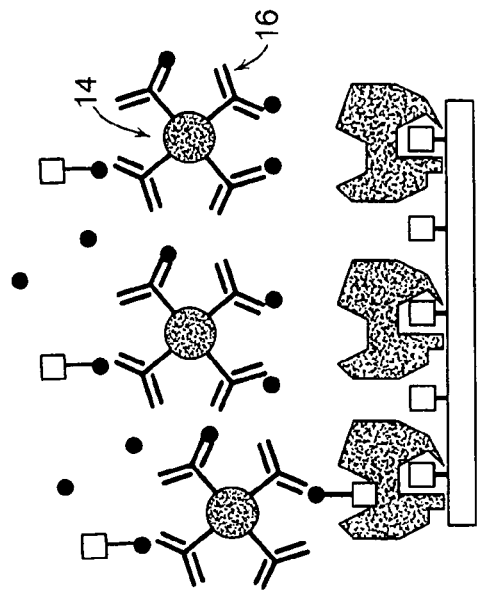
Figure 9A:
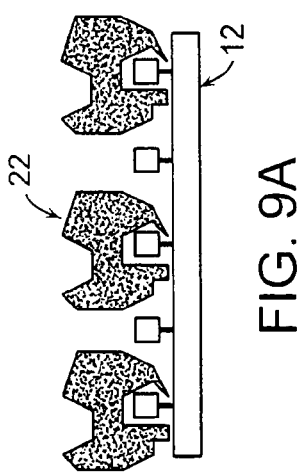
Figure 9C:
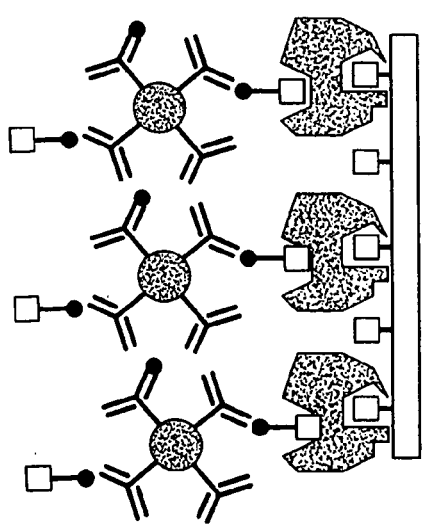

As shown in FIG. 8, in one embodiment of the small molecule format, the competitor molecule 24 comprises the analyte of interest 10 bound to the sensing surface 12 of the acoustic device (FIG. 8A). Particles 14 coated with capture agent 16 are exposed to sample containing the analyte 10 (FIG. 8B). Particle-bound capture agent that that has not bound analyte from the sample 20 is free to bind the analyte bound to the surface of the acoustic device (FIG. 8C). As shown in FIGS. 8C and 8D, higher levels of analyte in the sample result in fewer particles binding the acoustic device sensing surface because more of the capture agent present on the particles is occupied with analyte from the sample. Signal output by the acoustic device is monitored to determine the amount and/or number of particles that have bound to the surface, thereby detecting whether one or more analytes is present in a sample. In addition, the presence or amount of analyte present in the sample can be determined, for example by comparing the signal to a control. In an alternative embodiment, as described herein, the particles can be magnetic particles. After introducing the particles into the fluid chamber, magnetic flux is created in proximity to the acoustic device to attract at least one of the plurality of magnetic particles toward the sensing surface (similarly as described, for example, in FIGS 1A, 1B and 2).

In another embodiment of the small molecule format, as shown in FIG. 9, the sensing surface 12 of the acoustic device is coated with a capture agent 22 (also referred to herein as a second capture agent) that is capable of binding to the competitor molecule 24. The competitor molecule can be, for example, the analyte of interest 10 bound to a tag 26, and the second capture agent is capable of binding to the tag. As shown in FIG. 9, higher levels of analyte in the sample results in fewer particles 14 binding to the sensing surface of the acoustic device because more of the capture agent present on the particles 16 is occupied with analyte from the sample. Because the second capture agent is capable of binding to the tag portion of the competitor molecule, the coated particles bind to the sensing surface of the acoustic device only if the particles have bound the competitor molecule.

In another embodiment of the small molecule format, as shown in FIG. 10, the competitor molecule 24 can be, for example, two or more analyte molecules or moieties of interest 10 bound to a carrier 28 and the second capture agent 40 is capable of binding the analyte. As shown in FIG. 10A, the second capture agent can be indirectly bound to the acoustic device sensing surface. The surface-bound and particle-bound capture agents can be the same capture agent. Particles 14 coated with capture agent 16 are exposed to sample containing the analyte 10 and the competitor molecule 24 (FIG. 10B). Particle-bound capture agent that that has not bound analyte from the sample is free to bind the competitor molecule, which in turn is bound by the capture agent that is bound to the sensing surface (FIG. 10C). As shown in FIG. 10D, higher levels of analyte present in the sample results in fewer particles binding the sensing surface of the acoustic device because more of the capture agent present on the particles is occupied with analyte from the sample. Where the analyte is a small molecule having only one copy of a given epitope or binding site, the coated particles will bind to the acoustic device sensing surface only if the particles have bound to the competitor molecule.

The method of the present invention can be used to determine the concentration or level of the analyte in the sample. The concentration detected or measured by the method of the present invention can be an absolute concentration or a relative concentration. For example, the concentration may be a ratio relative to the concentration of a reference analyte present in the same sample of body fluid. The concentration can be obtained by comparing the data with similar data obtained at a different time to determine whether a significant change in actual concentration has occurred. In addition, the present invention can be used in a binary format that provides a read-out that is positive if the amount of analyte detected is above a predetermined level or concentration and/or negative if the amount of analyte detected is below a predetermined level or concentration. In other embodiments, the method can provide a positive read-out if a certain threshold level of analyte is detected.

For each of the embodiments described herein, a number of variations can be made to the method as described below, without departing from the scope of the invention.

Samples

Samples suitable for use in the present invention includes any material suspected of containing the analyte. The sample can be used directly as obtained from the source or following one or more steps to modify the sample. In one embodiment, the sample is a biological sample. The sample can be derived from any biological source, such as a physiological fluids (e.g., blood, saliva, sputum, plasma, serum, ocular lens fluid, cerebrospinal fluid, sweat, urine, milk, ascites fluid, synovial fluid, peritoneal fluid, amniotic fluid, and the like) and fecal matter. The sample can be obtained from biological swabs such as nasal or rectal swabs. In addition, the sample can be biopsy material. The sample can be obtained from a human, primate, animal, avian or other suitable source. In some embodiments, the sample is a bioprocess fluid. The bioprocess fluid can contain, for example, a product molecule that is to be purified from the bioprocess fluid. The bioprocess can be any sample that contains or is expected to contain the product molecule. For example, the bioprocess fluid can be conditioned tissue culture medium, milk, blood, plasma, plasma fractions, ground tissue, urine, ascites fluid and the like.

The bioprocess fluid can contain recombinantly produced product molecule. In some embodiments, the bioprocess fluid is conditioned medium produced by a recombinant host cell. As described herein, the recombinant host cell can be any suitable cell that has been altered to generate the product molecule, for example, by expressing an exogenous gene or nucleic acid that codes for the product molecule. In some embodiments, the recombinant host cell is selected from the group consisting of bacteria, fungi, insect cells, and mammalian cells into which one or more exogenous nucleic acid sequences have been added. Such nucleic acid sequences include constructs that are capable of expressing, for example, a protein of interest. The exogenous nucleic acid sequence can be introduced into the host cell by, for example, transfection using suitable transfection methods known in the art, or can be introduced by infection using a suitable viral vector, such that the protein encoded by the exogenous nucleic acid is expressed in the host cell. Suitable bacteria include, for example, *E. coli*. Suitable fungi include, for example, *Saccharomyces cerevisiae* or *Pichia pastoris*. Suitable insect cells include, for example, SF9 cells. Recombinant host cells include mammalian cells. Suitable recombinant mammalian cells include, for example, hybridoma cells or transfected mammalian cells. Suitable transfected mammalian cells include, for example, SP2/0 cells, NS/0 cells, Chinese Hamster Ovary (CHO) cells, or Human Embryonic Kidney (HEK) 293 cells to which exogenous nucleic acid has been added as described above.

In other embodiments, the bioprocess fluid can be one or more liquids selected from the group consisting of milk, conditioned cell culture media, blood, serum, plasma, and plasma fractions. In other embodiments, the bioprocess fluid comprises one or more liquids selected from the group consisting of cell homogenates and tissue homogenates.

In some embodiments, the bioprocess fluid can contain an endogenous product molecule, for example, clotting factors and immunoglobulin can be isolated from blood or fractions thereof.

As described above, the methods and apparatus provided herein can be used to analyze bioprocess fluids at all stages of the process used to purify the product from the starting material. As used herein, bioprocess fluid includes the sample as initially obtained (as conditioned cell culture medium, blood, plasma, plasma fractions, milk, tissue homogenates and the like), or can be the product of one or more processing steps to which the sample is subjected during the procedure used to isolate or purify the product from the sample. In one embodiment, the bioprocess fluid has been subjected to one or more purification steps. Such purification steps include, for example, centrifugation, filtration, diafiltration, size fractionation, affinity chromatography, IEC, HIC, gel filtration, dilution, and the like.

In some embodiments, the purified product molecule contains no more than about 1-10 ng/ml of host cell protein, such as CHO-HCP, no more than about 1 ng/ml of endotoxin, no more than about 0.1 ng/ml of DNA, no more than about 1% of aggregates of the product molecule, and sub milligram quantities of protein A.

As described below, the sample can be pretreated prior to use, such as preparing plasma from blood, diluting viscous fluids, and the like. The sample can also be filtered, distilled, extracted, digested with enzyme or concentrated. In one embodiment, a blood sample is obtained from an individual and centrifuged and the plasma is analyzed. The sample can also be treated to inactivate or modify certain activities in the sample capable of interfering with the analyte or the detection process. For example, a decomplexing antagonist can be added to the sample to disassociate the analyte from other molecules that may be bound to and/or may interfere with the ability of the capture agent to bind to the analyte. Such antagonists can be, for example, steroid antagonists. In the case of estradiol detection, the sample can be treated by adding danazol to disassociate estradiol from sex hormone binding protein.

Other samples besides physiological fluids and solids can be used, such as water, food products, and the like, for the performance of environmental or food production assays. For example, the sample can be meat, or poultry wash (the solution used to wash poultry). In addition, a solid material suspected of containing the analyte can be used as the test sample. A solid test sample can be modified (e.g., homogenized, extracted, stomached, or solubilized) to form a liquid medium or to release the analyte.

The sample volume can be as little as 10 µl or as much as 250 ml. In another embodiment, the sample volume is about 1 to about 5 ml.

Capture Agents

Suitable capture agents for use in the present invention include any molecule capable of binding to one or more analytes (e.g., biological markers or product molecule) of interest. The term "capture agent" includes molecules or multi-molecular complexes that can bind to an analyte or biological marker of interest. Capture agents preferably bind to their binding partners in a substantially specific manner. Capture agents with dissociation constants (KD) of less than about $10^{-6}$ are preferred. The capture agent can also be, for example, polypeptides, nucleic acids, carbohydrates, nucleoproteins, glycoproteins, glycolipids and lipoproteins.

In some embodiments, it is desireable to detect the presence or amount of product molecule in the bioprocess fluid. Capture agents includes include molecules that can bind to the product molecule. In some embodiments, the capture agent is protein A, protein G, or other molecule capable of binding to immunoglobulin.

Antibodies or antibody fragments are highly suitable as capture agents. Antigens may also serve as capture agents, since they are capable of binding antibodies. A receptor which binds a ligand is another example of a possible capture agent. Protein-capture agents are understood not to be limited to agents which only interact with their binding partners through noncovalent interactions. Capture agents may also optionally become covalently attached to the proteins which they bind. For example, the capture agent may be photocrosslinked to its binding partner following binding.

As used herein, "plurality of capture agents" includes a mixture of different capture agents such that two or more proteins or two or more antigens that comprise the one or more biological markers can be bound by the plurality of capture agents.

The term "antibody" includes any immunoglobulin, whether naturally produced or synthetically produced in whole, or in part. Derivatives of antibodies that maintain the ability of the antibody to bind to the analyte of interest are also included in the term. The term also includes any protein having a binding domain which is homologous or largely homologous to an immunoglobulin binding domain. These proteins may be derived from natural sources, produced synthetically in whole or in part. In one embodiment, the plurality of capture agents comprises a polyclonal antibody. In another embodiment, the plurality of capture agents comprises a combination of two or more monoclonal antibodies. The antibody may be a member of any immunoglobulin class, including IgG, IgM, IgA, IgD, and IgE. Where the analyte is known to bind a carrier protein, the antibody can be specific for the free form of the analyte or the carrier-bound form of the analyte. Antibodies that are capable of binding an analyte of choice can be obtained commercially or produced using known methods for generating antibodies.

The term antibody also includes antibody fragments. The term "antibody fragments" refers to any derivative of an antibody which is less than full-length. Preferably, the antibody fragment retains at least the ability to bind the analyte of interest. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be synthetically produced in whole or in part. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. "Diabodies" are dimeric scFvs. The components of diabodies typically have shorter peptide linkers than most scFvs and they show a preference for associating as dimers. An "Fv" fragment is an antibody fragment which consists of one $V_H$ and one $V_L$ domain held together by noncovalent interactions. The term "dsFv" is used herein to refer to an Fv with an engineered intermolecular disulfide bond to stabilize the $V_H$-$V_L$ pair. A "F(ab')$_2$" fragment is an antibody fragment essentially equivalent to that obtained from immunoglobulins (typically IgG) by digestion with an enzyme pepsin at pH 4.0-4.5. The fragment may be recombinantly produced. A "Fab'" fragment is an antibody fragment essentially equivalent to that obtained by reduction of the disulfide bridge or bridges joining the two heavy chain pieces in the F(ab')$_2$ fragment. The Fab' fragment may be recombinantly produced. A "Fab" fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

Suitable polypeptide capture agents also include virtually any peptide, polypeptide, or protein that is capable of binding to an analyte of interest, or a small molecule such as a small organic molecule. In one embodiment, the capture agent is an antibody that is capable of binding to the analyte of interest. Suitable polypeptide capture agents may be obtained, for example, commercially, using recombinant methods, using synthetic production methods, or by purification from a natural source. Polypeptides include, for example, cell surface proteins, cell surface and soluble receptor proteins (such as lymphocyte cell surface receptors, steroid receptors), nuclear proteins, signal transduction molecules, transcription factors, allosteric enzyme inhibitors, clotting factors, enzymes (e.g., proteases and thymidylate synthetase, serine/threonine kinases, threonine kinases, phosphatases, bacterial enzymes, fungal enzymes and viral enzymes), proteins associated with DNA and/or RNA synthesis or degradation and the like. As described in more detail below, where more than one capture agent is used, the capture agents can be, for example, isoforms of each other.

In a particular embodiment, where the analyte is a virus, the capture agent can be a cell surface receptor for the virus. For example, where the virus is HIV, the capture agent can be Dendritic cell-specific ICAM-3 grabbing nonintegrin (DC-SIGN) or CD4. In another embodiment the capture agent can be antibodies that are capable of binding viral antigens. For example, the antigen can be gp41 or gp120. The capture agent can be antibodies capable of binding host-derived antigens. For example, the antigen can be CD44, CD54, human leukocyte antigen (HLA) such as HLA-DR, or HLA-DRDPDQ.

The capture agent can also be a nucleic acid such as RNA or DNA, or peptide nucleic acid. In one embodiment, the nucleic acid or peptide nucleic acid is capable of hybridizing to nucleic acid or peptide nucleic acid analyte. In addition, the capture agent can be an aptamer, a nucleic acid capable of binding to non-nucleotide analyte (e.g., proteins, small organic molecules, or inorganic molecules). As used herein, an aptamer can be either an RNA or a DNA chain composed of naturally occurring or modified nucleotides.

Suitable capture agents also include members of binding pairs. Suitable binding pairs include, for example, biotin and avidin or biotin and derivatives of avidin (e.g., streptavidin and NEUTRAVIDIN™).

Capture agents can be bound to the surface or to the bead as described below or by using standard techniques for attaching polypeptides, nucleic acids, protein A, and the like to surfaces.

Analytes

As used herein, the term "analyte" refers to, for example, the molecular structure that is recognized by a capture agent. For example, the term analyte can refer to the epitope recognized by an antibody, or can include that part of a ligand that is bound by a receptor. The term analyte also includes larger molecules that contain a molecular structure that is recognized by a capture agent. The analyte can be part of a cell, for example a cell surface protein. The analyte can be an analyte of interest, chosen by the user (e.g., preselected). The analyte can be selected based on the ability to bind a capture agent of interest, for example in small molecule library screening.

In some embodiments, the analyte is a biological marker that may be present in a bioprocess fluid. As described herein, analysis of bioprocess fluids can be performed using the apparatus described herein in conjunction with a variety of commonly available commercial and specially raised capture agents, depending on the biological marker of interest. Based on the information provided in Example IX, one of ordinary skill in the art would be able to select an appropriate capture agent for the biological marker of interest, and be able to analyze the bioprocess fluid for the presence and/or amount of the biological marker. For example, capture agents that bind endotoxin and capture agents that bind protein A are commercially available.

The presence of one or more biological markers of a panel of biological markers can be assessed or detected. The panel of analytes can include one or more analytes that are detected using a competition format as described herein. The panel of analytes can include one or more analytes that are detected using the sandwich assay format as described herein. In one embodiment, each analyte is detected using a separate cartridge as described below In order to test a panel of one or more analytes, a single sample can be divided into two or more aliquots. Each aliquot can be tested for a different analyte, for example, using a different cartridge for each analyte to be tested. In this manner, panels of different analytes may be tested without requiring that multiple samples be acquired and/or that different types of apparatus be employed to test the detect the different analytes.

As used herein, the biological marker can be any component, other than the product molecule, present or suspected of being present in the starting material or introduced into the bioprocess fluid during processing. The nature of the biological marker or markers will be based in part on the source of the bioprocess fluid, that is conditioned cell culture media, blood, milk, etc. In some embodiments, the biological marker comprises host cell protein (HCP). HCP can be, for example, a mixture of proteins or antigens that are produced and/or shed by the host cell into the culture medium. In other embodiments, the biological marker can be, for example, nucleic acids, proteinases, or viruses. In other embodiments, the biological marker or markers can comprise one or more milk antigens, serum antigens, or plasma antigens from the host animal. In addition, the biological marker can be an aggregate of the product of interest, such as aggregates of immunoglobulin, variants of the product molecule, deglycosylated versions of the product molecule, and the like.

In some embodiments, the one more biological markers comprises one or more contaminants. Such contaminants can be introduced, often unintentionally, during the purification process. For example, protein A or protein G columns are often used to purify antibody from a bioprocess fluid. However, a small amount of protein A or protein G may be shed from the column, thereby contaminating the bioprocess fluid. In some embodiments, the contaminants are microbes or microbial antigens, as described, supra, including for example, protein A, protein, G, endotoxin, lipopolysaccharide, and other microbial toxins. In some embodiments, the one or more biological markers comprises one or more reagents that is added to the bioprocess fluid to facilitate isolation or purification of the product molecule, but that is removed in the final product.

As used herein, the one or more biological markers can be any combination of biological markers described supra. Product molecules can be distinguished from biological markers by a number of criteria including, for example, antigenicity, molecular weight, pI, hydrophobicity, stability, and the like.

In one embodiment, the analyte of interest is a small molecule. Small molecules include organic or inorganic molecules having a molecular weigh of about 1000 g/mol or less. Typically, small molecule analyte will contain a single or only a few binding sites. Because a small molecule has a few or only one binding site, the present invention uses competitive binding to detect and/or quantify small molecule analytes.

The small molecule can include, for example, steroids, lipids, carbohydrates, peptides, and heterocyclic compounds (e.g. bases, including co-factors such as FAD and NADH). The analyte (e.g., small molecule) can be part of a library of small organic molecules which comprise aldehydes, ketones, oximes, hydrazones, semicarbazones, carbazides, primary amines, secondary amines, tertiary amines, N-substituted hydrazines, hydrazides, alcohols, ethers, thiols, thioethers, thioesters, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds and/or acid chlorides, preferably aldehydes, ketones, primary amines, secondary amines, alcohols, thioesters, disulfides, carboxylic acids, acetals, anilines, diols, amino alcohols and/or epoxides, most preferably aldehydes, ketones, primary amines, secondary amines and/or disulfides and combinations thereof.

The analyte of interest can also be a polypeptide, a nucleic acid, a carbohydrate, a nucleoprotein, a glycopeptide or a glycolipid. Useful analytes include, for example, enzymes, steroids, hormones, transcription factors, growth factors, immunoglobulins, steroid receptors, nuclear proteins, signal transduction components, allosteric enzyme regulators, and the like. Analytes of interest can be obtained, for example, commercially, recombinantly, synthetically, or by purification from a natural source. In preferred embodiments, the analyte of interest is associated with a specific human disease or condition.

Suitable growth factors include, for cytokines such as erythropoietin/EPO, granulocyte colony stimulating receptor, granulocyte macrophage colony stimulating receptor, thrombopoietin (TPO), IL-2, IL-3, IL-4, IL-5, IL-6, IL-10, IL-11, IL-12, growth hormone, prolactin, human placental lactogen (LPL), CNTF, and octostatin. Suitable steroids include, but are not limited to, estradiol, progesterone, testosterone, and derivatives thereof. Other suitable analytes include, for example, insulin, insulin-like growth factor 1 (IGF-1), epidermal growth factor (EGF), vascular endothelial growth factor (VEGF), placental growth factor (PLGF), TGF-α and TGF-β), other hormones and receptors such as bone morphogenic factors, follicle stimulating hormone (FSH), and leutinizing hormone (LH), tissue necrosis factor (TNF), apoptosis factor-1 and -2 (AP-1 and AP-2), and mdm2.

In one embodiment, the analyte is a cardiac marker. Cardiac markers are well known in the art and include, for example, c-troponins I and T, myoglobin, creatin kinase MB (CK-MB), and ischemia modified albumin. In one embodiment, the present invention can be used to detect a panel of analytes in order to assess a patient's condition. In one embodiment, a panel of cardiac markers is tested. The panel can include, for example, c-troponin-I, CK-MB, and myoglobin analytes.

In another embodiment, the analyte is a marker for vial infection. Markers for viral infection include, for example, inflammatory markers, circulating viral proteins, CD4+ cells, liver enzymes, and anti-virus antibodies.

The analyte of interest can also be a therapeutic drug where it would be useful to measure the levels of the drug in a patient sample, for example for drug management purposes or patient compliance. Suitable therapeutic drugs include, but are not limited to protease inhibitors and immunosupressants. Suitable protease inhibitors include ageneraser, reyataz, lexiva, telzir, crixivan, kaletra, viracep, norvi, invirase, aortovase, aptivus and the like). Suitable immunosuppressants include cyclosporin, tacrolimus (FK-506), rapamycin, mycophenolic mofetil and the like.

The analyte of interest can be a pathogen or microbe, such as bacteria or bacterial spores, viruses, parasites, prions or other pathogens or their cell wall or surface components such as gram-positive peptidoglycans, lipoteichoic and teichoicacids, and gram-negative endotoxin (e.g.) lipopolysaccharide). Bacterial analytes include, for example, *Shigella* sp. such as *Shigella dysenteriae, Campylobacter* sp. such as *Campylobacter jejuni, Enterococcus* sp. such as *Enterococcus faecalis, Bacillus anthracis, Yersinia pestis, Bordetella pertussis, Streptococcal* species, *Staphylococcus aureus, Mycobacterium tuberculosis, Clostridium difficile, Clostridium tetani, Clostridium botulinum, Escherichia coli, Salmonella thyphimurim, Salmonella enterica, Chlamydia species, Treponema pallidum, Neisseria gonorrhoeae, Borrelia burgdorferi, Vibrio cholerae, Corynebacterium diphtheriae*, and *Helicobacter pylori*. Parasites include, for example, Giardia, malaria and crytosporidia. Viral analytes include, for example, Rhinovirus, Yellow Fever, Group B Coxsachieviruses, (CB1, CB2, CB3, CB4, CB5, and CB6), Canine Parvovirus (CPV), Herpes Simplex virus type 1 (HSV1), Vaccina Virus, T4-like virus, Adenovirus, Influenza B virus, Influenza A, Avian flu, rhinovirus, coronavirus (e.g., SARS), Human Immunodeficiency virus (HIV), Hepatitis viruses, Herpes virus, West Nile Virus, and Ebola virus.

As described above, in some embodiments, more than one analyte is detected. In one embodiment, the analytes have the same molecular structure. The analytes can be, for example the same molecular species of interest. In another embodiment, the different analytes (also referred to herein as the first and second analytes) are part of a larger molecule. Therefore, the analyte can be a particular binding site (such as an epitope) attached to or contained within a larger molecule. As such, the different analytes being detected can be part of different molecules.

Analytes can be bound to the surface or to the bead as described below or by using standard techniques for attaching small molecules, polypeptides, nucleic acids, and the like to surfaces. In one embodiment, the analyte is indirectly bound to the surface. The analyte can be indirectly bound to the surface, for example, by coating the surface with a first member of a binding pair. The analyte is bound or attached to a second member of the binding pair and then the analyte is bound to the surface via the interaction between the first and second members of the binding pair. Suitable binding pairs include, for example, biotin and avidin or biotin and derivatives of avidin such as streptavidin and NEUTRAVIDIN™.

Assay Formats

As described above, in one embodiment of the present invention, a plurality of magnetic particles is introduced into a fluid chamber. The magnetic particles are coated with a first capture agent capable of binding the analyte and at least one surface of the fluid chamber comprises an acoustic device that has been coated with a second capture agent capable of binding to the competitor molecule. The surface can be coated with the second member of the binding pair using any suitable method. For example, the surface can be coated with biotin as described below and then the biotinylated surface can be exposed to avidin or a derivative of avidin, and the second capture agent can be linked to biotin.

In one embodiment, a plurality of magnetic particles and a competitor molecule are introduced into a fluid chamber. The magnetic particles are coated with a first capture agent capable of binding the analyte. At least one surface of the fluid chamber comprises an acoustic device that has been coated with a second capture agent capable of binding to the competitor molecule. In one embodiment, the competitor molecule comprises the analyte linked or bound to a tag, and the second capture agent is capable of binding to the tag. The tag can be any moiety that can be recognized by a capture agent. In one embodiment, the tag is one member of a binding pair and the capture agent is the other member of the binding pair. For example, the tag can be biotin, and the capture agent can be avidin, streptavidin, or NEUTRAVIDIN™. In this embodiment, the biotin is linked to the analyte using known methods for linking molecules to biotin, to form the competitor molecule. The surface can be coated with the second member of the binding pair using any suitable method. For example, the surface can be coated with biotin as described below and then the biotinylated surface can be exposed to avidin or a derivative of avidin.

In another embodiment, the competitor molecule comprises two or more analyte molecules bound to a carrier, and the second capture agent is capable of binding the analyte. The carrier can be any molecule to which two or more analyte molecules can be linked or bound. The carrier can be a protein, a nucleic acid, or other polymer. In one embodiment, the carrier is an albumin, such as bovine serum albumin. In another embodiment, the carrier is horseradish peroxidase. In this embodiment, two or more analyte molecules can be linked to the carrier as described below, or known linking technology can be used to form the competitor molecule. The surface can be coated with the capture agent as described below.

According to one embodiment of the method of the present invention, the plurality of particles can be exposed to the sample using a variety of different orders of exposure. For example, in one embodiment, the plurality of particles is exposed to the sample and then introduced into the fluid chamber. The sample may be concentrated prior to introducing the sample-exposed particles into the fluid chamber. The sample may be concentrated by, for example, removing the particles from the solution and resuspending the particles in a smaller volume of liquid.

In another embodiment, the sample is introduced into the fluid chamber prior to introducing the plurality of particles. In still another embodiment, the plurality of particles is introduced into the fluid chamber prior to adding the sample to the fluid chamber.

In another embodiment, as described above, the plurality of particles is exposed to the sample and to a competitor molecule. The plurality of particles can be exposed to the sample and to the competitor molecule in a number of different orders. For example, in one embodiment, the plurality of particles is exposed to the sample and to the competitor molecule and then introduced into the fluid chamber. In another embodiment, the sample and the competitor molecule are introduced into the fluid chamber prior to introducing the plurality of particles. In still another embodiment, the plurality of particles is introduced into the fluid chamber prior to adding the sample and/or the competitor molecule to the fluid chamber.

Control Signal/normalization

In another embodiment, the signal output of the acoustic device in response to sample exposure is compared to or normalized with a control signal. The control signal can be provided to or obtained by the user. For example, the control signal can be a value provided to the user based on the specific analyte, capture agent, or particular model, version or type of device being used. In one embodiment, the control signal is obtained on a lot basis. For example, the control signal can be a signal that is representative of a particular lot of analyte acquired by the user. The representative signal can be, for example, experimentally derived before, during or after testing of a sample. In some embodiments, the control signal is a standard curve that is obtained by, for example, analyzing known quantities of analyte with a specific capture agent and specific version of an acoustic device.

In another embodiment, the control signal is obtained on a use basis. For example, a unique control signal can be obtained each time a particular analyte and/or capture agent is tested on a particular acoustic device. In one embodiment, the control signal is obtained using the same analyte and/or capture agent, however, in the absence of sample. The control signal can be obtained by introducing a second plurality of particles into the fluid chamber that are coated with a capture agent. At least one surface of the fluid chamber comprises an acoustic device that has a second analyte bound thereto. Signal output by said acoustic device is monitored to determine a control signal to be used in subsequent testing.

As described below for multiplexing, the different pluralities of magnetic particles can be exposed to the same or different surfaces of the fluid chamber.

Acoustic Devices

Acoustic devices couple to fluids predominantly through acoustic interaction between the device and the fluid. Typical acoustic devices include surface acoustic wave devices, flexural plate wave devices, lamb wave devices and cantilever devices. Acoustic devices also couple to fluids through some viscous interaction between the device and the fluid, however, the coupling is predominantly acoustic coupling. Viscous interaction devices couple to fluids predominantly through viscous interaction between the devices and the fluid. Typical viscous interaction devices include quartz microbalance (QCM) devices, shear harmonic surface acoustic wave devices, and acoustic plate mode devices. The term "surface acoustic wave" refers to the manner in which energy is carried in the device structure rather than how the device couples to the fluid. Acoustic devices are devices where fluid interacts over a substantial area of a plane of the device. Acoustic devices respond with substantial out of plane motion that couples acoustically to fluid in proximity to the plane of the device (i.e., kinetic energy, potential energy and losses are carried predominantly in the fluid). Viscous interaction devices respond primarily with in-plane motion that does not couple acoustically to fluid in proximity to a plane of the device.

For applications involving, for example, the detection and quantification of biological or chemical substances in a fluid, the coupling between an acoustic device and a fluid is typically between about 100 nm and about 10 microns in thickness relative to the plane of the device where the coupling between a viscous interaction device and a fluid is between about 10 nm and about 100 nm in thickness relative to the plane of the device.

Surface acoustic wave devices and shear harmonic surface acoustic wave devices both carry energy in their respective structures in similar manners. Surface acoustic wave devices acoustically couple significantly to fluids while shear harmonic surface acoustic wave devices couple to fluids predominantly through viscous interaction.

Figure 1A:
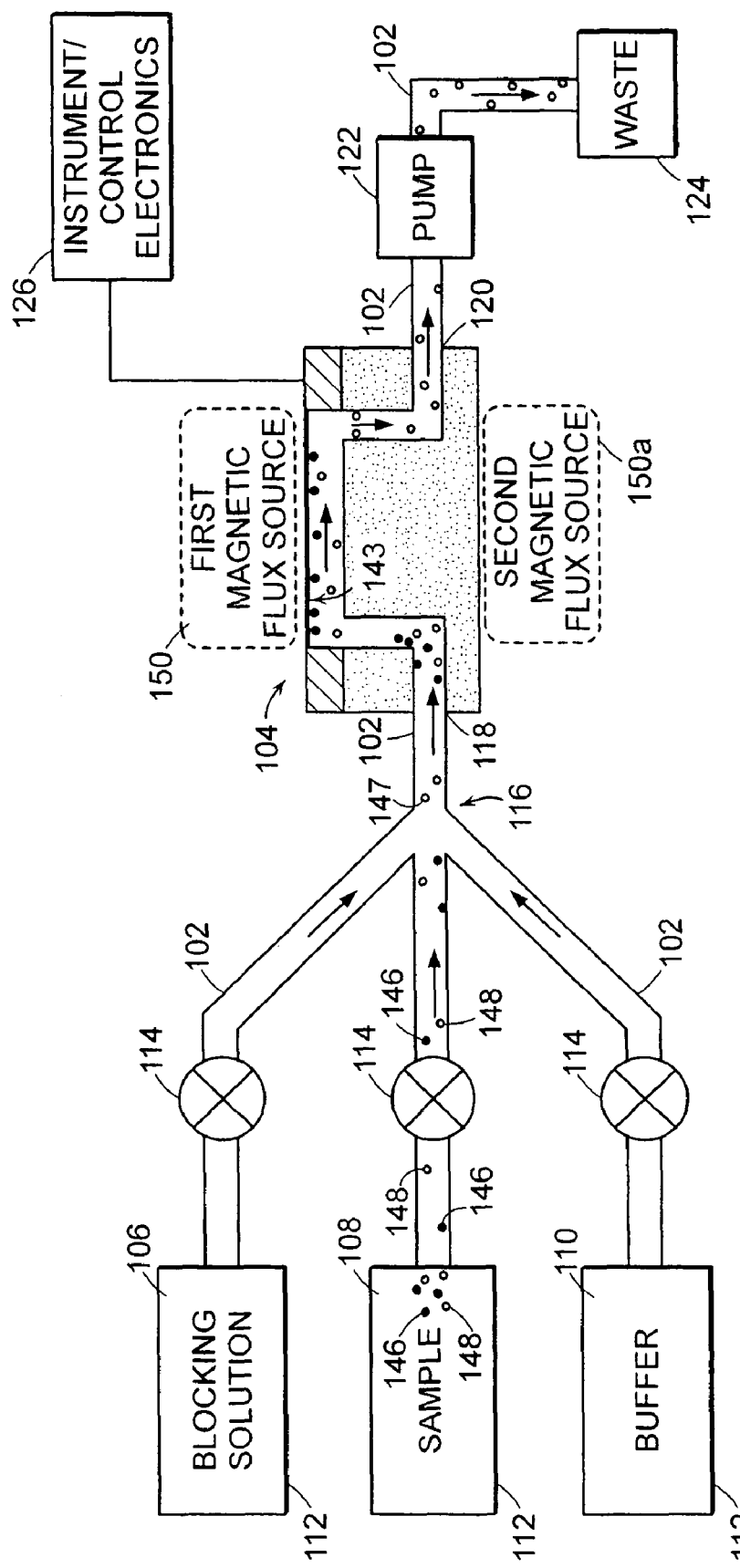
FIG. 1A shows one embodiment of an analyte detection system, constructed according to the invention.

One embodiment of an analyte detection system 100, constructed according to the invention, is shown in FIG. 1A. The system 100 includes a network of channels 102 for transporting various test solutions (also referred to herein as "test fluids" or "fluids") through an FPW device 104. The following U.S. patents and patent applications, all of which are hereby incorporated by reference, describe examples of the various types of FPW devices suitable for use in the present invention: U.S. Pat. Nos. 5,129,262, 5,189,914, 6,688,158 B2, U.S. patent application Ser. No. 10/324,685, U.S. Pat. Nos. 5,668,303, 5,836,203, and U.S. Patent Application 20040038195.

For example, U.S. Pat. No. 5,129,262 describes an ultrasonic sensor that has a thin planar sheet of material forming a Lamb wave propagation medium. Lamb waves, also known as plate-mode waves, can propagate only through a material of finite thickness. In contrast to surface acoustic waves (SAWs), which require a propagation medium having a thickness on the order of hundreds of times the wavelength of the propagating SAW, Lamb waves require a propagation medium which is at most only several wavelengths thick, and typically only a fraction of the wavelength of the propagating Lamb wave. The thickness of the sheet is no greater than about twenty microns. A Lamb wave generator generates Lamb waves in the planar sheet, and an output device produces an electrical signal that represents the propagation characteristics of the Lamb waves propagating along the sheet. A measuring device measures selected characteristics of the output electrical signal. The planar sheet has some physical characteristics that depend upon the value of a measurand acting on the sheet, and those physical characteristics consequently determine the propagation characteristics of the Lamb waves that propagate along the sheet. Since the electrical signal from the output device represents the propagation characteristics, the electrical signal also represents the value of the measurand acting on the sheet.

The Lamb wave device described in U.S. Pat. No. 5,129,262 can be employed, for example, in biological sensing. The planar sheet described above can be pre-coated with antibody molecules, so that the frequency of the device changes upon immersion in or contact with a liquid that contains the corresponding antigen. Antigen-antibody attachment at the surface of the propagation medium acts to alter the wave velocity of the Lamb waves in the sheet. The change in wave velocity causes the oscillation frequency to change in a delay line oscillator form of the device. Also, the sheet may be made of a porous and permeable material, allowing the coating of antibody molecules over a greater surface area of the sheet and also allowing the antigen-containing liquid to be flowed through the membrane, in order to speed up the antigen-antibody attachment. Other biological interactions may also be sensed, and additional applications include immunoassay, clinical laboratory testing, in vivo biomedical monitoring, and biomedical research.

The test solutions used in the described embodiment, for example a blocking solution 106, a sample 108, and a buffer 110, are sourced from reservoir containers 112. The channel path from each of the reservoirs 112 is gated with a valve 114 to control the flow of a particular test solution to a combination point 116 leading to an entry port 118 of the FPW device 104. The test solution flows through the FPW device 104 and exits via an exit port 120, which leads to a pump 122. The pump 122 draws the test solution through the network of channels 102 and through the FPW device 104, and directs the test solution to a waste receptacle 124.

Figure 1B:
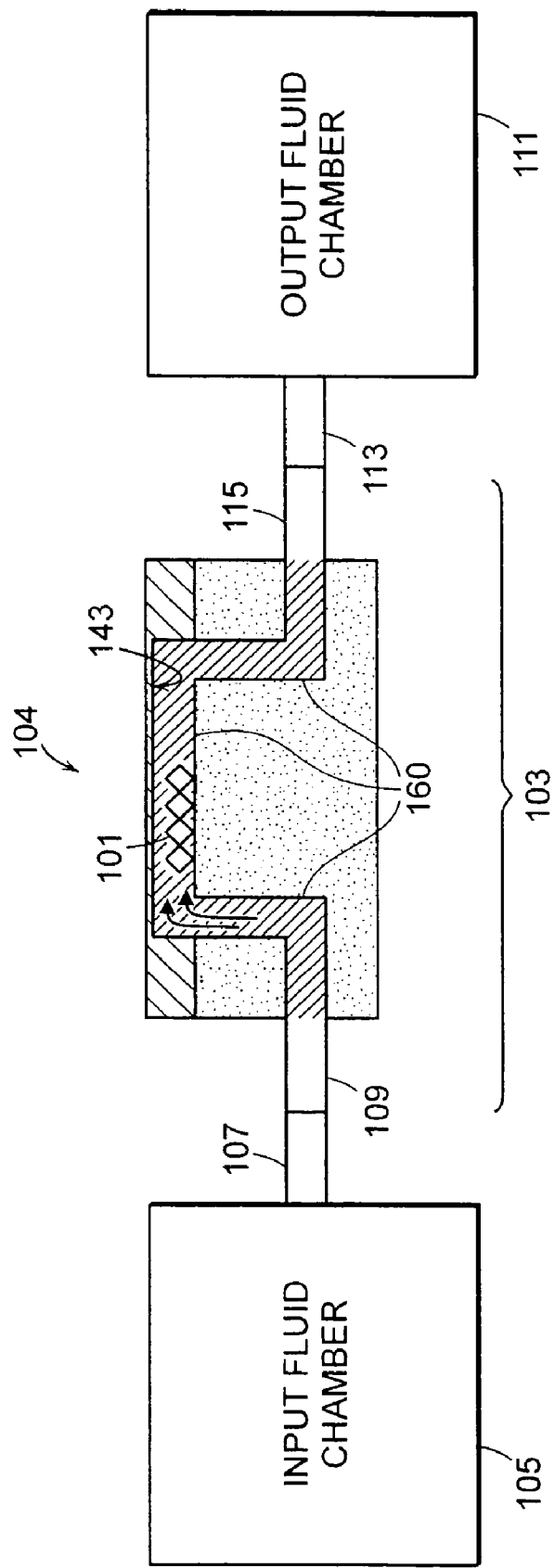
FIG. 1B shows another embodiment of a portion of the analyte detection system shown in FIG. 1A.

FIG. 1B shows another embodiment of the analyte detection system 100. This embodiment packages the FPW device 104 and its associated fluid chamber 160 as a cartridge 103, i.e., a consumable component that can be removed and replaced. Some embodiments may include a fluid control device 101 such as a plug, obstruction or baffle that alters the flow through the device 104. In one embodiment, the fluid control device 101 operates to cause the fluid flow through the device 104 to pass closer to the sensor surface 143 than if the fluid control device 101 was not present. Further, the source of input test solutions is shown as an input fluid chamber 105 that has an outlet 107 for directing the test solutions into the inlet 109 of the cartridge 103. In some embodiments, the magnetic particles are initially located in the input fluid chamber 105 and the fluid containing analyte is mixed with the magnetic particles in the input fluid chamber 105 and then directed into the cartridge 103 in which the FPW device 104 is located. The magnetic particles may be combined within the input fluid chamber 105 with the fluid containing analyte by a device (e.g., by the action of a pump or a magnetic agitator). FIG. 1B further shows an output fluid chamber 111 with an inlet 113 that receives fluid from the outlet 115 of the cartridge 103. This output fluid chamber 111 may include one or more of the fluid control devices described herein, and it may include one or more mechanisms for storing and/or treating waste fluid.

In at least one embodiment, the junction where the outlet 107 of the input fluid chamber 105 meets the inlet 109 of the cartridge 103 is constructed and arranged to allow repeatable connection and disconnection. Similarly, the junction where the outlet 115 of the cartridge 103 meets the inlet 113 of the output fluid chamber 111 is constructed and arranged to allow repeatable connection and disconnection. In some embodiments, these junctions are constructed and arranged to require tools for connection and disconnection, such as threaded couplings that require a wrench or other such tool to affect the coupling and decoupling. In other embodiments, these junctions are constructed and arranged to allow quick and easy manual connection and disconnection, without any extra tools or accessories. Such couplings, both requiring and not requiring tools, are known in the art. In some embodiments, there are multiple input fluid chambers and output fluid chambers. In some embodiments, one or more input and/or output fluid chambers are part of the cartridge 103. Further, in some embodiments, one or more sources of magnetic flux are part of the cartridge.

Figure 2A:
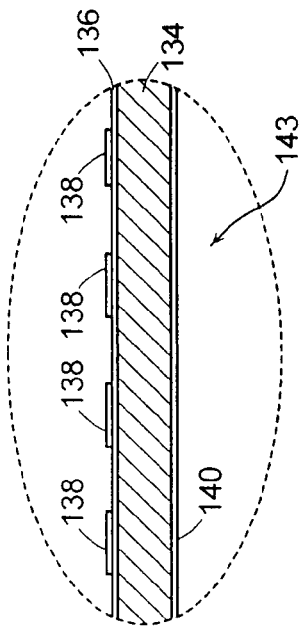
FIG. 2A shows a more detailed view of the FPW sensor shown in FIG. 2.
Figure 2:
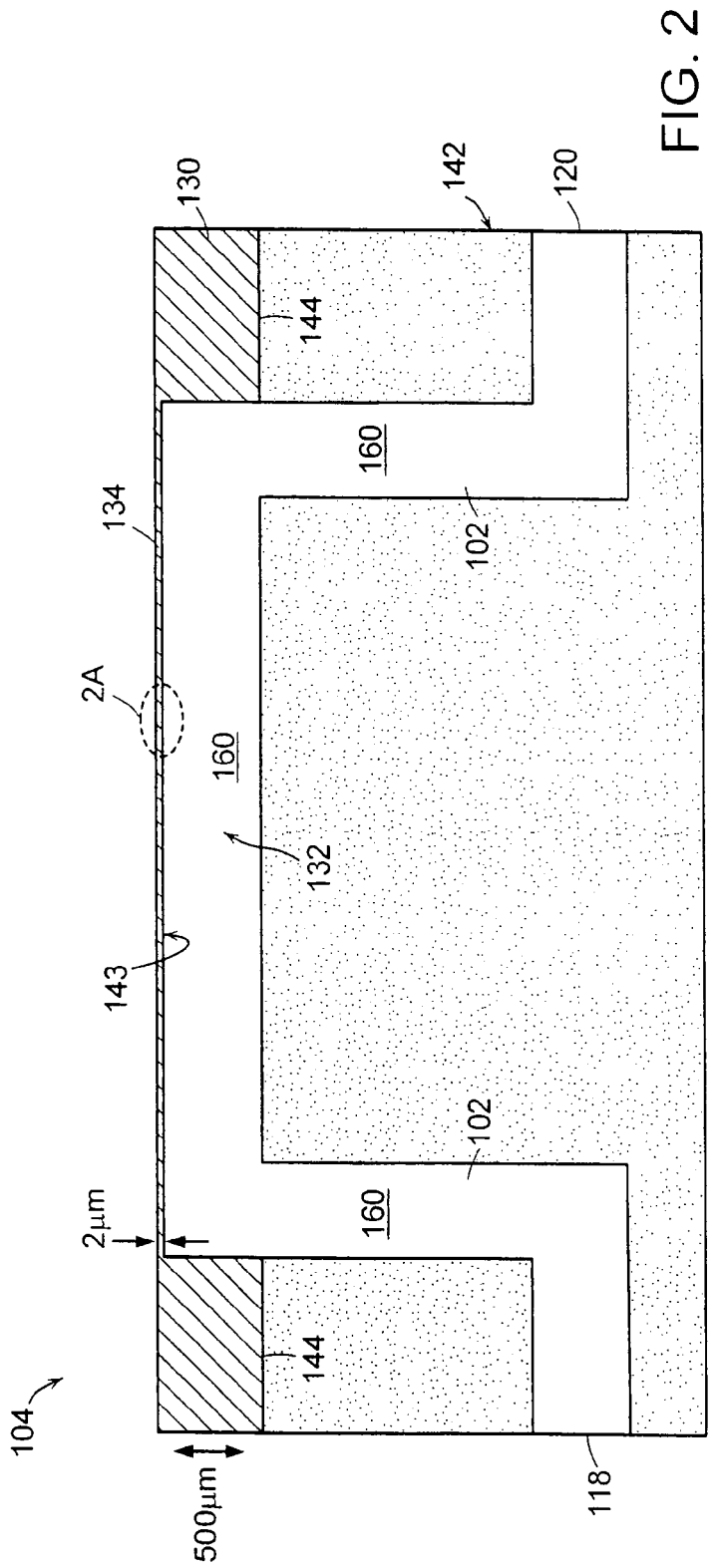

The FPW device 104 is shown in more detail in FIG. 2 and FIG. 2A. In an FPW device 104, strain energy is carried in bending and tension in the device. In some embodiments, it is desirable for the thickness-to-wavelength ratio of the FPW device 104 to be less than one, and in some cases much less than one. In general, the wavelength "$\lambda$" of the FPW device 104 is approximately equal to the pitch of the interdigitated electrodes as described herein. In one embodiment, the thickness-to-wavelength ratio of the FPW device 104 is 2 μm/38 μm. In other embodiments, the FPW device 104 is designed to isolate a particular mode (e.g., any mode from the zero$^{th}$ order mode to higher order modes) or bandwidth of modes associated with the device. For example, an FPW device 104 having a thickness/wavelength of 2 μm/38 μm as described above would isolate the 80$^{th}$ mode of the FPW device 104. The FPW device 104 can be designed to achieve this effect by selecting a particular pattern for the interdigitated electrodes deposited on the device. In one embodiment, the FPW device 104 is rectangular in shape. The FPW device 104 can, alternatively, be circular or elliptical, or some other planar shape.

In general, the FPW device 104 is constructed from a silicon wafer 130, using micro-fabrication techniques known in the art. In the described embodiment, a cavity 132 is etched into the wafer 130 to produce a thin, suspended membrane 134 that is approximately 1.6 mm long, 0.3 mm wide and 2 µm thick. The overall wafer 130 thickness is approximately 500 µm, so the depth of the cavity 132 is just slightly less than the wafer 130 thickness. A 0.5 µm layer 136 of aluminum nitride (AlN) is deposited on the outer surface (i.e., the surface opposite the cavity 132) of the membrane 134, as shown in the expanded view insert of FIG. 2A. Two sets of interdigitated metal electrodes 138 are deposited upon the AlN layer. A thin layer 140 of gold (approximately 500 angstroms) is deposited on the inner surface (i.e., the surface facing the cavity 132) of the membrane 134 to facilitate immobilization of capture agents (described in more detail below). In some embodiments, the first of the two sets of the interdigitated electrodes is an actuating or launching portion that is located on the left half side (as viewed in FIG. 2) of the membrane 134. The second of the two sets of interdigitated electrodes is a sensing or receiving portion that is located on the right half side (as viewed in FIG. 2) of the membrane 134. In some embodiments, the two sets of the interdigitated electrodes are located side-by-side along the length (viewed from left to right in FIG. 2) of the membrane 134, one of the two sets is the actuating or launching portion and the second of the two sets is the sensing or receiving portion.

In operation, instrument/control electronics 126 (referring to FIG. 1A) apply a time-varying electrical signal to at least one set of electrodes 138 to generate vibrations in the suspended membrane 134. The instrument/control electronics 126 also monitor the vibrational characteristics of the membrane 134 by receiving a sensor signal from at least a second set of electrodes 138. When liquid is in contact with the cavity side 132 of the membrane 134, the maximal response of the plate structure is around 15-25 MHz. The instrument/control electronics 126 compare a reference signal to the sensor signal from the second set of electrodes to determine the changes in the relative magnitude and phase angle of the sensor signal as a function of frequency. The instrument/control electronics 126 interpret these changes to detect the presence of the targeted analyte. In some embodiments, the instrument/control electronics also determines, for example, the concentration of the targeted analyte on the inner surface of the membrane 134.

Capture agents targeting the analyte of interest are immobilized on the thin layer of gold 140 covering the inner surface of the membrane 134, as described above. The surface can be coated with a suitable linking compound. Suitable linking compounds are commercially available. In one embodiment, the linking compound comprises biotin PEG disulfide, as described below. In another embodiment, thiol-terminated alkyl chains are linked to the gold surface forming a self-assembled monolayer (SAM). A fraction of the SAM chains are terminated with reactive groups (e.g., carboxyl) to allow covalent linking of capture agents to the SAM chains using biochemical process steps known in the art. The remainder of the SAM chains are terminated with non-reactive groups, preferably ones that have a hydrophilic character to resist nonspecific binding (e.g., oligomers of ethylene glycol). Other surface chemistries are described in the literature and can be used to produce a capture surface.

The FPW device 104 is packaged to allow electrical connections to the electrodes 138 on the outer surface of the membrane 134. Additionally, the FPW device 104 is mechanically supported by a channel block 142, to allow for the inner surface of the membrane 134 to contact the test solutions and an interface is provided for contacting the sensor surface 143 with the liquid sample. The channel block 142 creates a path (fluid chamber 160) for the test solutions to flow from an input port 118, past the inner surface of the membrane 134 and then out of an exit port 120. A seal 144 is formed between the FPW device 104 and the channel block 142 to prevent test solutions from escaping from the channels 102 formed within the combination of the FPW device 104 and the channel block 142. The channel block 142 thus forms a fluid chamber, of which the FPW device 104 comprises one of the interior walls.

The channels 102 through the combination of the FPW device 104 and the channel block 142 are approximately 0.5 mm in diameter. The channel block 142 can be formed from a variety of materials, including plastic, metal or ceramic, among other materials.

The system 100 includes one or more fluid control devices for changing at least one fluid property, such as flow, pressure, or trajectory to name a few, within the system 100. The pump 122 and valves 114 shown in FIG. 1A that direct and control the flows of various test solutions through the device and over the sensor surface 143 (as required to execute a test protocol) are all examples of fluid control devices. In general, a fluid control device changes the at least one fluid property in the vicinity of at least one surface within the fluid chamber 160 of the device 104. Generally, this is done to distribute the magnetic particles along at least a portion of the sensor surface 143. As described above, in some embodiments the fluid control device is a pump (e.g., a peristaltic pump, centrifugal pump, rotary pump, electro-osmotic pump). In some embodiments, the pump is located on the entrance side of the fluid chamber, and in other embodiments the pump is located on the exit side of the fluid chamber. In some embodiments, the device is a flow diverter (e.g., a plug, obstruction wall or baffle) that is disposed relative to the fluid chamber to alter the fluid flow in the vicinity of the at least one interior surface of the fluid chamber.

Referring to FIG. 1A, a single pump 122 is positioned on the waste side of the FPW device 104. Suction that the pump 122 generates draws buffer 110 or analyte in the sample 108 from their respective reservoir containers 112 on the supply side of the FPW device 104. Valves 114 are positioned on the supply side of the device 104 to control which test solution is directed over the sensor surface 143 at any time during the test protocol. The pump 122 controls the flow rate of the test.

A device for regulating temperature (e.g., a thermoelectric cooler) may be associated with the FPW device 104 and channel block 142. This reduces the impact of variable environmental conditions on the FPW device 104 output by maintaining the device 104 at a relatively constant, known temperature. In an alternative embodiment, a temperature sensor is included within the system 100, for example as part of the FPW device 104. The sensor signal from the FPW device 104 is scaled, at a specific instant in time (or during a period of time), based on the output of the temperature sensor, in order to produce a signal that is independent of the effects of temperature variations. This scaling could be done based on a mathematical model, or an analytical model, or some hybrid combination of a mathematical and analytical model.

In some embodiments of the system 100, a filter is included in the path of the test solution to selectively filter particles (e.g., magnetic particles and biological materials) of a particular size to prevent them from entering the fluid chamber. By way of example, a particular testing protocol may include steps for changing the filter during the test. This would allow different types (i.e., sizes) of analytes and magnetic particles to be directed into the fluid chamber, and thereby tested by the system 100, during different portions of the test.

In one embodiment, magnetic particles (e.g., paramagnetic or super-paramagnetic beads or microspheres), which have their surfaces coated with a capture agent, are mixed with a sample containing the analyte. After a prescribed mixing time analyte-particle complexes 146 result as do particles 147 that have bound nonspecific materials and particles 148 that have bound nothing. The particles 146, 147 and 148 are located in the sample reservoir 112.

The system 100 further includes a magnetic field inducing structure 150 for producing magnetic flux in the vicinity of the membrane 134. In FIG. 1A, the source of magnetic flux is a retractable magnet 150 arranged to normally be in close proximity to the membrane 134 of the FPW device 104. When the magnet 150 is in close proximity to the membrane 134, the magnet 150 produces a significant gradient magnetic field in the vicinity of the membrane 134. Under control of the instrument/control electronics 126, the retractable magnet 150 can be retracted away from the membrane 134 by a distance sufficient to substantially reduce magnetic fields in the vicinity of the membrane 134. In one embodiment, when in close proximity to the membrane 134, the magnet 150 is situated approximately 200 μm from the sensor surface 143 of the membrane 134. In another embodiment, when in close proximity to the membrane, the magnet 150 is situated between about 50 μm to about 100 μm from the sensor surface 143 of the membrane 134.

When the magnet 150 is in close proximity to the membrane 134, the magnet 150 provides a source of magnetic flux to draw the magnetic particles from the sample to the sensor surface 143. The analyte-particle complexes 146, as well as particles 147 with nonspecifically bound material and particles 148 with nothing bound, migrate from the liquid sample until they encounter the sensor surface 143. The analyte binds with the capture agent on the sensor surface 143. Thus, the analyte forms a link between the magnetic particle and sensor surface. The particles 147 with non-specifically bound material and particles 148 with nothing bound are held at the sensor surface 143 by the magnetic field. Additionally, weak binding forces can act between the particles 146, 147, and 148 and the sensor surface 143. During the wash step of the protocol (described in more detail below), the magnet 150 is retracted to reduce the magnetic force experienced by the particles that have accumulated at the sensor surface 143. The wash flow rate is increased to remove particles 147 and 148 that are not bound to the surface by analyte. Since the particles 147 with nonspecifically bound material as well as particles 148 with nothing bound are more weakly linked to the sensor surface 143 than the analyte-particle complexes 146, they release from the sensor surface 143 at a lower wash flowrate (and corresponding hydrodynamic force). Hence, removing the magnet 150 (i.e., substantially reducing the magnetic force experienced by the particles 146, 147, and 148 at the sensor surface 143) is used to distinguish between particles with analyte 146 from those without (particles 147 and 148). One technique for engaging and retracting the magnet 150 is to mount it on a carriage (not shown) that is actuated by a cam system (not shown).

The magnet 150 material, geometry and distance from the sensor surface 143 determine the field shape and field gradient, and therefore, the force that the analyte-particle complexes 146 experience. High strength permanent magnets for use as the retractable magnet 150 are available commercially. For example, 1 mm diameter cylindrical NdFeB magnets can be purchased from several vendors (e.g., Dexter Magnetic Technologies). In one embodiment, a 1 mm diameter and 5 mm long NdFeB magnet 150 is positioned within 0.1 mm of the sensor surface 143 when engaged. When retracted the magnet 150 is at least 0.5 mm from the sensor surface 143. Since the membrane 134 of the FPW device 104 is very thin (2 μm) and made of nonmagnetic materials (e.g., silicon, aluminum nitride or gold), the membrane 134 does not significantly perturb the magnetic field on the sensor surface 143 side of the device 104. As a result, very high magnitude magnetic fields and large field gradients can be achieved, as is necessary for high collection efficiencies.

The sample flow rate through the channels 102 is determined (e.g., specified by an operator) by the residence time necessary for good collection efficiency. The sample flow rate is adjusted so that the average velocity over the sensor surface 143 is between about 1 and about 5 mm/s. With an iron oxide paramagnetic particle with a diameter of approximately 3 μm, collection efficiencies approaching 50% can be achieved.

Other configurations of the source 150 of magnetic flux (i.e., the magnet) may be used. For example, an electromagnet can be used instead of a permanent magnet. The electromagnet includes pole pieces that extend to focus the field flux near the sensor surface 143 of the device 104.

Alternatively, a magnetizable material can be fashioned and positioned adjacent to the sensor surface 143 (within 0.1 mm), and a separate magnet combined with an open face of the magnetizable material to induce a magnetic field in the magnetizable material. The magnetic field induced in the material serves to locate desirable field gradients near the sensor surfaces 143. In this way, large, low cost magnets can be used, and a single magnet can be used to address multiple sensors, depending on the fashioning of the material. Examples of useful materials for this purpose are pure iron, high mu metals such as alloy 49 (high nickel content iron), sna silicon steels (1-2% silicon typical). An advantage of using such a magnetizable material with an associated magnet is that the sensor assembly can be simplified, allowing lower cost manufacturing. A low precision actuator can be used for engaging and retracting the magnet since the magnet need only contact the ferromagnetic core or be fully withdrawn. In the described embodiment where the magnet 150 is positioned in close proximity to the sensor surface 143, a higher level of precision is required to achieve good assay repeatability. Although there is some loss of field strength with this approach, it is still possible to design the overall system to achieve good capture efficiencies (e.g., >10%).

The shape of the tip of the field inducing structure (e.g., magnet or ferromagnetic material) may be tailored to enhance and/or concentrate the field gradient at the surface. Since the size of the FPW device 104 (e.g., 0.3 mm×1.6 mm) is typically smaller than conventionally formed magnets or machined inductors, the portion of the field inducing structure adjacent to the membrane 134 can be tapered to concentrate the magnetic field in one or more locations on the sensor surface 143. Tapering the tip acts to increase both the local field magnitude and the local field gradients. For example, a wedge-shaped tip is well suited to the current FPW device geometry.

One embodiment of the system 100 includes an optional second source 150a of magnetic flux that opposes or partially opposes the first source 150 of magnetic flux. This second source 150a of magnetic flux can be used to dislodge some of the magnetic particles that have adhered to the sensor surface 143. It may, for example, dislodge magnetic particles 148 that do not have any bound analyte; they would not be as strongly attached to the sensor surface 143 as the particles 146 that do have bound analyte. In some embodiments, the first source 150 of magnetic flux is turned off or moved away from the sensor surface 143 and then, the second source 150a of magnetic flux is positioned relative to the at least one surface of the fluid chamber to selectively remove magnetic particles. This may be done, for example, to remove magnetic particles 148 that do not have any bound analyte and therefore they are not as strongly bound to the sensor surface 143. This would achieve a similar effect as increasing the flow of fluid to remove magnetic particles 148 that do not have any bound analyte.

Controlling the distribution of the analyte-particle complexes 146 on the surface 143 of the device 104 can improve the device performance, since the device 104 has a suspended membrane 134 and not all parts of the membrane 134 contribute equally to the moving mass of the detectable resonance. For example, the system 100 can be constructed and arranged to distribute the analyte-particle complexes 146 within one third of the FPW device 104 width along the middle two-thirds of the centerline of the long axis of the membrane 134. Taking into account flow field effects, the shape of the tip of the field-inducing structure (e.g., magnet 150) can be such that the field magnitude and field gradient increase in the direction of the flow over the sensor membrane 134. That is, analyte-particle complexes 146 in the downstream regions, where the boundary layer is partially depleted of analyte, experience a higher field and field gradient than do analyte-particle complexes 146 in the upstream regions.

In general, the system 100 can be constructed and arranged to concentrate magnetic particles in one or more particular regions of the sensor surface 143. The response of the device 104 may not be uniform over the sensor surface 143 due to characteristics of the fabrication materials or the specifics of the sensor design. Thus, high sensitivity regions of the device 104 may be non-uniform and asymmetrical with respect to the long and short axis centerlines of the device 104. Thus, the tip of the field inducing structure may be shaped to concentrate magnetic particles in the region or regions of highest sensitivity.

Varying the flow rate through the device 104 can also be used to achieve a more uniform coverage of analyte-particle complexes 146 for a given magnetic field distribution. For a given field, magnetic particles interact with the sensor surface 143 as determined by the bulk fluid flow rate, much like a ballistic object might fall in the presence of the gravity body force. In this case, however, the magnetic induced force dominates. By varying the flow rate, the analyte-particle complexes 146 can be caused to interact with the sensor surface 143 at substantially different locations along the stream-wise flow direction. Furthermore, as the magnetic particles pile up (a non-desirable occurrence if they are to be exposed to the sensor surface 143) the flow can be reversed and subsequently pulsed forward in order to pull the pile over and thus communicate more particles with the sensor surface 143. In one embodiment of the system 100, selective location of the magnetic particles along the sensor surface 143 is achieved by selectively altering, over the course of the detection protocol, either one or both of the magnetic flux source and the property or properties of the fluid flow along the sensor surface 143.

One embodiment of the system 100 includes a device (e.g., optical, magnetic) for characterizing at least one property of the magnetic particles that are attached or attracted to the sensor surface 143. This device could be an integral part of the FPW device 104, or it could be a part of the magnet 150, or it could be a discrete component apart from other components of the system 100. Such a device may be used to detect the presence of the particles, and also to determine parameters related to the particle, for example, the size, quantity, concentration, or density of the particles that are attracted to the sensor surface 143.

One embodiment of the system 100 includes an identification device for allowing an operator or computer to identify the system 100 or a particular component of the system for tracking usage of the system or component. The identification device may include a symbol or image such as a bar code, an identification number, or other identifying mark. The identification device may include an actual component, passive or active, such as an RFID tag, an integrated circuit or other such component known in the art for providing identifying information. Many such devices are known in the art, although any contemplated identification device may be used.

Figure 3:
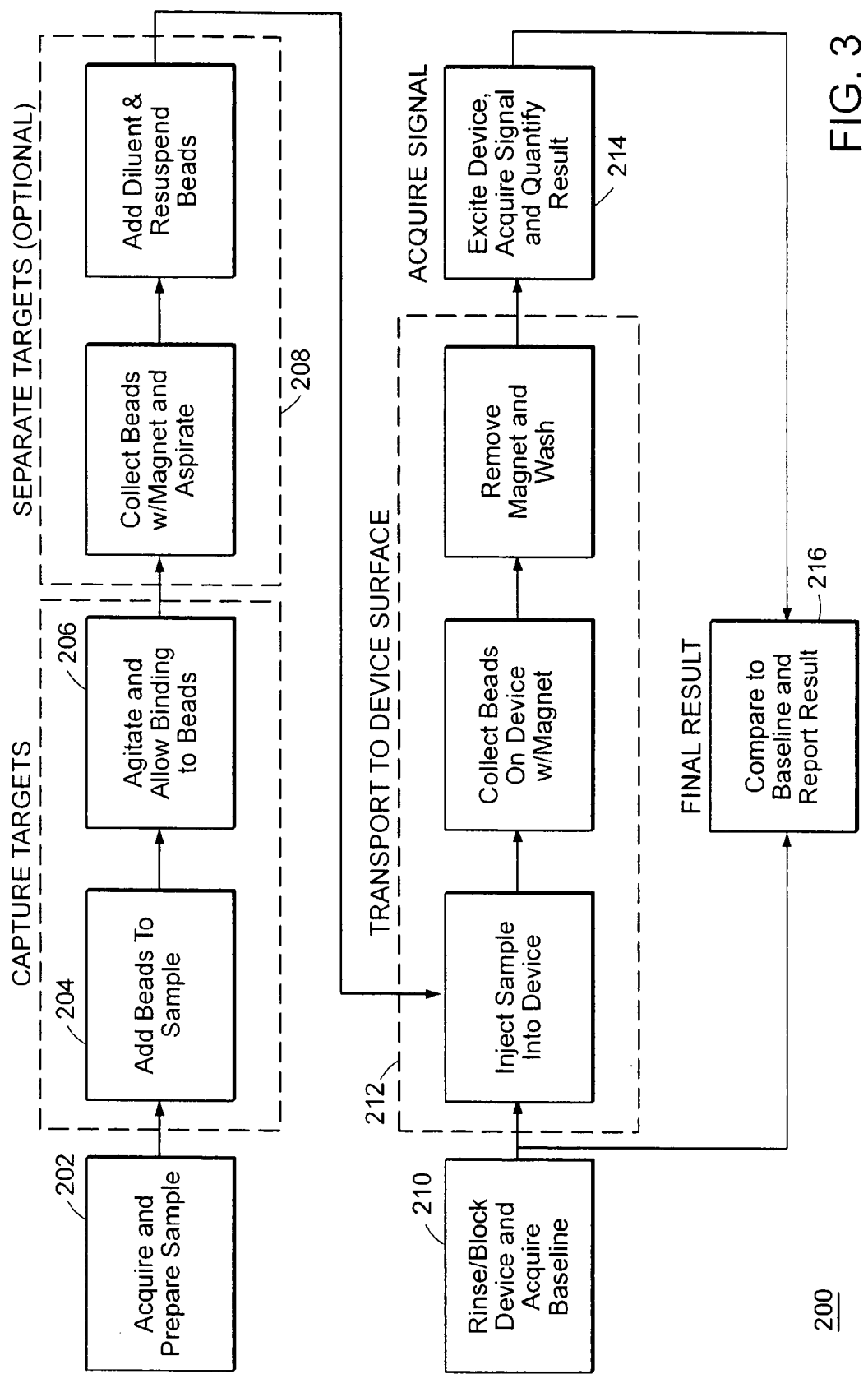
FIG. 3 shows a general detection protocol for using an FPW sensor in combination with analyte-particle complexes for detection of biological analytes.

A general detection protocol 200 for using an FPW device 104 in combination with analyte-particle complexes 146 for detection of biological analytes is shown in FIG. 3.

The first step 202 of the detection protocol 200 is acquiring and preparing 202 the analyte sample. Various preparation processes may need to be performed prior to testing, depending upon the particular type of analyte being tested. For example, to detect microbes in food (e.g., *E. coli* in ground beef), a sample would be first mixed with enrichment broth, stomached, incubated and filtered. For detecting proteins in blood, the sample would first be filtered or centrifuged and the serum separated. Specific examples of test protocols that include sample preparation steps are described herein.

The next step 204 of the detection process is mixing affinity-coated paramagnetic particles (i.e., beads) with the prepared analyte sample. Paramagnetic or super-paramagnetic particles are available commercially from a number of vendors (e.g., Dynal Biotech, Oslo, Norway). Typical diameters range from 50 nm to 10 µm, and such particles can be procured already coated with affinity agents (e.g., antibodies, proteins, and nucleic acid probes) targeting a variety of analytes (e.g., cells, proteins and nucleic acids). Alternatively, the particles can be purchased with various reactive chemical groups (e.g., epoxy, carboxyl, and amine) in order to attach a capture agent of choice. Standard biochemical protocols are available for this purpose.

The sample with paramagnetic particles added is agitated 206 for an amount of time determined by the particular analyte and capture agent. During this process, the particles bind with analyte so that the analyte is captured on the particles. In some cases, the sample can be tested directly at this point. But, in other cases it is advantageous to perform separation steps 208 to isolate the analyte bound to the particles from the rest of the original sample. These separation steps 208 reduce interference from other biological material in the assay. Manual or automated equipment for performing such separation steps is available commercially (e.g., Dexter Magnetic Technologies, Dynal Biotech). The basic process uses a magnet to localize the paramagnetic particles on a surface so that the majority of the sample liquid can be aspirated. The magnet (e.g., magnet 150 of FIG. 1A) is then removed, and clean buffer solution is added to re-suspend the particles.

In one embodiment, a baseline step 210 is executed prior to testing the processed analyte sample with the FPW device 104. During the baseline step 210, a reference solution 106 is flowed through the system to rinse/block the sensor 104, and the instrument/control electronics 126 excite the device 104 and records the resulting initial baseline signal from the device 104.

A sample transport step 212 follows the baseline step 210. The sample 108 containing the analyte-particle complexes 146 is flowed over the sensor surface 143 with the magnet 150 engaged. Analyte-particle complexes 146 are collected on the sensor surface 143. After a prescribed volume of sample 108 has flowed through the device 104, the magnet 150 is retracted to release the particles 147 and 148 from the sensor surface 143 that do not have bound analyte, and the flow is switched to a wash solution (e.g., buffer solution 110). The flow rate of the wash solution is increased to help remove loosely bound particles 147 and 148, as well as other material in the sample that may have bound to the sensor surface 143

An acquisition step 214 follows the sample transport step 212. Reference solution 106 is again run through the device 104, and the instrument/control electronics 126 excite the device 104 to acquire and record a final baseline signal from the device 104.

The system 100 determines the amount of analyte accumulated on the sensor surface 143 during the transport step 212 by comparing 216 the initial baseline signal and the final baseline signal, which correspond to the vibrational characteristics of the FPW device 104 in the reference solution before and after, respectively, the acquisition step 214. Analyte-particle complexes 146 bound to the sensor surface 143 change the vibrational characteristics of the FPW device 104, and the amount of change to the vibrational characteristics correspond to the amount of analyte-particle complexes bound to the sensor surface 143.

Figure 4:
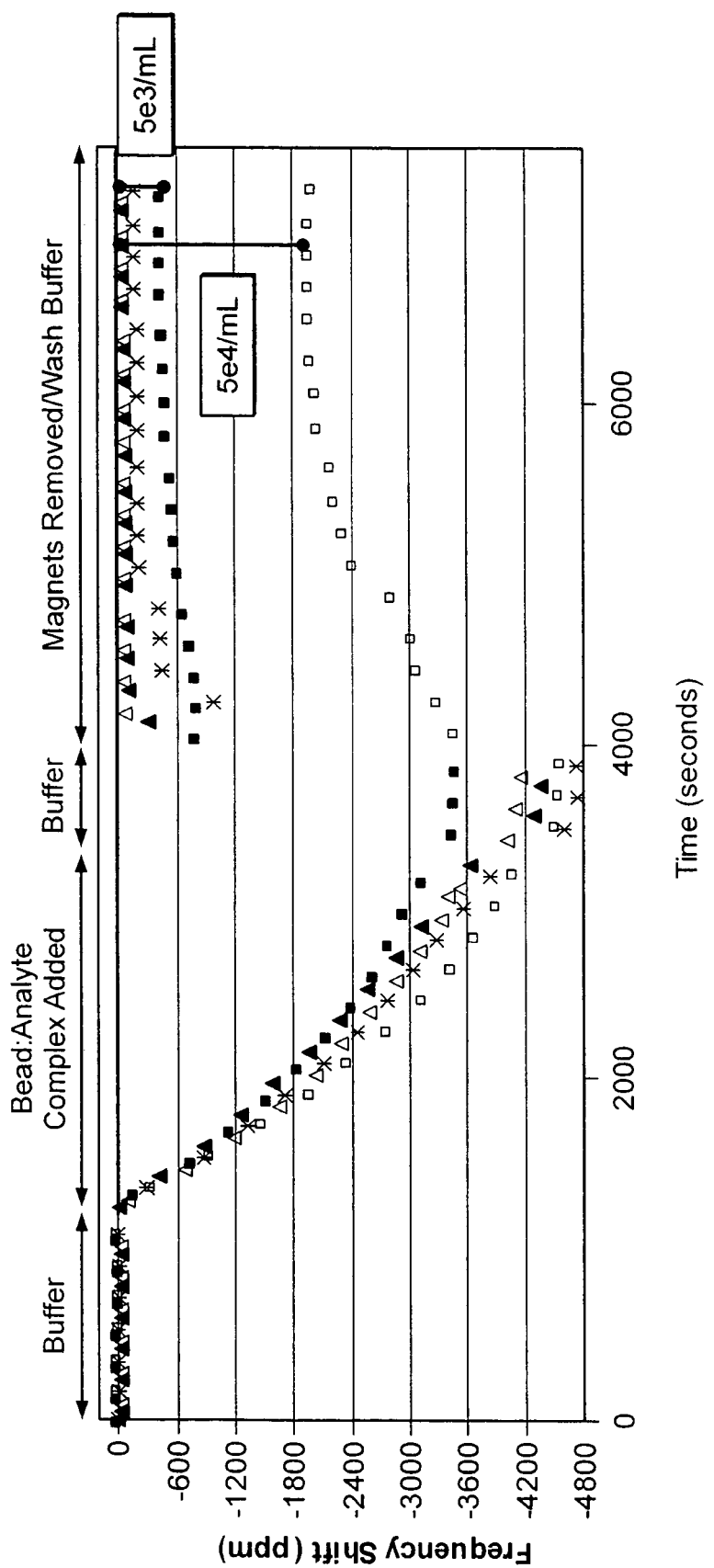
FIG. 4 shows the change in the signal from multiple FPW sensors as a function of time for an exemplary detection protocol.

FIG. 4 shows the change in the signal from multiple FPW devices 104 as a function of time for an exemplary detection protocol. The square symbols correspond to a device 104 exposed to an analyte; the triangles and stars correspond to negative controls (in which there is no analyte on the beads). The data shown in FIG. 4 (and FIG. 5 as described below) represent an exemplary detection protocol for which the analyte is *E. coli* bacteria, or generally a cellular analyte.

In this particular experiment, the frequency of a resonant peak was tracked. FIG. 4 shows that the resonant frequency of the FPW device 104 decreases as the magnetic particles 146, 147 and 148 accumulate on the surface. Once the magnet 150 is removed and some of the magnetic particles are washed away, the frequency of the device 104 increases. Eventually, the system establishes a final baseline that can be compared to the initial baseline taken at the start of the test, or to that of a control.

Figure 5:
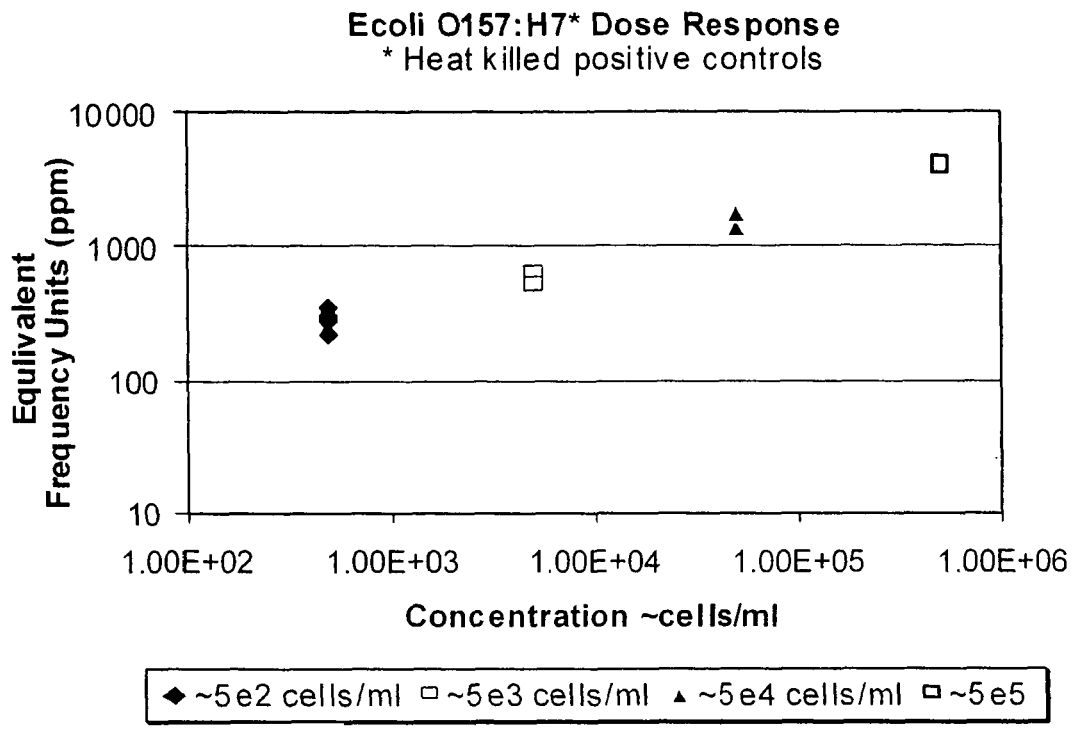
FIG. 5 is a summary plot showing the final signal change detected as a function of original analyte concentration.

FIG. 5 is a summary plot showing the final signal change detected as a function of original analyte concentration.

Figure 6:
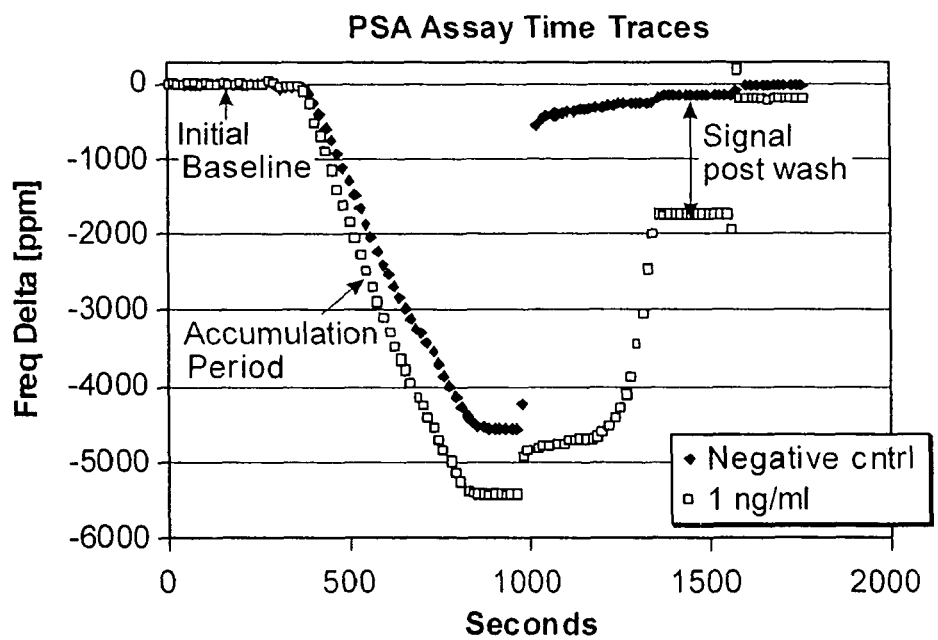
FIG. 6 shows a time evolution plot for a detection protocol, similar to the plot shown in FIG. 4, but rather for a PSA analyte.

Other detection protocols may be used with the system 100 described above. Individual steps can be eliminated or added depending on the requirements of a specific application or analyte. For example, FIG. 6 shows a time evolution plot for a detection protocol, similar to the one shown in FIG. 4. FIG. 6, however, depicts a detection protocol for a PSA assay, which demonstrates the capability of the system 100 for detecting proteins. Also, the flow direction can be reversed during the protocol. For example, reversing the flow direction may be useful for washing nonspecifically bound material from the device, or for making more efficient use of the available sample.

Another variation in the detection protocol includes alternating between wash steps and binding steps. This can allow better use of the dynamic range of the device. In come cases, a large fraction of the particles do not have bound analyte, especially at low analyte concentrations. By repeatedly binding and washing away particles, it is possible to accumulate more analyte-particle complexes 146 and, hence, improve the sensitivity of the measurement.

Changing or manipulating the magnetic field distribution at the sensor surface 143 during the transport step 212 can enhance the probability that the analyte attached to a particular particle encounters the sensor surface 143. For example, if the spatial distribution of the field is alternated during binding, it is possible to cause the paramagnetic particles at the sensor surface 143 to roll. In some embodiments, by controlling the spatial distribution of the field, an operator or the instrument/control electronics 126 can be used to control the rolling of the paramagnetic particles along the sensor surface 143.

As described above, introducing a second magnetic field (i.e., a second source of magnetic flux) in the system 100 can improve the control of the assay conditions and enhance the specificity of the assay. For example, during the binding or wash steps of the protocol as described above, applying a secondary magnetic field to the sensor surface 143 can act to pull off weakly bound magnetic particles. The strength of the secondary field can be tailored to generate a force on the analyte-particle complexes 146 at the sensor surface 143 that is below the binding force of the specifically bound analyte but above the typical binding force for nonspecifically bound material. This sequence of steps can be repeated multiple times during the assay to further increase the specificity of the test.

The relative binding strength of the various analyte-particle complexes 146 on the sensor surface 143 can be determined by increasing (continuously or discretely) this magnetic pull-off force during the wash step, while monitoring the response of the FPW device 104. Information on the relative binding strength can be used to distinguish between different analytes in the sample 108.

The particular way the sample interfaces with the device 104 can be different in other embodiments. In the above-described embodiments, the system 100 flows the sample through a channel to establish contact between the analyte-particle complexes 146 and the sensor surface 143. In an alternative variation of the system 100, the FPW device 104 is mounted on a probe and at least partially immersed into a test solution containing magnetic particles bound to an analyte. For this embodiment, the immersion is sufficient to place the bound magnetic particles in proximity to the sensor surface 143 so that the particles are attracted toward the sensor surface 143 and subsequently detected, as described herein. To obtain a baseline signal, the device 104 (or cartridge 103) is immersed in a reference test solution. In some embodiments, a portion of the device 104 (e.g., the membrane 134) is mounted to a probe. Further, only part of the sensor surface 143 of the membrane 134 is placed in contact with the solution containing magnetic particles bound to an analyte. In these embodiments, immersion or controlled movement of the probe in the fluid is sufficient to place the bound magnetic particles in proximity to the sensor surface 143 so that the particles are attracted toward the sensor surface 143 and subsequently detected.

Another alternative embodiment of the system 100 involves mounting the device 104 inside of a tube that can be partially immersed into a well holding the sample 108, and then retracted. A pump applies suction to draw sample into the tube and over the sensor surface 143 (or cartridge 103) when the sample is immersed. The sample is then ejected back into the well by reversing the pump or simply by venting the tube. This cycle of drawing and releasing the sample can be repeated to improve the collection efficiency and, therefore, the performance of the assay.

The following examples illustrate, for one embodiment of the system 100 described herein, steps for preparing and utilizing the system 100 for detecting an analyte.

EXAMPLE I

Generalized Method for Capture Agent Functionalization of a Surface of a Flexural Plate Wave Device 1. Deposit gold onto the surface (e.g., sensor surface 143) of the flexural plate wave device 104 and clean the gold surface 143 with, for example, oxygen plasma.

2. An ideal surface chemistry for the surface 143 of the gold is one that provides 1) non-specific binding resistance and 2) reactive groups located on the surface for covalent attachment of capture agents. An exemplary surface chemistry for the surface 143 of the gold is a self-assembled monolayer (SAM) of alkane thiols. The SAM can be formed from a mixture of two alkane thiols; one terminated with a reactive group for subsequent covalent attachment of capture agents, and one terminated with a non-reactive group. By way of example, a mixture of $EG_3$—OH (EG3) and $EG_6$—$OCH_2COOH$ (EG6) terminated $C_{11}$-alkane thiols may be used for this purpose. In one embodiment, the flexural plate wave device 104 (particularly the surface 143 of the device 104) is placed in contact with the alkane thiol solution and allowed to incubate at room temperature for, for example, about 16 hours. The surface 143 of the flexural plate wave device 104 is then rinsed with ethanol and blown dry with nitrogen.

3. The next step involves covalent attachment of capture agent or analyte to the surface 143 of the flexural plate wave device 104. A number of methods may be used for covalent attachment of capture agent or analyte. An exemplary method involves covalently linking a biotin linker moiety to the SAM, then binding a biotinylated antibody or analyte to the flexural plate wave device surface 143 via a streptavidin linking layer.

EXAMPLE II

Detecting *E. coli* 0157:H7 in Ground Beef Using, for Example, the Method of FIG. 3 (FIG. 5 Contains Data Representative of Various Concentrations of *E. coli*)

1. Prepare an analyte sample containing *E. coli* O157:H7 with a concentration greater than about 100 cfu/mL.

a. Concentrate the analyte sample in solution by performing an immunomagnetic separation. A variety of commercial instruments (e.g., PATHATRIX™ (antibody coated paramagnetic particles) by Matrix Microsciences and BEAD RETRIEVER™ (magnetic bead processor) by Dynal Biotech) or manual methods may be used to perform the immunomagnetic separation. An exemplary manual method involves:

b. Resuspend magnetic beads coated with *E. coli* antibody (e.g., DYNABEADS™ anti-*E. coli* 0157, available from Dynal Biotech) until the magnetic bead pellet in the bottom of the tube disappears. Place a microcentrifuge tube in the rack (e.g., a Dynal MPC-S) of a magnetic plate. Pipette 1-20 µL of magnetic bead stock solution into the tube (the volume of magnetic bead stock selected is based on desired final bead concentration).

c. Add 1 mL of the analyte sample to the tube in the rack of the magnetic plate and close the tube.

d. Invert the tube a few times. Incubate the solution in the tube at room temperature for 10 to 60 minutes with gentle continuous agitation to prevent magnetic beads from settling.

e. Invert the tube several times to concentrate the magnetic beads into a pellet on the side of the tube. Allow about 3 minutes for proper recovery.

f. Open the tube and carefully aspirate and discard the sample supernatant as well as the remaining liquid in the tube's cap.

g. Remove the magnetic plate.

h. Add 1 mL of wash buffer (PBS-TWEEN® (polyoxyethylene sorbitan monolaurate)) to the tube. Close the cap of the tube and invert the rack a few times to resuspend the beads.

j. Repeat steps e-h twice.

k. Mix the contents of the tube briefly using a vortex mixer.

2. Detection of *E. coli* O157:H7 a. Functionalize (similarly as described by the steps in A.3 and A.4) the surface 143 of a flexural plate wave device 104 with *E. coli* O157:H7 antibody.

b. Place a first inlet hose into a tube containing standard wash buffer (1× PBS with 0.05% TWEEN® 20 (polyoxyethylene sorbitan monolaurate)) and a second inlet hose into the tube containing the magnetic beads bound with *E. coli* O157:H7 (prepared in B.2). The first inlet hose and second inlet hose are joined by a t-joint so the two hoses are in fluid communication and fluid from either the first inlet hose or from the second inlet hose is directed to an inlet of the fluid chamber 160. Each of the two hoses has a valve that is capable of permitting or limiting the flow of fluid through respective hoses.

c. Place a first outlet hose in fluid communication with an outlet of the fluid chamber 160. Fluid from the first outlet hose is collected in a waste collection bottle.

d. A baseline output signal is obtained using the flexural plate wave device. The baseline signal is measured with standard wash buffer flowing into the fluid chamber 160 and out of the fluid chamber 160 for about 5 minutes at a standard pump speed (e.g., 200 µL/min).

e. The first source of magnetic flux 150 is engaged, and then fluid from the tube containing the analyte is directed into the inlet of the fluid chamber 160. Fluid is directed into the inlet of the fluid chamber 160 to accumulate magnetic beads bound with *E. coli* O157:H7 on the at least one surface 143 of the flexural plate wave device 160 until a desired amount is attached to the at least one surface 143. In one embodiment, the desired amount is achieved when, for example, there is a frequency shift in the output of the flexural plate wave device 104 of about 4000 ppm.

f. The flow of fluid from the tube containing the analyte is then discontinued. Fluid from the wash buffer tube is then directed into the fluid chamber 160 to wash away nonspecifically bound material (i.e., materials other than 1) magnetic beads and 2) magnetic beads with bound analyte).

g. The first source of magnetic flux 150 is then disengaged.

h. Initiate automatic wash protocol to remove any magnetic beads or matrix components.

i. The final signal output by the flexural wave plate device 104 is then measured. The baseline signal is compared with the final signal to determine the concentration of *E. coli* O157:H7 in the analyte sample.

EXAMPLE III

Detecting Prostate Specific Antigen (PSA) in Human Blood Serum Using, for Example, the Method Steps of FIG. 3

1. Prepare an analyte sample containing human serum obtained by centrifugation from a human blood sample.

2. Concentrate the analyte sample in solution by performing an immunomagnetic separation. A variety of commercial instruments (e.g., PATHATRIX™ (antibody coated paramagnetic particles) by Matrix Microsciences and BEAD RETRIEVER™ (magnetic bead processor) by Dynal Biotech) or manual methods may be used to perform the immunomagnetic separation. An exemplary manual method involves:

a. Resuspend magnetic beads coated with PSA antibody (e.g., DYNABEADS™ anti-PSA, available from Dynal Biotech) until the magnetic bead pellet in the bottom of the tube disappears. Place a microcentrifuge tube in the rack (e.g., a Dynal MPC-S) of a magnetic plate. Pipette 1-20 µL of magnetic bead stock solution into the tube (the volume of magnetic bead stock selected is based on desired final bead concentration).

b. Add 1 mL of the analyte sample to the tube in the rack of the magnetic plate and close the tube.

c. Invert the rack a few times. Incubate the solution in the tube at room temperature for 10 to 60 minutes with gentle continuous agitation to prevent magnetic beads from settling.

d. Invert the rack several times to concentrate the magnetic beads into a pellet on the side of the tube. Allow about 3 minutes for proper recovery.

e. Open the tube and carefully aspirate and discard the sample supernatant as well as the remaining liquid in the tube's cap.

f. Remove the magnetic plate.

g. Add 1 mL of wash buffer (PBS-TWEEN® (polyoxyethylene sorbitan monolaurate)) to the tube. Close the cap of the tube and invert the rack a few times to resuspend the beads.

h. Repeat steps d-g twice.

i. Mix the contents of the tube briefly using a vortex mixer.

3. Detection of PSA a. Functionalize (similarly as described by the steps in A.3 and A.4) the surface 143 of a flexural plate wave device 104 with PSA antibody.

b. Place a first inlet hose into a tube containing standard wash buffer (1× PBS with 0.05% TWEEN® 20 (polyoxyethylene sorbitan monolaurate)) and a second inlet hose into the tube containing the magnetic beads bound with PSA (prepared in B.2). The first inlet hose and second inlet hose are joined by a t-joint so the two hoses are in fluid communication and fluid from either the first inlet hose or from the second inlet hose is directed to an inlet of the fluid chamber 160. Each of the two hoses has a valve that is capable of permitting or limiting the flow of fluid through respective hoses.

c. Place a first outlet hose in fluid communication with an outlet of the fluid chamber 160. Fluid from the first outlet hose is collected in a waste collection bottle.

d. A baseline output signal is obtained using the flexural plate wave device 104. The baseline signal is measured with standard wash buffer flowing into the fluid chamber 160 and out of the fluid chamber 160 for about 5 minutes at a standard pump speed (e.g., 200 µL/min).

e. The first source of magnetic flux 150 is engaged, and then fluid from the tube containing the analyte is directed into the inlet of the fluid chamber 160. Fluid is directed into the inlet of the fluid chamber 160 to accumulate magnetic beads bound with PSA on the at least one surface 143 of the flexural plate wave device 104 until a desired amount is attached to the at least one surface 143. In one embodiment, the desired amount is achieved when, for example, there is a frequency shift in the output of the flexural plate wave device 104 of about 4000 ppm.

f. The flow of fluid from the tube containing the analyte is then discontinued. Fluid from the wash buffer tube is then directed into the fluid chamber 160 to wash away nonspecifically bound material (i.e., materials other than 1) magnetic beads and 2) magnetic beads with bound analyte).

g. The first source of magnetic flux 150 is then disengaged.

h. Initiate automatic wash protocol to remove any magnetic beads or matrix components.

i. The final signal output by the flexural wave plate device 104 is then measured. The baseline signal is compared with the final signal to determine the concentration of PSA in the analyte sample.

EXAMPLE IV

PSA in Calibrator I

By way of illustration, an experiment was conducted in which data was acquired using the system 100 of FIG. 1A, according to principles of the present invention. Dynal tosyl-activated super paramagnetic beads, functionalized with anti-Prostate Specific Antigen (PSA) capture antibody (PN 90205, Scripps Laboratories Inc. with offices in San Diego, Calif.) were exposed to samples. The samples comprised 1× PBS (Phosphate Buffered Saline) and 1% Bovine Serum Albumin (BSA), spiked with approximately 0 pg/mL, 10 pg/mL, 100 pg/mL and 500 pg/mL of free PSA [Fitzgerald Industries International, Inc. with offices in Concord, Mass.]. A bead concentration on the order of approximately $2 \times 10^4$ beads/mL with respect to sample was used in the experiment. Spiked samples where incubated with beads with gentle continuous agitation for 1 hour.

Eight of the Flexural Plate Wave (FPW) devices 104 of FIG. 2 provided on a single chip in a cartridge (not shown) were functionalized with complimentary anti-PSA antibodies (PN 90197, Scripps Laboratories Inc. with offices in San Diego, Calif.) after being first primed with 1× PBS containing 0.05% TWEEN® 20 (polyethylene glycol sorbitan monolaurate) [Sigma-Aldrich Co. with offices in St. Louis, Mo.].

Data was acquired and analyzed as described. for example, in the U.S. patent application entitled "Methods and Apparatus for Assay Measurements" by Masters et al. filed on May 2, 2006 . A baseline measurement (similarly as described previously herein) of eight individual frequencies, each corresponding to tracked sensor phases, each with respect to reference signals, was made at about 17800 seconds. Tracking phases are initially selected for each device to be within a resonance band of the device, near a frequency where the magnitude of response is near a peak value and where the phase response has significant linear range with respect to frequency change. When tracking the sensor phases, at each time point, individual device tracking frequencies are found by 1) sweeping each device over a range of frequencies and recording the phase of response at each excitation frequency with respect to a reference signal, 2) fitting a function relating excitation frequencies to measured phase for each device, and 3) using that function to compute the tracking frequency corresponding to the previously determined tracking phase.

In this embodiment, the devices are operated near 20 MHz and the sweep range is approximately 20 kHz. Over this range, the phase characteristic is substantially linear allowing the fit function to be linear. The reference signal for each device comprises the output of a network of passive electrical components, resistors and capacitors, simultaneously driven by the excitation. The reference network is selected to match the attenuation and provide a preferred phase shift for the devices near resonance. Baseline frequencies are referenced to, and normalized by, the tracked frequency and are shown as parts per million (ppm) at a selected point in time.

The sensing surface 143 of each device 104 was functionalized with capture agent. Gold coated chips were cleaned using an oxygen plasma source in which typical processing conditions were about 50 W for about 2 minutes. The chips were subsequently immersed in pure ethanol for 30 minutes. Next, the chips were transferred to a 0.5 mM solution of biotin PEG disulfide solution (Cat No. 41151-0895, POLYPURE™ AS with offices in Oslo, Norway) in ethanol and allowed to incubate overnight. The chips were transferred back into a pure ethanol solution for 30 minutes. The chips received a brief, final ethanol rinse and were blown dry using a nitrogen stream. Variations on preparation conditions can be made with similar results achieved.

The resultant biotinylated surface of the devices 104 was coated with NEUTRAVIDIN™ (PN 31000, Pierce Biotechnology, Inc. with offices in Rockford, Ill.) by flowing a 10 µg/ml solution of NEUTRAVIDIN™ over the biotinylated surface for 1 hour. Antibody was biotinylated according to the manufacturer's instructions (PN F-6347, Invitrogen Corporation with offices in Carlsbad, Calif.) and then coupled to the NEUTRAVIDIN™ coated surface, by flowing 5 µg/ml solution of the biotinylated antibody (diluted into 1× PBS 0.1% BSA buffer), over the NEUTRAVIDIN™ coated surface for 1 hour.

PSA sample was introduced and simultaneously a magnetic field was generated near the sensor surfaces 143 from about 17900 to about 18200 seconds. Samples of approximately 0 pg/mL, 10 pg/mL, 100 pg/mL and 500 pg/mL of free PSA were each provided to two different devices 104 (total of eight devices). The samples were flowed over the sensors at approximately 100 µL/min for a total sample run/volume of 500 µL flowing over the sensors. In this manner, Dynal tosyl-activated super paramagnetic beads coated with free PSA were bound to a substantial surface (surface 143) of the devices 104. Each bead was bound to the surface 143 of the devices 104 by a plurality of bonds. Each plurality of bonds giving rise to the discriminatory force with which each binds to the surface of the device. The characteristic of association and dissociation of an ensemble of beads for each sample determines the concentration of analyte in that sample.

Figure 11:
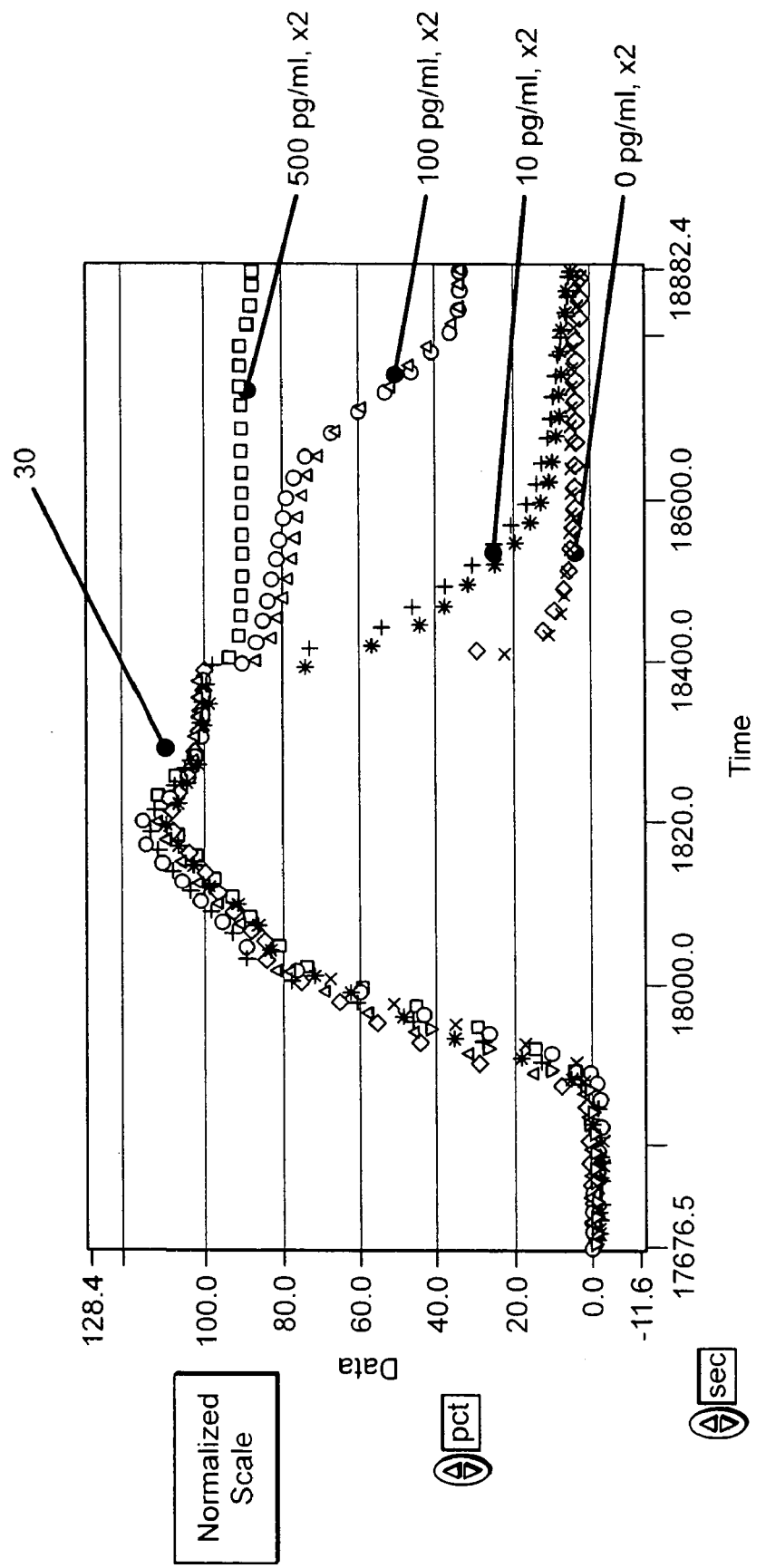
FIG. 11 shows the change in signal from multiple FPW sensors as a function of PSA concentration.

At approximately 18200 seconds the sample was replaced with priming buffer (1× PBS, 0.05% TWEEN® 20 (polyethylene glycol sorbitan monolaurate)). As shown in FIG. 11, a change (see location 30) in each of the signals was observed from 18200 seconds to 18400 seconds and represents the change in bulk fluid properties associated with switching from the sample fluids back to the buffer fluid. At approximately 18400 seconds the magnetic field was disengaged. The flow speed of the buffer fluid (1× PBS containing 0.05% TWEEN® 20 (polyethylene glycol sorbitan monolaurate)) was approximately 50 µL/minute between about 18200 seconds and 18400 seconds (corresponding to a flow speed of approximately 1.5 mm/second at the sensor surface 143).

The flow speed was increased over the next 450 seconds (from about 18400 seconds to about 18850) from approximately 50 µL/min to approximately 300 µL/min in linear increments (the flow speed was increased by about 17 µL/min every 30 seconds for 450 seconds then the flow speed was reduced to approximately 50 µL/min). In this manner, a controlled external influence (i.e., the flow speed in this embodiment) was applied to the beads by increasing the flow speed between about 18400 and about 18850 seconds). The portion of curves between about 18400 and about 18850 seconds represents a signal that is indicative of the change in the amount of beads (and other non-specific material) bound to the sensor surfaces 143 over that time period.

FIG. 11 is a graphical illustration of a plot of the data acquired versus time. The Y-Axis of the plot is the change in relative magnitude of the signal output by the device 104 (in parts per million) at a tracked sensor phase near the resonance of the device 104. The X-Axis of the plot is time in units of seconds. The plot is the change in tracked frequency referenced to and normalized by a tracked frequency at a selected point in time.

The data for each curve shown in parts per million of tracked frequency, was further normalized by the value of that curve at about 18350 seconds and referenced to the baseline frequency that was measured before introduction of the sample fluid. Each data curve was thereby scaled to a value of 100% at about 18350 seconds compared to when sample is introduced. The data associated with each of the normalized curves was then integrated with respect to time over the 450 seconds (from about 18400 seconds to about 18850 seconds) after the magnetic field was removed at about 18400 seconds.

The integration was performed by accumulating respective device signal levels, each interval level multiplied by the respective interval time periods, and dividing the final sum by the period over which the sum was performed. This provides the time normalized amount of material elements (beads) bound to the surfaces 143 of the devices, and these values are shown here to be a measure of concentration of analyte associated with each sample. In this manner, the concentration of analyte is determined based on the change in the amount of material elements bound to the surfaces 143 of each device 104 during the period of time between about 18400 seconds to about 18850 seconds. As shown in FIG. 11, approximately 10 pg/mL of free PSA was detected within less than about 9 minutes of introducing the sample into the system.

In some embodiments, data points are omitted that are, for example, outside the normal variation observed in the curves. For example, spurious data points that vary by more than an order of magnitude in value relative to adjacent data points may be omitted from subsequent analysis. The data points may be removed from the data by, for example an operator or by a computer program.

EXAMPLE V

Competitive Assay for Estradiol in Serum

A sheep monoclonal antibody specific for free estradiol was coupled to Dynal M280-tosyl activated beads using standard methods.

A sensor surface was constructed by coupling disulphide-PEG-biotin to the gold sensor surface, then coupling NEUTRAVIDIN™ (Pierce PN 31000) and then biotinylated antibody was performed as described above.

BSA coupled estradiol, E2-6-CMO-BSA (Sigma PN E5630) was then coupled to the antibody surface by flowing 10 ug/ml BSA coupled estradiol diluted in 1× PBS buffer over the antibody surface for 1 hour. Since the estradiol is coupled to multiple amine sites on the BSA (30 mols of estradiol per mol of BSA) the aforementioned approach provides for a moderately dense small molecule surface presented to solution.

Sample solutions comprising 70% charcoal striped human serum (Texas Biologicals), 30% 1× PBS 0.05% TWEEN® 20 (polyethylene glycol sorbitan monolaurate), were made with free estradiol (Sigma) spiked in at 0 pg/ml, 10 pg/ml, 30 pg/ml, 200 pg/ml. Beads, in concentration ~$2 \times 10^4$/ml were incubated with sample for 2 hrs. The beads were then flowed over the FPW using typical protocol and results obtained in approx 0.5 hrs (similarly as described herein).

In some samples danazol was also added as an decomplexing antagonist, to remove any interfering molecules such as Sex Hormone Binding Protein from the estradiol. Approximately 10-100 ng/ml levels were added.

Figure 12:
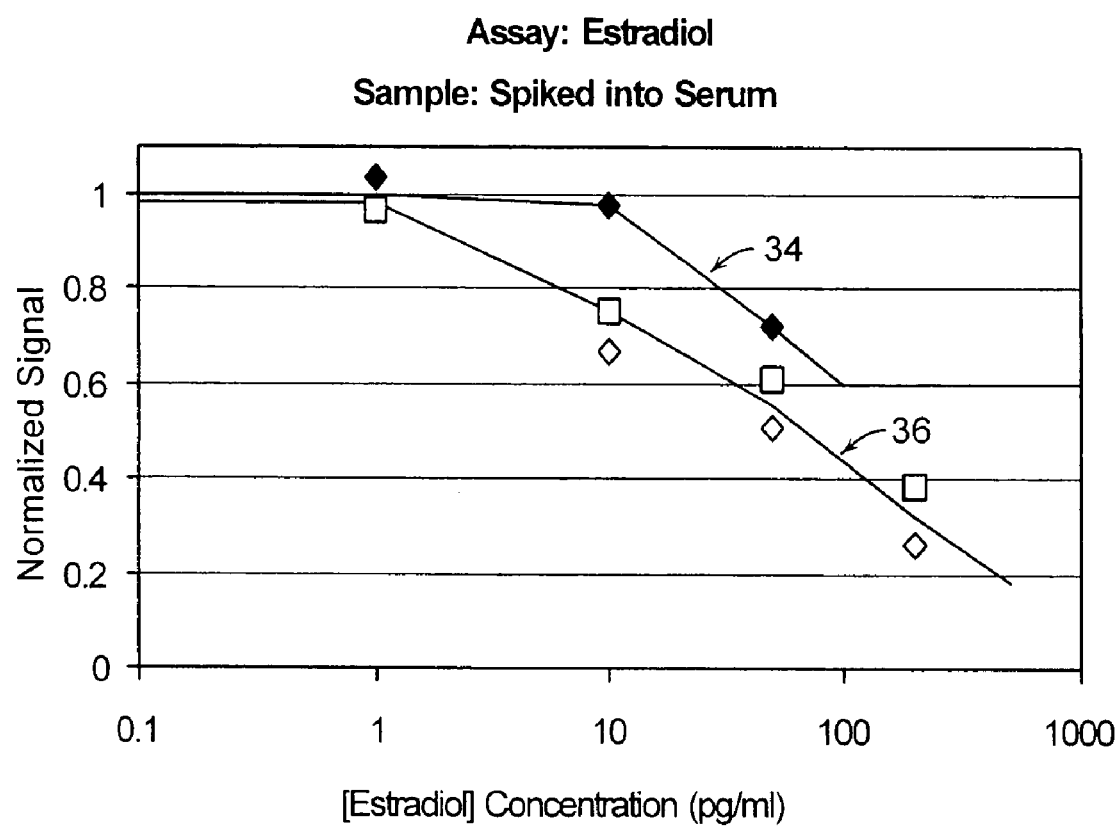
FIG. 12 shows the change in signal from multiple FPW sensors as a function of estradiol concentration in serum.

Sample was flowed over the FPW at approximately 70 uL/min with magnetic field engaged and beads were accumulated on the sensor surfaces. A wash protocol beginning at 50 ul/min, ending at 500 ul/min, with 50 ul/min intervals every 30 seconds was used to wash the bound beads off the sensor surfaces. FPW signals were normalized by exposure levels giving normalized signals, and these signals were integrated over the wash period. As shown in FIG. 12, less than 10 pg/ml can be detected in the presence of the antagonist additive 36, and less than 50 pg/ml can be detected in the absence of the antagonist additive 34.

EXAMPLE VI

Competitive Assay for FK-506

Figure 10B:
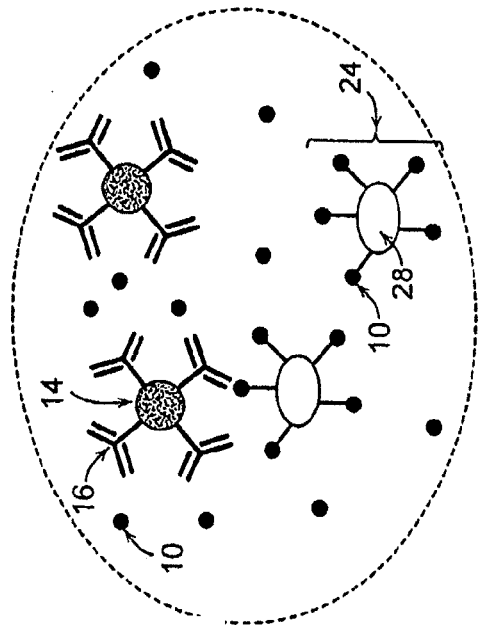
FIG. 10 is a schematic of one embodiment of the present invention, where the competitor molecule comprises a carrier and two or more analyte molecules of interest bound thereto, and the sensing surface of the acoustic device is coated with a capture agent that is capable of binding to the analyte of interest.
Figure 10D:
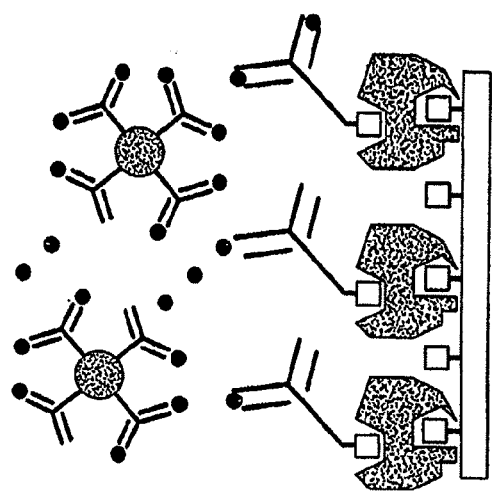
Figure 10A:
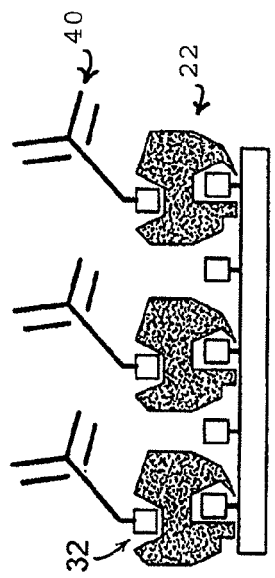
Figure 10C:
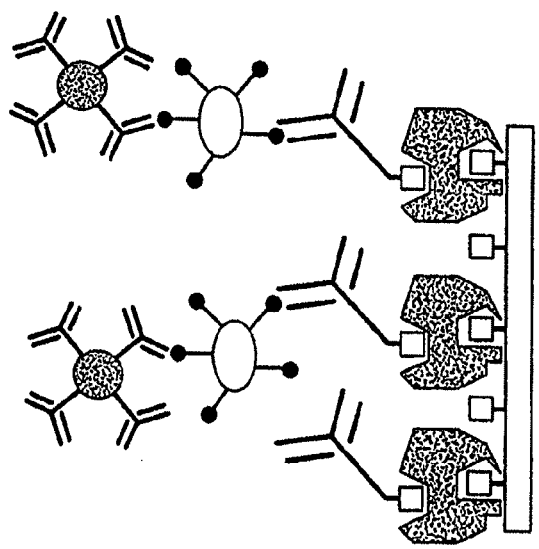
Figure 13:
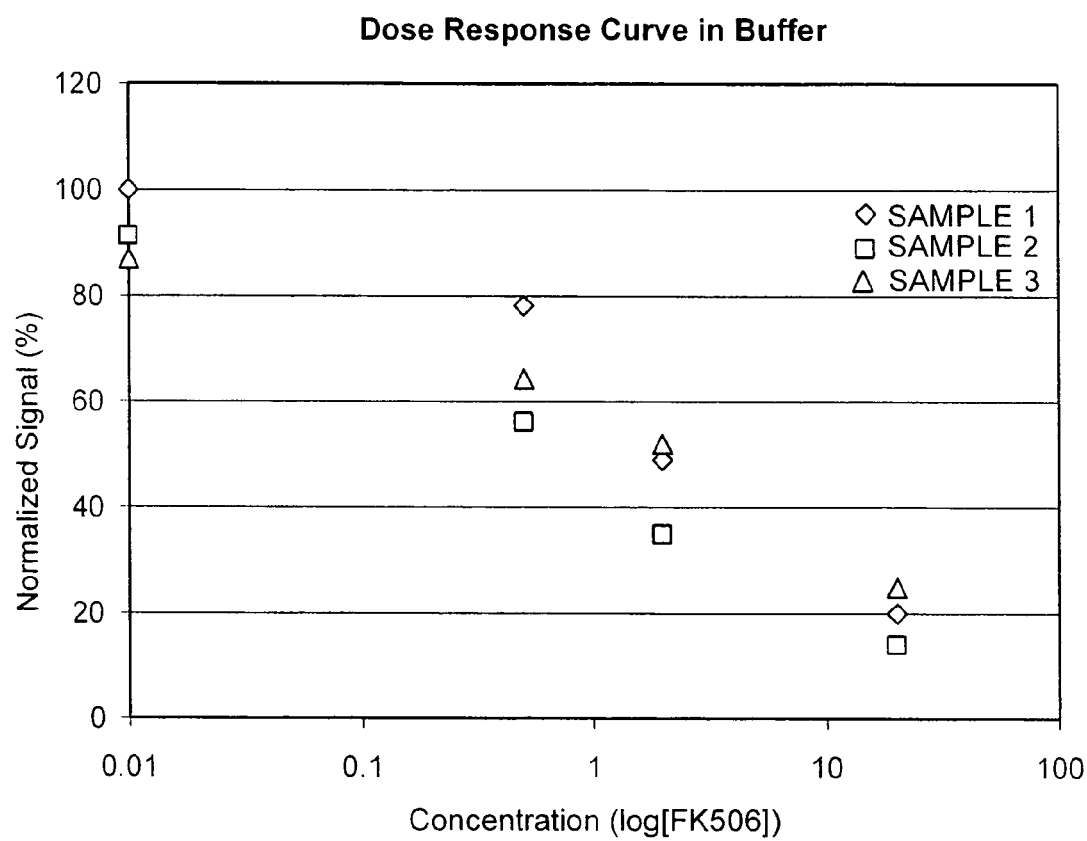
FIG. 13 is a dose response curve of FK-506 in buffer.
Figure 14:
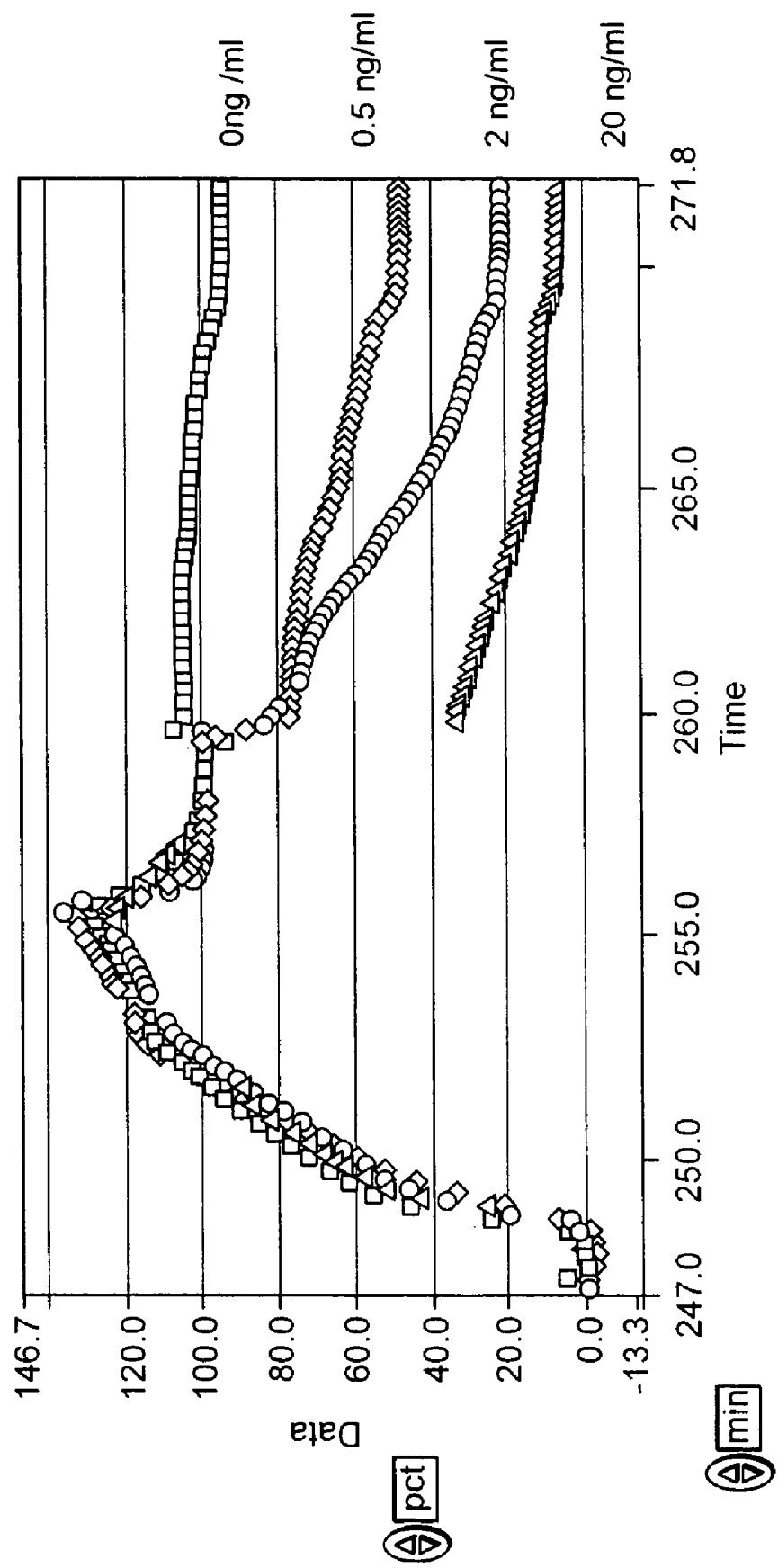
FIG. 14 shows the change in signal from multiple FPW sensors as a function of FK-506 concentration in buffer.

1. FK-506 was added to buffer (0.05% PBS TWEEN® 20 (polyethylene glycol sorbitan monolaurate) containing 1% BSA) to produce analyte samples with FK-506 concentrations of 0, 0.5, 2.0, and 20 ng/ml.
2. Eight µl of $1 \times 10^7$/ml anti-FK-506 IgM coated beads prepared as described above were added to each sample and incubated for 30-60 min. at room temperature. The beads are prepared by coupling anti-FK-506 IgM (Fitzgerald Industries Intl) to paramagnetic beads according to the manufacturer's instructions (Invitrogen Corporation). The analyte samples were concentrated in solution as described above.
3. Five hundred µl of a solution comprising carrier (HRP) labeled with FK-506 (Diasorin Inc.) were added to the sample and incubated for 60 min. at room temperature.
4. The samples were analyzed using an FPW device where the sensor was functionalized with capture agent (anti-FK-506 IgM). Referring to FIG. 10A, the sensor 12 was functionalized with NEUTRAVIDIN™ 22 as described above, and anti-FK-506 IgM was biotinylated 32 using standard biotinylation methods. As shown in FIG. 10B, analyte 10 (in this instance FK-506) was mixed with competitor molecule 24 and particles 16 labeled with capture agent 14 (in this instance anti-FK-506 antibody). For this example, the competitor molecule 24 comprised the carrier HRP labeled with the analyte FK-506). As shown in FIGS. 10C and 10D, a lower level of FK-506 in the sample is expected to allow the particles to bind to the competitor molecule and thereby to bind to the sensor surface. A higher level of FK-506 is expected to result in fewer particles binding to the sensing surface because more of the particles will be bound to FK-506 from the sample. As shown in FIGS. 13 and 14, FK-506 concentrations ranging from 0.5 ng/ml to 20 ng/ml were detected in as little as 15 min from introducing the sample into the device (similarly as described herein).

EXAMPLE VII

Competitive Assay for FK-506 in Blood

Figure 15:
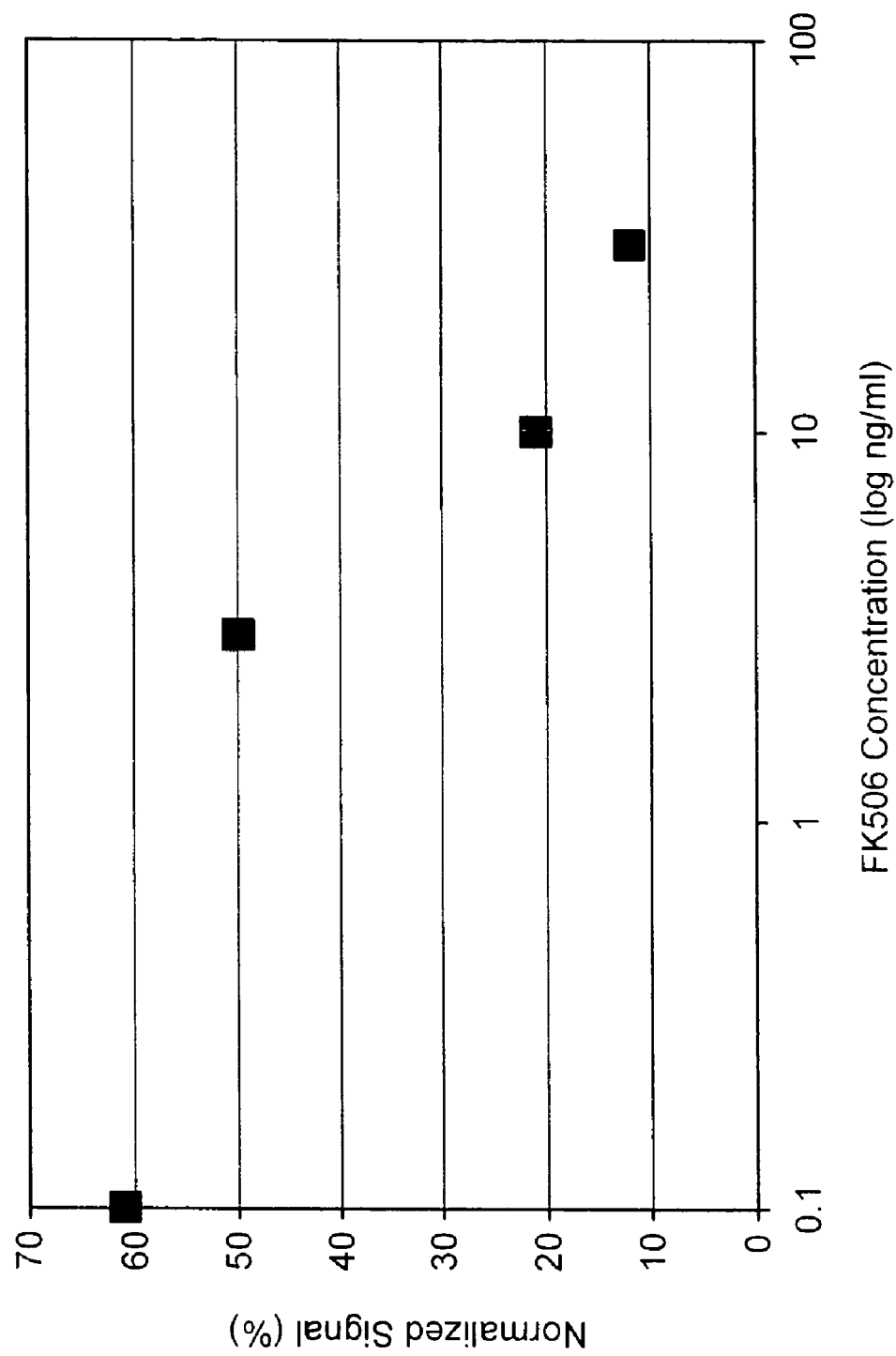
FIG. 15 is a dose response curve of FK-506 in serum.
Figure 16:
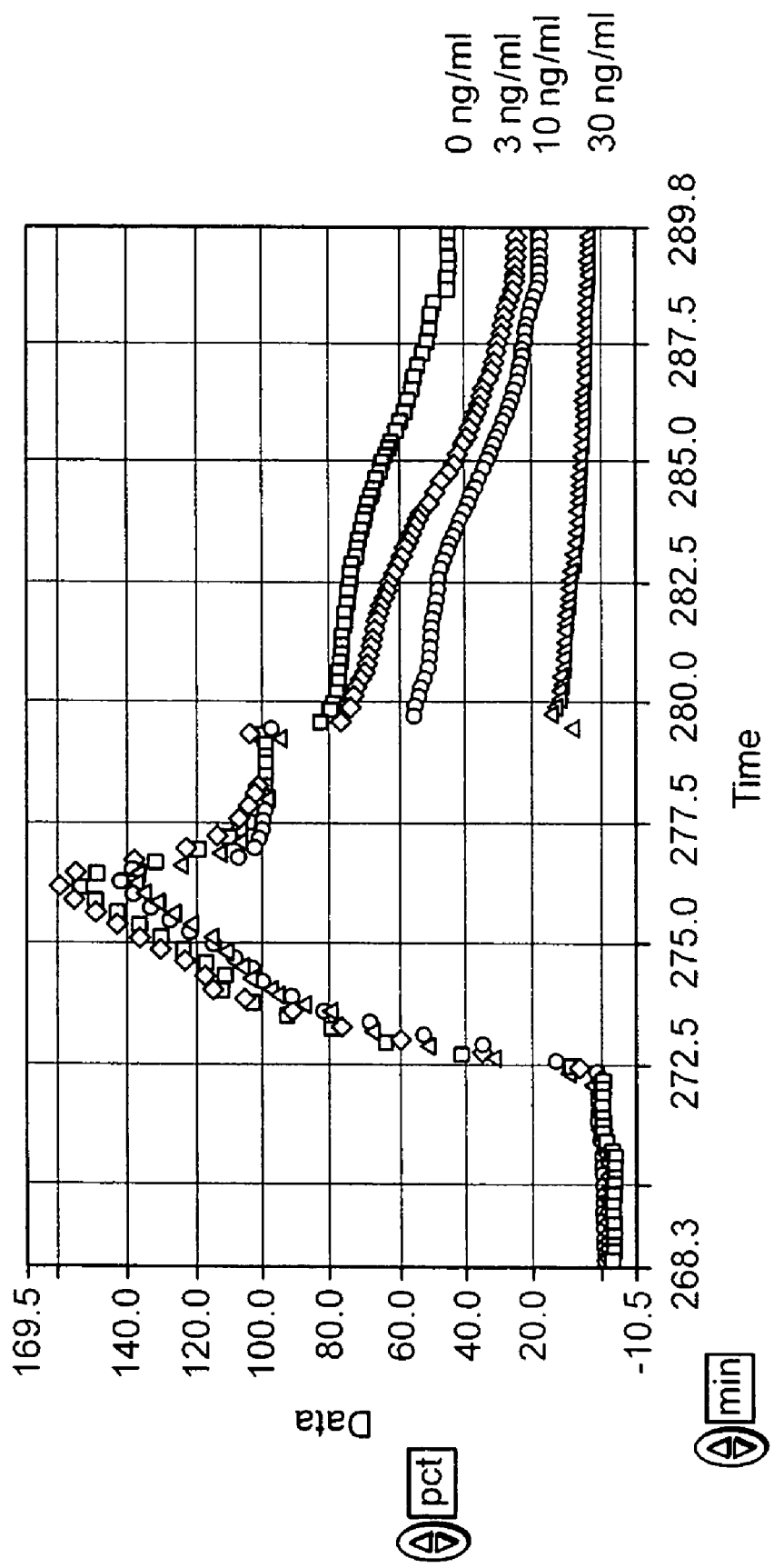
FIG. 16 shows the change in signal from multiple FPW sensors as a function of FK-506 concentration in serum.

1. Four samples each of one 100 µl of blood was spiked with 0, 3, 10, or 30 ng/ml FK-506. The drug was extracted from the blood matrix by performing a protein digestion protocol according to the manufacturer's instructions (Diasorin Inc.).
2. Six hundred microliters of protein digestion reagent was added to each sample.
3. The sample was mixed by vortexing, and incubated for 15 min. at room temperature (about 23° C.), producing a semi-transparent mixture.
4. The digestion reaction was stopped by incubating the samples at 75° C. for 35 min, producing a dark brown mixture.
5. The sample was mixed by vortexing and centrifuged at 1800 g for 10 min, producing 500-600 µl of supernatant.
6. Five hundred microliters of supernatant was transferred into a new tube, the four samples the same concentration of FK-506 were combined in one tube, producing 2 ml of supernatant for each concentration of FK-506.
7. The samples were analyzed as described above. As shown in FIGS. 15 and 16, FK-506 concentrations ranging from 0.5 ng/ml to 20 ng/ml were detected in as little as 8 min from introducing the sample into the device.

EXAMPLE VII cTroponin in Buffer

Three monoclonal capture antibodies (Fitzgerald 10-T79—clone numbers M8010521, M0110609 and M0110510) were coupled to Dynal M280 Tosyl activated beads in the ratio 2:2:1 respectively. Monoclonal Ab, 10-T79B, clone number M8010509 was biotinylated with the Invitrogen labeling kit F-6347 and coupled to gold coated FPW sensors using the POLYPURE™ biotin PEG disulphide linker (as described above), subsequently modified with NEUTRAVIDIN™ (Pierce PN 31000).

Figure 18:
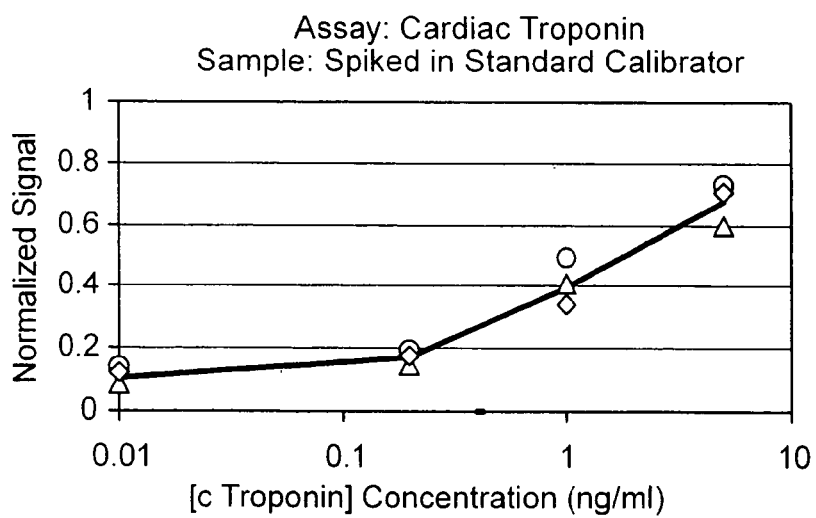
FIG. 18 shows a dose response curve of c-Troponin-I in buffer.

Troponin I (cardiac) antigen was diluted into 1× PBS 1% BSA samples in the concentrations 0 ng/ml, 0.2 ng/ml, 1 ng/ml and 5 ng/ml. Beads (also referred to herein as particles) were added in the concentration of $\sim 2 \times 10^4$/ml and samples incubated for 7-10 mins before been drawn to the sensor (3-5 mins), followed by a 5 min wash. The results are shown in FIG. 18. Background levels pertaining to samples containing 0 ng/ml of analyte are plotted at 0.01 ng/ml for reference.

EXAMPLE VIII cTroponin in Charcoal Stripped Serum

Samples were prepared with 70% charcoal stripped serum, 30% phosphate buffered saline 0.05% TWEEN® 20 (polyethylene glycol sorbitan monolaurate). Cardiac troponin I (Biospacific) was added to final concentrations 0 ng/ml, 0.4 ng/ml, 1 ng/ml and 5 ng/ml. Beads were functionalized with anti-cTroponin antibody (Biospacific PN A34440) according to the Dynal standard protocol, and were incubated with sample for 15 minutes before the sample was flowed over respective sensors.

Figure 19:
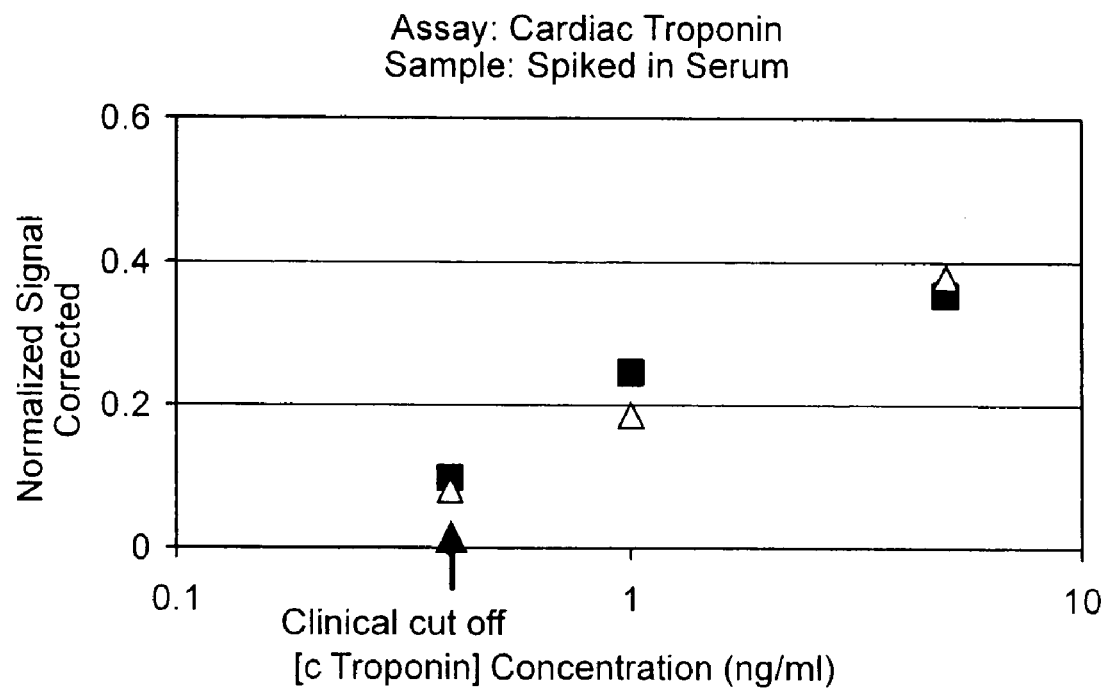
FIG. 19 shows a dose response curve of c-Troponin-I in serum.

Sensors where functionalized with NEUTRAVIDIN™ and biotinylated polyclonal antibody (Biospacific PN G-129-C) as described above. The beads/complexes mixture was flowed over the sensor and sensors were washed by flowing buffer at 15 uL/min for 5 mins. Data was observed at a time point of 2 minutes post magnetic field removal. 0 ng/ml samples were used to subtractive correct signal for background level. As shown in FIG. 19, as little as 0.4 mg/ml of cTroponin was detected.

EXAMPLE IX cTroponin in Lysed Whole Blood

Samples were constructed with 50% whole blood (Texas Biologicals) 50% phosphate buffered saline 0.05%

TWEEN® 20 (polyethylene glycol sorbitan monolaurate). Cardiac troponin I (Biospacific) was added at concentrations 0 ng/ml, 0.4 ng/ml, 1 ng/ml and 5 ng/ml. Beads functionalized with anti-cTroponin antibody (Bioscpacific PN A34440) according to the Dynal standard protocol) were incubated with sample for 15 minutes before the results flowed over respective sensors.

Figure 20:
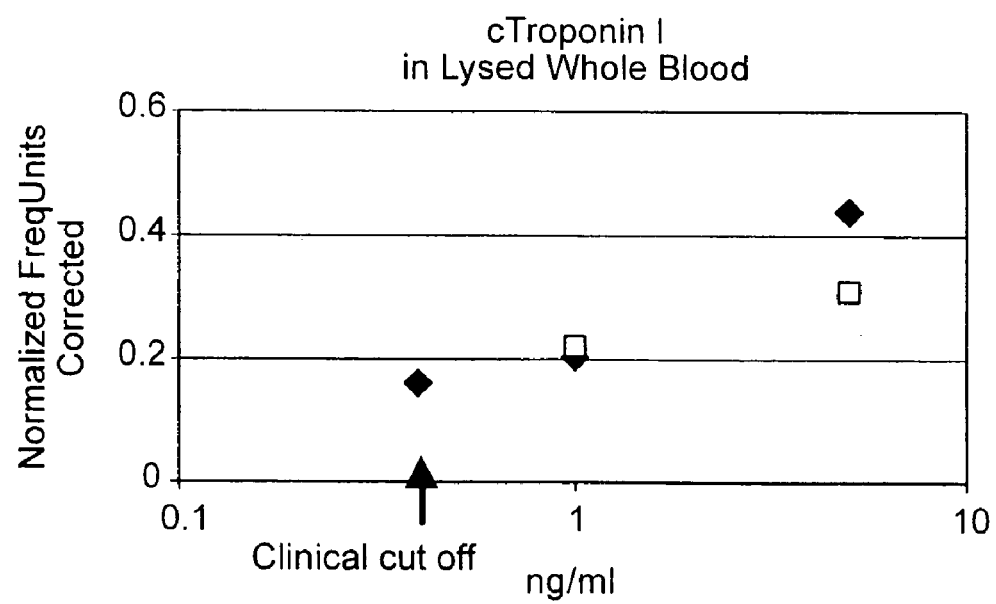
FIG. 20 shows a dose response curve of c-Troponin-I in lysed whole blood.

Sensors where functionalized with NEUTRAVIDIN™ and biotinylated anti-cTroponin polyclonal antibody (Biospacific PN G-129-C) as described above. After exposing the sensor to the beads/complexes, sensors were washed by flowing buffer from 50 uL/min through 150 uL/min in increments of 10 ul/min every 30 seconds. Signal data was integrated over a substantial portion of the washing period. 0 ng/ml samples were used to subtractive correct signal for background level. As shown in FIG. 20, as little as 0.4 mg/ml of cTroponin was detected.

EXAMPLE X

CHO-HCP Detection

Functionalizing Beads—Dynal M280 tosyl activated beads (described above) were coupled with anti-CHO-TCP polyclonal antibody (CygnusTechnologies F015) using the manufacturer's standard protocol.

Sensors were prepared using the same polyclonal antibody. The polyclonal antibody was biotinylated as described above and applied to FPW sensor surfaces first using a sub layer of biotin PEG disulphide, POLYPURE™ PN#41151-0895 applied to gold FPW surfaces, the POLYPURE™ coated subsurface subsequently layered with NEUTRAVIDIN™, Pierce PN 31000, and finally functionalized with the biotinylated capture antibody, in similar fashion as previously described above.

Figure 21:
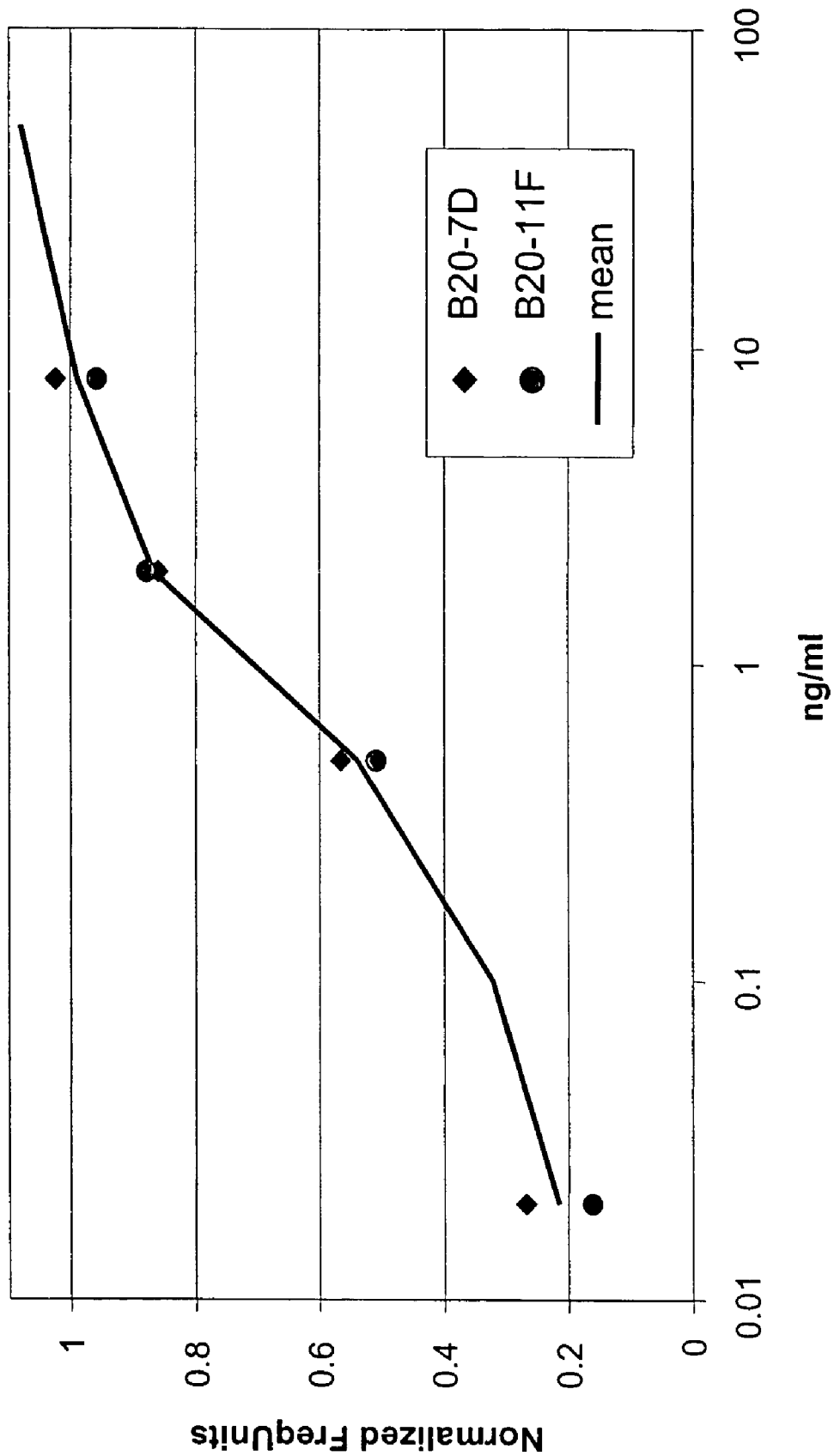
FIG. 21 shows a dose response curve of CHO-HSP in buffer.

Antigen was diluted in 1× PBS 1% BSA in the concentrations 0 ng/ml, 0.6 ng/ml, 2 ng/ml and 10 ng/ml to make spiked samples. The spiked samples were incubated with functionalized beads at a concentration of about $1 \times 10^4$-$5 \times 10^4$ beads/ml. Samples were incubated with the functionalized beads for 2 hrs. A ~20 minute FPW detection process was performed in similar fashion to the PSA example described earlier. Microparticle loading onto the sensors, post sample incubation, took approximately 3 minutes at 70 ul/min flow rate (210 uL of sample used per sensor). After loading, buffer was introduced, 1× Phosphate Buffered Saline with 0.5% TWEEN® 20 (polyethylene glycol sorbitan monolaurate), yielding a baseline measure of accumulated microparticles. The attractive magnetic field was then removed and microparticles where exposed to washing flow rates in a similar range as in the PSA assay example above. As shown in FIG. 21, methods provided herein are at least as sensitive as standard ELISA assays at detecting host cell protein. Furthermore, the total time for testing CHO-HCP was in the range of 2.5 hrs, as compared to the recommended ELISA 5 hr protocol.

EXAMPLE XI

Protein A/G Functionalized Sensor

Sensors were functionalized using using protein A/G. FPW chips with gold surfaces were functionalized with protein A/G, by first cleaning the surface of the chip by dipping the chip into acetone for 10 minutes, followed by ethanol for 10 minutes. The chip was then ashed in $O_2$ plasma (50 W, 2 minutes) on both the electrode side and the well side. Five mg of recombinant protein A/G (Pierce PN 21186) was suspended in 2 mls of PBS to give 2.5 mg/ml stock solution. Prior to incubation on the gold surfaces, the protein A/G stock solution was diluted to 750 ug/ml. Protein A/G (750 ug/ml) solution was added to the chip in individual wells. The chip was placed in a humidity chamber and incubated for 18 hours. The chip was then throuroughly rinsed with with 1× PBS or DI water, dried and packaged into a cartridge.

The surface can be calibrated, with known concentrations of antibody. In addition, the antibody can be stripped from the calibrated surface and the calibrated surface resused. The antibody can be stripped from the sensor surface by washing the surface with 0.1 M phosphoric acid. The stripped surface can be resused more than 10 times.

To load samples, buffer (1× Phosphate Buffered Saline, 0.05% TWEEN® 20 (polyethylene glycol sorbitan monolaurate)) was added to the cartridge to wet the surface of the sensor. Samples having a final monoclonal antibody concentration of 0.1 mg/ml or 0.01 mg/ml in BSA buffer (prepared by diluting 6 mg/ml of stock solution in the sensor wetting buffer (1× Phosphate Buffered Saline, 0.05% TWEEN® 20 (polyethylene glycol sorbitan monolaurate)) were introduced into the cartridge and direct frequency shift signals of monoclonal antibody binding to the protein A/G was detected. Detection occurred over 1-4 minutes of sample loading. After 2 minutes of sample loading at 50 uL/min (so net 100 uL of diluted sample used) the sample was switched back to buffer and the signal from the sensor leveled out. After each reading and after buffer has flushed out sensor wells, a solution of 0.1 M phosphoric acid was flowed over the sensor for 1 minute, removing (also referred to herein as stripping) the bound monoclonal antibodies and reviving the surface for the next run. The process was repeated three times with the samples. The results for both the 0.1 mg/ml and 0.01 mg/ml samples were reproducible within 5-10%.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. An apparatus for assessing purity of a bioprocess fluid, comprising:
   a) a fluid chamber having at least one opening for the bioprocess fluid to enter;
   b) a flexural plate wave device defining at least a portion of at least one interior surface of the fluid chamber and capable of being coated with a plurality of first capture agents capable of binding one or more biological markers in the bioprocess fluid;
   c) a monitoring device to monitor at least one signal output by the flexural plate wave device;
   d) a plurality of magnetic particles capable of being coated with a plurality of second capture agents capable of binding one or more biological markers in the bioprocess fluid; and
   e) a retractable source of magnetic flux positioned external to the fluid chamber close to the at least one interior surface of the fluid chamber to create a magnetic field gradient to selectively attract magnetic particles toward a surface of the flexural plate wave device.

2. The apparatus of claim 1, wherein the at least one interior surface of the fluid chamber further comprises a plurality of first capture agents bound to the surface of the flexural plate wave device, wherein the plurality of first capture agents are capable of binding the one or more biological markers.

3. The apparatus of claim 1, wherein the plurality of magnetic particles further comprises a plurality of second capture agents bound to the plurality of magnetic particles, wherein the plurality of second capture agents are capable of binding one or more biological markers.

4. The apparatus of claim 1, wherein the plurality of first capture agents are indirectly bound to the surface of the flexural plate wave device.

5. The apparatus of claim 1, wherein the plurality of first capture agents are directly bound to the surface of the flexural plate wave device.

6. The apparatus of claim 1, wherein the plurality of first or second capture agents are a plurality of polypeptides.

7. The apparatus of claim 1, wherein the plurality of first or second capture agents comprise a polyclonal antibody.

8. The apparatus of claim 1, wherein the one or more biological markers comprise a host cell protein.

* * * * *